US011672775B2

(12) United States Patent
Phares et al.

(10) Patent No.: US 11,672,775 B2
(45) Date of Patent: Jun. 13, 2023

(54) TREPROSTINIL PRODRUGS

(71) Applicant: United Therapeutics Corporation, Silver Spring, MD (US)

(72) Inventors: Ken Phares, Hillsborough, NC (US); Hitesh Batra, Herndon, NC (US); Liang Guo, Vienna, VA (US); Adam Marc Silverstein, Cary, NC (US)

(73) Assignee: United Therapeutics Corporation, Silver Spring, MD (US)

( * ) Notice: Subject to any disclaimer, the term of this patent is extended or adjusted under 35 U.S.C. 154(b) by 147 days.

(21) Appl. No.: 17/140,705

(22) Filed: Jan. 4, 2021

(65) Prior Publication Data
US 2021/0121433 A1    Apr. 29, 2021

Related U.S. Application Data

(63) Continuation of application No. 15/716,007, filed on Sep. 26, 2017, now abandoned.

(60) Provisional application No. 62/399,737, filed on Sep. 26, 2016.

(51) Int. Cl.
*A61K 31/27* (2006.01)
*A61K 31/216* (2006.01)
*A61K 31/335* (2006.01)
*A61K 31/222* (2006.01)
*A61P 9/12* (2006.01)
*A61K 9/00* (2006.01)
*A61K 31/192* (2006.01)
*A61K 31/265* (2006.01)

(52) U.S. Cl.
CPC ............ *A61K 31/27* (2013.01); *A61K 9/0019* (2013.01); *A61K 31/192* (2013.01); *A61K 31/216* (2013.01); *A61K 31/222* (2013.01); *A61K 31/265* (2013.01); *A61K 31/335* (2013.01); *A61P 9/12* (2018.01)

(58) Field of Classification Search
CPC .. A61K 31/192; A61K 31/216; A61K 31/222; A61K 31/265; A61K 31/27; A61K 31/335; A61K 9/0019; A61P 9/12
See application file for complete search history.

(56) References Cited

U.S. PATENT DOCUMENTS

| | | |
|---|---|---|
| 4,306,075 A | 12/1981 | Aristoff |
| 5,153,222 A | 10/1992 | Tadepalli et al. |
| 5,234,953 A | 8/1993 | Crow et al. |
| 6,054,486 A | 4/2000 | Crow et al. |
| 6,441,245 B1 | 8/2002 | Moriarty et al. |
| 6,521,212 B1 | 2/2003 | Cloutier et al. |
| 6,528,688 B2 | 3/2003 | Moriarty et al. |
| 6,700,025 B2 | 3/2004 | Moriarty et al. |
| 6,756,033 B2 | 6/2004 | Cloutier et al. |
| 6,765,117 B2 | 7/2004 | Moriarty et al. |
| 6,803,386 B2 | 10/2004 | Shorr et al. |
| 6,809,223 B2 | 10/2004 | Moriarty et al. |
| 7,199,157 B2 | 4/2007 | Wade et al. |
| 7,384,978 B2 | 6/2008 | Phares et al. |
| 7,417,070 B2 | 8/2008 | Phares et al. |
| 7,544,713 B2 | 6/2009 | Phares et al. |
| 7,879,909 B2 | 2/2011 | Wade et al. |
| 7,999,007 B2 | 8/2011 | Jeffs et al. |
| 8,232,316 B2 | 7/2012 | Phares et al. |
| 8,242,305 B2 | 8/2012 | Batra et al. |
| 8,252,839 B2 | 8/2012 | Phares et al. |
| 8,349,892 B2 | 1/2013 | Phares |
| 8,350,079 B2 | 1/2013 | Walsh |
| 8,410,169 B2 | 4/2013 | Phares et al. |
| 8,461,393 B2 | 6/2013 | Sharma |
| 8,481,782 B2 | 7/2013 | Batra et al. |
| 8,497,393 B2 | 7/2013 | Batra et al. |
| 8,536,363 B2 | 9/2013 | Phares et al. |
| 8,563,614 B2 | 10/2013 | Wade et al. |
| 8,609,728 B2 | 12/2013 | Rothblatt et al. |
| 8,653,137 B2 | 2/2014 | Jeffs et al. |
| 8,658,694 B2 | 2/2014 | Jeffs et al. |
| 8,747,897 B2 | 6/2014 | Kidane et al. |
| 8,765,813 B2 | 7/2014 | Wade et al. |
| 8,940,930 B2 | 1/2015 | Batra et al. |
| 9,029,607 B2 | 5/2015 | McGowan et al. |
| 9,050,311 B2 | 6/2015 | Phares et al. |
| 9,156,786 B2 | 10/2015 | Batra et al. |
| 9,199,908 B2 | 12/2015 | Phares et al. |
| 9,255,064 B2 | 2/2016 | Malinin et al. |
| 9,278,901 B2 | 3/2016 | Phares et al. |
| 9,278,902 B2 | 3/2016 | Tang et al. |
| 9,278,903 B2 | 3/2016 | Tang et al. |
| 9,339,507 B2 | 5/2016 | Olschewski et al. |
| 9,346,738 B2 | 5/2016 | Jain et al. |
| 9,358,240 B2 | 6/2016 | Olschewski et al. |
| 9,371,264 B2 | 6/2016 | Becker et al. |
| 9,388,154 B2 | 7/2016 | Yiannikouros et al. |
| 9,394,227 B1 | 7/2016 | Zhang et al. |
| 9,422,223 B2 | 8/2016 | Phares et al. |
| 9,505,737 B2 | 11/2016 | Becker et al. |
| 9,624,156 B2 | 4/2017 | Phares et al. |
| 9,643,911 B2 | 5/2017 | Zhang et al. |
| 2008/0200449 A1 | 8/2008 | Olschewski et al. |

(Continued)

FOREIGN PATENT DOCUMENTS

WO    WO-00/57701 A1    10/2000
WO    WO-2005/007081 A2    1/2005
(Continued)

OTHER PUBLICATIONS

Guidance for Industry: Bioequivalence Studies with Pharmacokinetic Endpoints for Drugs Submitted Under an ANDA, Dec. 2013, http://www.fda.gov/downloads/Drugs/GuidanceComplianceRegulatoryInformation/Guidances/UCM377465.pdf, (24 pages).

(Continued)

Primary Examiner — Kara R McMillian
(74) Attorney, Agent, or Firm — Foley & Lardner LLP

(57) ABSTRACT

Provided are novel prodrugs of treprostinil, as well as methods of making and methods of using these prodrugs.

6 Claims, 42 Drawing Sheets

(56) References Cited

U.S. PATENT DOCUMENTS

| | | |
|---|---|---|
| 2008/0280986 A1 | 11/2008 | Wade et al. |
| 2009/0036465 A1 | 2/2009 | Roscigno et al. |
| 2009/0124697 A1 | 5/2009 | Cloutier et al. |
| 2012/0197041 A1 | 8/2012 | Batra et al. |
| 2013/0184295 A1 | 7/2013 | Sprague et al. |
| 2013/0331593 A1 | 12/2013 | McGowan et al. |
| 2014/0024856 A1 | 1/2014 | Giust et al. |
| 2014/0275262 A1 | 9/2014 | Phares et al. |
| 2014/0275616 A1 | 9/2014 | Batra et al. |
| 2014/0323567 A1 | 10/2014 | Laing |
| 2015/0148414 A1 | 5/2015 | Malinin et al. |
| 2015/0166503 A1 | 6/2015 | Becker et al. |
| 2015/0299091 A1 | 10/2015 | Batra et al. |
| 2015/0315114 A1 | 11/2015 | Hering et al. |
| 2015/0328232 A1 | 11/2015 | Malinin et al. |
| 2015/0376106 A1 | 12/2015 | Batra et al. |
| 2016/0030355 A1 | 2/2016 | Kidane et al. |
| 2016/0030371 A1 | 2/2016 | Phares et al. |
| 2016/0045470 A1 | 2/2016 | Reddy et al. |
| 2016/0051505 A1 | 2/2016 | Phares et al. |
| 2016/0107973 A1 | 4/2016 | Batra et al. |
| 2016/0129087 A1 | 5/2016 | Christe et al. |
| 2016/0143868 A1 | 5/2016 | Olschewski et al. |
| 2016/0175319 A1 | 6/2016 | Freissmuth et al. |

FOREIGN PATENT DOCUMENTS

| | | |
|---|---|---|
| WO | WO-2009/152160 A1 | 12/2009 |
| WO | WO-2014/110491 A1 | 7/2014 |
| WO | WO-2016/010538 A1 | 1/2016 |
| WO | WO-2016/038532 A1 | 3/2016 |
| WO | WO-2016/055819 A1 | 4/2016 |
| WO | WO-2016/081658 A1 | 5/2016 |
| WO | WO-2016/105538 A1 | 6/2016 |

OTHER PUBLICATIONS

Lydick et al., "Area under the curve: a metric for patient subjective responses in episodic diseases", Quality of Life Research, vol. 4, 1995, pp. 41-45.

Moriarty et al., "The intramolecular Asymmetric Pauson-Khand Cyclization as a Novel and General Stereoselective Route to Benzindene Prostacyclins: Synthesis of UT-15 (Treprostinil)", J. Org. Chem. 2004, vol. 69, pp. 1890-1902.

Sorbera et al., "UT-15, Treatment of Pulmonary Hypertension Treatment of Peripheral Vascular Disease," Drug of the Future, 2001 36(4), pp. 364-374.

Van Wijk et al., "Reliability and validity of a continuous pain registration procedure", European Journal of Pain, vol. 17, 1013, pp. 394-401.

Wuts et al., "Greene's Protective Groups in Organic Synthesis", Wiley-Interscience, ISBN 978-0-471-69754-1, 4th edition, 2007 (5 pages).

Figure 10A

| No. | Compound | Structure | MW |
|---|---|---|---|
| 1. | Cyclopentyl Carbamate of Treprostinil<br><br>Prodrug I | 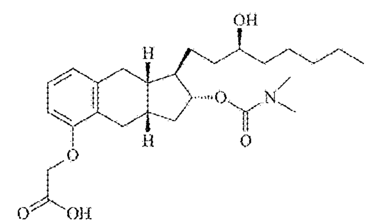 | 461.60 |
| 2. | Side Chain Carbamate of Treprostinil<br><br>Prodrug II | 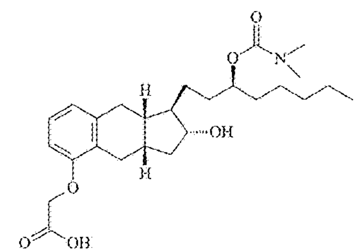 | 461.60 |
| 3. | Glycolamide of Treprostinil<br><br>Prodrug VII | 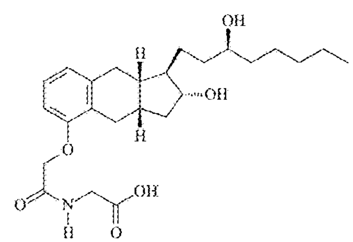 | 447.57 |
| 4. | Treprostinil acetoxy acetic acid prodrug<br><br>Prodrug XV | 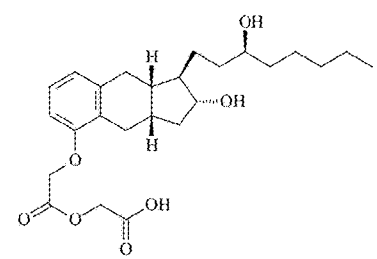 | 448.56 |

Figure 10B
| No. | Compound | Structure | MW |
|---|---|---|---|
| 5. | Cyclopentyl carbonate ester prodrug of treprostinil<br><br>Prodrug III | 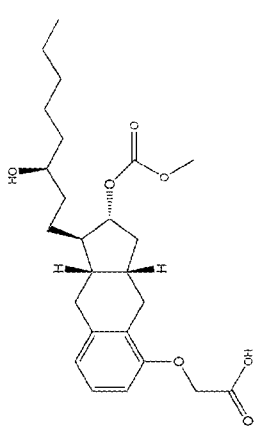 | 448.56 |
| 6. | Side chain carbonate ester prodrug of treprostinil<br><br>Prodrug IV | 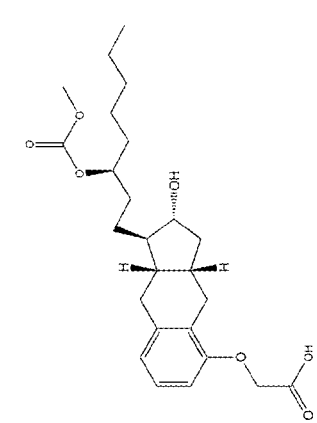 | 448.56 |
| 7. | Side chain N-methyl carbamate ester prodrug of treprostinil<br><br>Prodrug VIII | 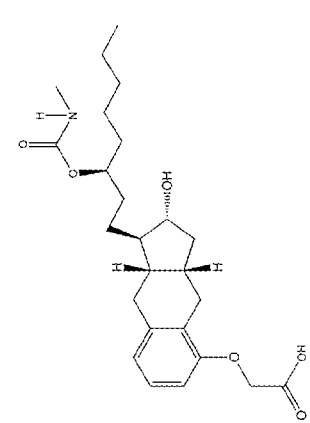 | 447.57 |

Figure 10C

| No. | Compound | Structure | MW |
|---|---|---|---|
| 8. | Treprostinil alanine amide prodrug<br><br>Prodrug X ) | 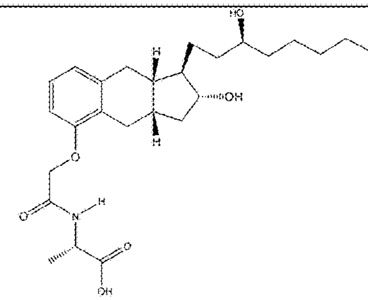 | 461.60 |
| 9. | Treprostinil valine amide prodrug<br><br>Prodrug XI ) | 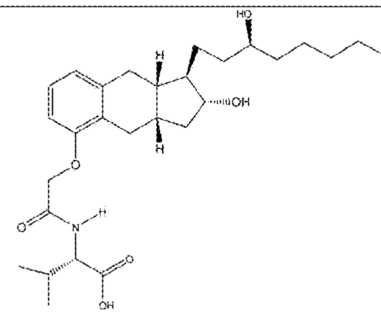 | 489.65 |
| 10. | Treprostinil aspartic acid amide prodrug<br><br>Prodrug XII | 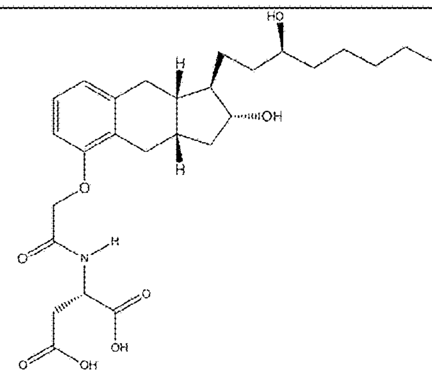 | 505.61 |

Figure 10D

| No. | Compound | Structure | MW |
|---|---|---|---|
| 11. | Treprostinil serine amide prodrug<br><br>Prodrug XIII | 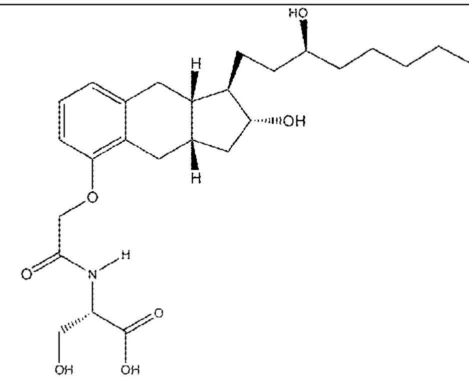 | 477.60 |
| 12. | Treprostinil sulfonamide prodrug<br><br>Prodrug XIV | 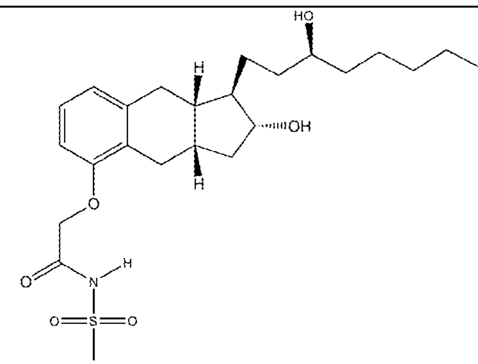 | 467.62 |

Figure 15

| Prodrug | Human Half-Life (min) | Human Half-Life (-NADPH) (min) | Dog Half-Life (min) | Dog Half-Life (-NADPH) (min) | Rat Half-Life (min) | Rat Half-Life (-NADPH) (min) | Cyno Half-Life (min) | Cyno Half-Life (-NADPH) (min) |
|---|---|---|---|---|---|---|---|---|
| III | 48.0 | 59.1 | 12.7 | 14.9 | 17.4 | 22.7 | 10.0 | 14.1 |
| IV | 10.3 | 10.8 | 10.0 | 12.3 | 8.65 | 16.4 | 4.90 | 9.00 |
| VII | 86.1 | >360 | >360 | >360 | 124 | >360 | 230 | >360 |
| VIII | >360 | >360 | >360 | >360 | 72.1 | >360 | | |
| X | >360 | >360 | >360 | >360 | 86.1 | >360 | | |
| XI | 231 | >360 | >360 | >360 | 59.0 | >360 | | |
| XII | >360 | >360 | >360 | >360 | >360 | >360 | | |
| XIII | >360 | >360 | >360 | >360 | 247 | >360 | | |
| XIV | 53.6 | 234 | >360 | >360 | 128 | 352 | 148 | >360 |

Mean Clinical score of cycle 1 (points).
*p<0.05 vs. PBS using one-way ANOVA followed by Tukey test.
Data bars represent mean ± SEM, N = 8.

Mean Clinical score of cycle 2 (points).
*p<0.05 vs. PBS using one-way ANOVA followed by Tukey test.
Data bars represent mean ± SEM, N = 8.

*Note: Thermal test was performed immediately post Von Frey test (up to 10 minutes difference).

Von Frey Response test (g).
**** p<0.0001 vs. Phosphate Buffer using one-way ANOVA followed by Tukey test.
*** p<0.001 vs. Phosphate Buffer using one-way ANOVA followed by Tukey test.
Data bars represent mean ± SEM, N=8.

Thermal Response test (sec).

**** p<0.0001 vs. Phosphate Buffer using one-way ANOVA followed by Tukey test.
*** p<0.001 vs. Phosphate Buffer using one-way ANOVA followed by Tukey test.
** p<0.01 vs. Phosphate Buffer using one-way ANOVA followed by Tukey test.
* p<0.05 vs. Phosphate Buffer using one-way ANOVA followed by Tukey test.

Data bars represent mean ± SEM, N=8.

Mean Clinical score (points).
\*\*\*\* p<0.0001 vs. Phosphate Buffer using one-way ANOVA followed by Tukey test.
Data bars represent mean ± SEM, N=8.

* $p<0.01$ vs. PBS using one-way ANOVA followed by Tukey test.
** $p<0.001$ vs. PBS using one-way ANOVA followed by Tukey test.
**** $p<0.0001$ vs. PBS using one-way ANOVA followed by Tukey test.

TREPROSTINIL PRODRUGS

RELATED APPLICATIONS

The present application is a Continuation of U.S. application Ser. No. 15/716,007, filed Sep. 26, 2017, which claims priority to U.S. provisional application No. 62/399,737 filed Sep. 26, 2016, which is incorporated herein by reference in its entirety.

FIELD

The present application generally relates to prostacyclins and more particularly, to prodrugs of treprostinil and to methods of making and using such prodrugs.

BACKGROUND

Pulmonary hypertension is a progressive and life-threatening disease characterized by increased pressure in the pulmonary vasculature that can lead to, inter alia, heart failure.

Pulmonary hypertension (PH) has been previously classified as primary (idiopathic) or secondary. The World Health Organization (WHO) has classified pulmonary hypertension into five groups:

Group 1: pulmonary arterial hypertension (PAH);
Group 1': Pulmonary veno-occlusive disease (PVOD) and/or pulmonary capillary haemangiomatosis (PCH)
Group 2: PH with left heart disease;
Group 3: PH with lung disease and/or hypoxemia;
Group 4: PH due to chronic thrombotic and/or embolic disease; and
Group 5: miscellaneous conditions; unclear multifactorial mechanisms (e.g., sarcoidosis, histiocytosis X, lymphangiomatosis and compression of pulmonary vessels).

There are currently a number of approved products for certain types of pulmonary hypertension, including Group 1 (PAH). Those products include products containing treprostinil as the active ingredient, such as Remodulin® treprostinil injection. Treprostinil, however, is sometimes associated with site pain when administered subcutaneously. Thus, a need exists for administering treprostinil without causing site pain.

SUMMARY

One embodiment is a method of treating a disease or condition, comprising selecting a patient, who is suffering from the disease or condition and who has experienced site pain upon subcutaneous administration of treprostinil or a pharmaceutically salt thereof and administering subcutaneously to the patient an effective amount of a prodrug of treprostinil, wherein the disease or condition is one or more disease or condition selected from the group consisting of pulmonary hypertension, congestive heart failure, peripheral vascular disease, Raynaud's phenomenon, Scleroderma, renal insufficiency, peripheral neuropathy, digital ulcers, intermittent claudication, ischemic limb disease, peripheral ischemic lesions, pulmonary fibrosis and asthma.

Another embodiment is a method of treating pulmonary hypertension comprising administering subcutaneously to a patient suffering from pulmonary hypertension an effective amount of a prodrug of treprostinil.

Yet another embodiment is a compound or a pharmaceutically acceptable salt thereof, wherein the compound having one of the following formulas:

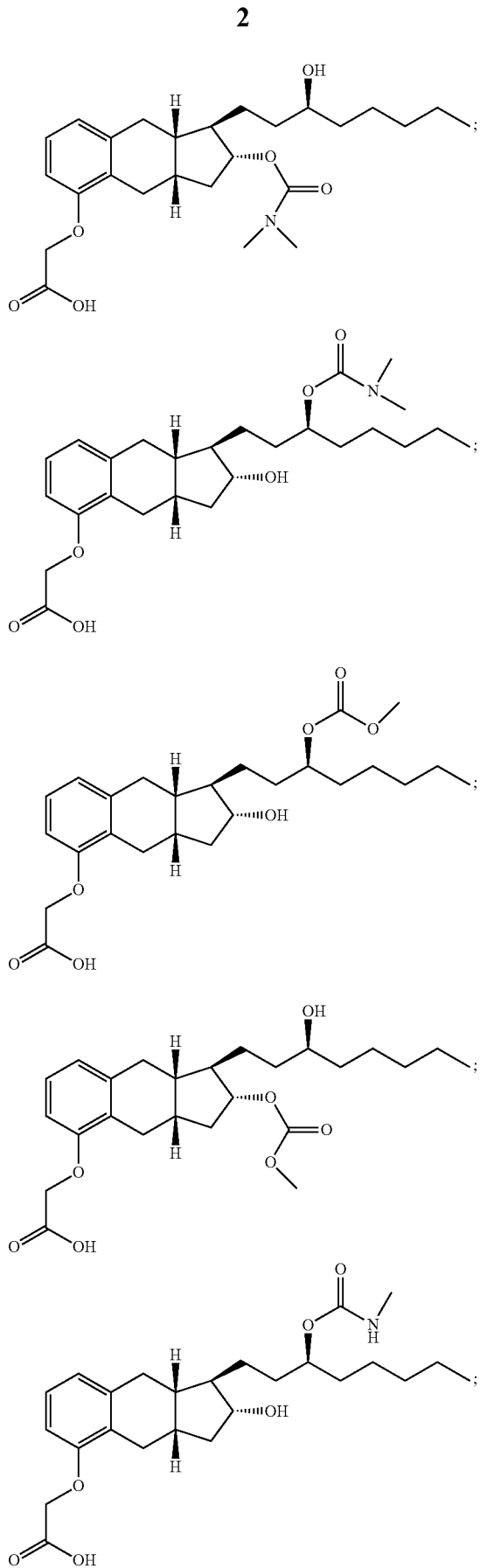

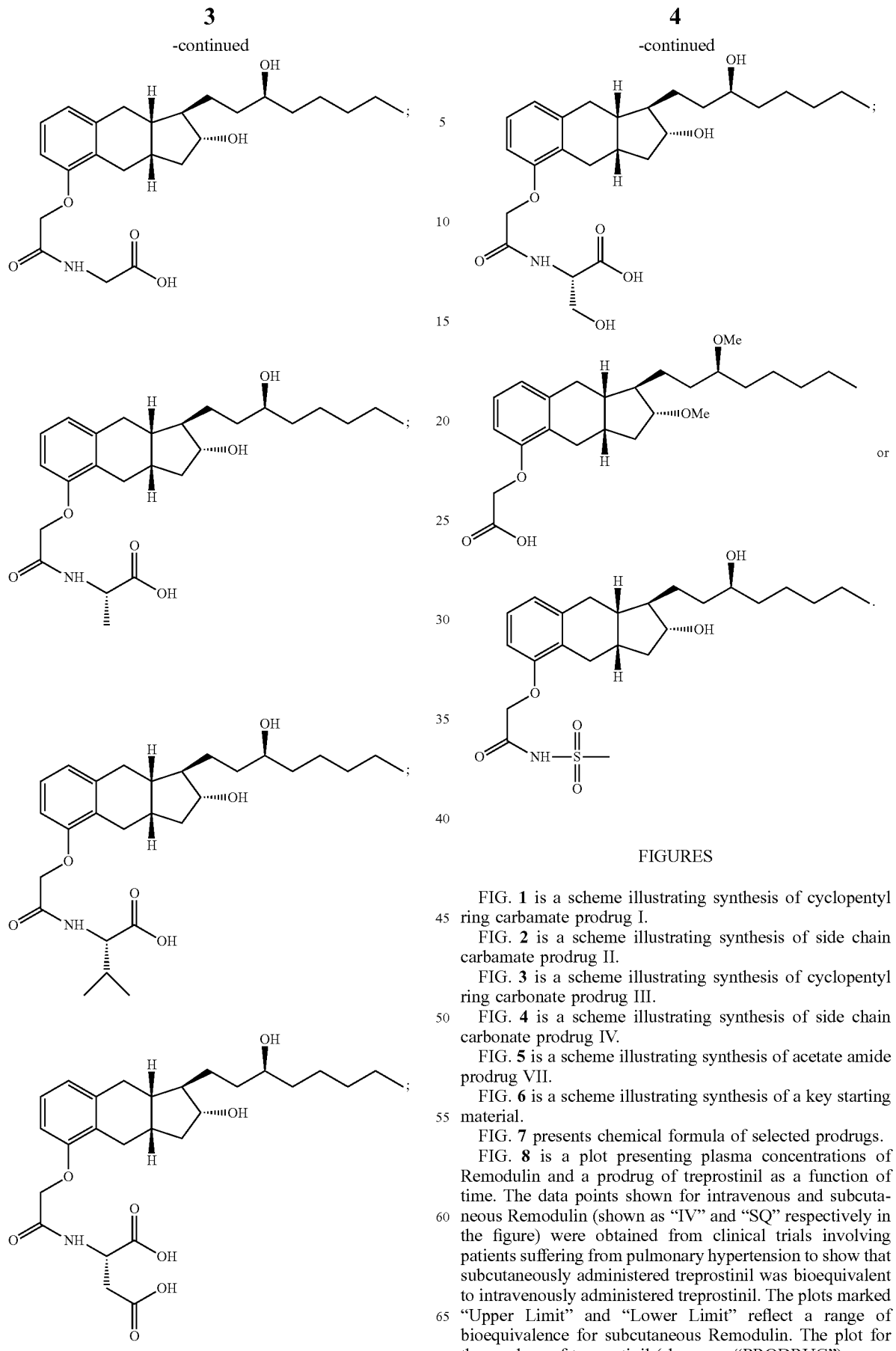

FIGURES

Figure 7:
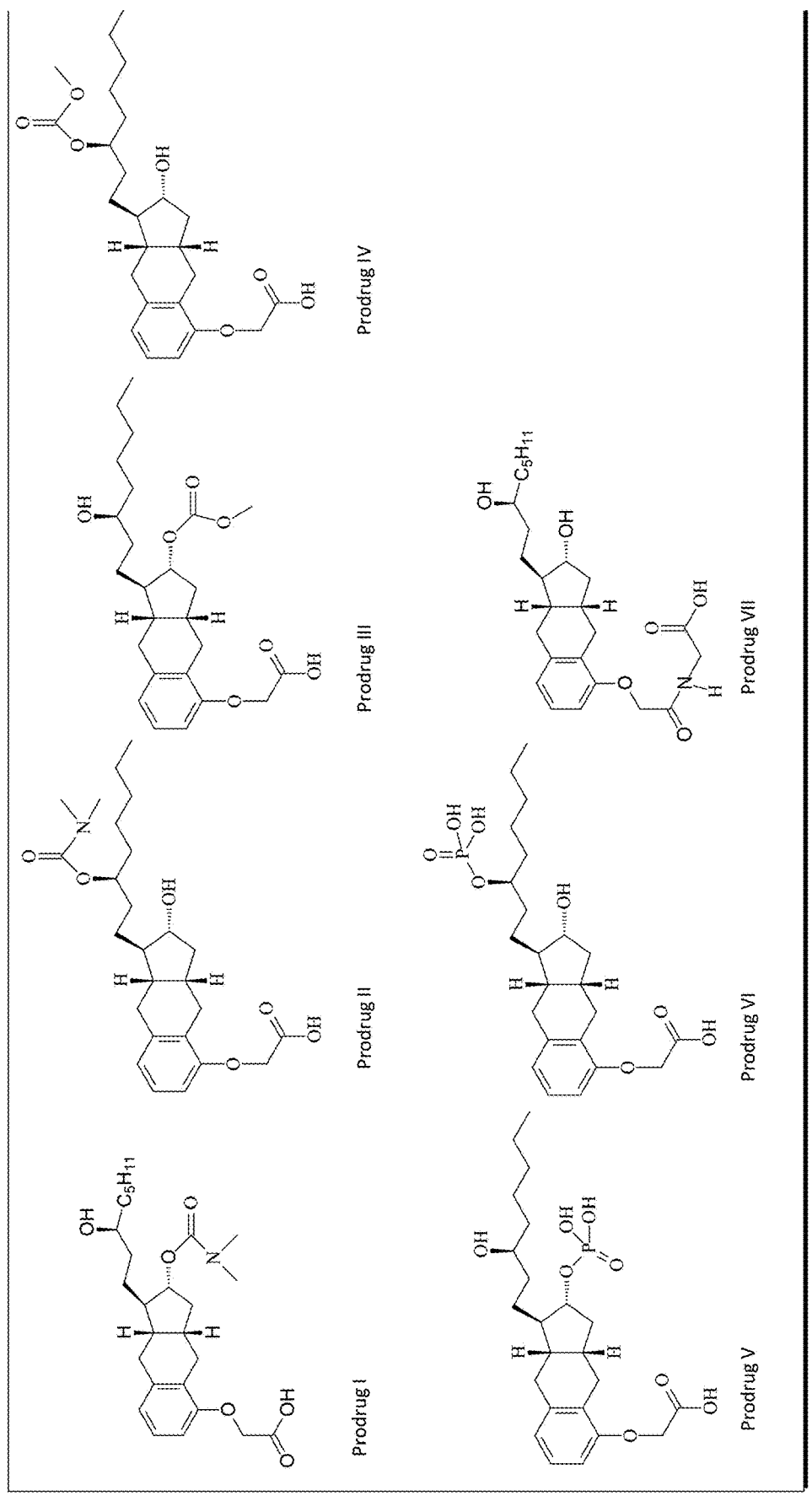

FIG. 7 presents chemical formula of selected prodrugs.

Figure 8:
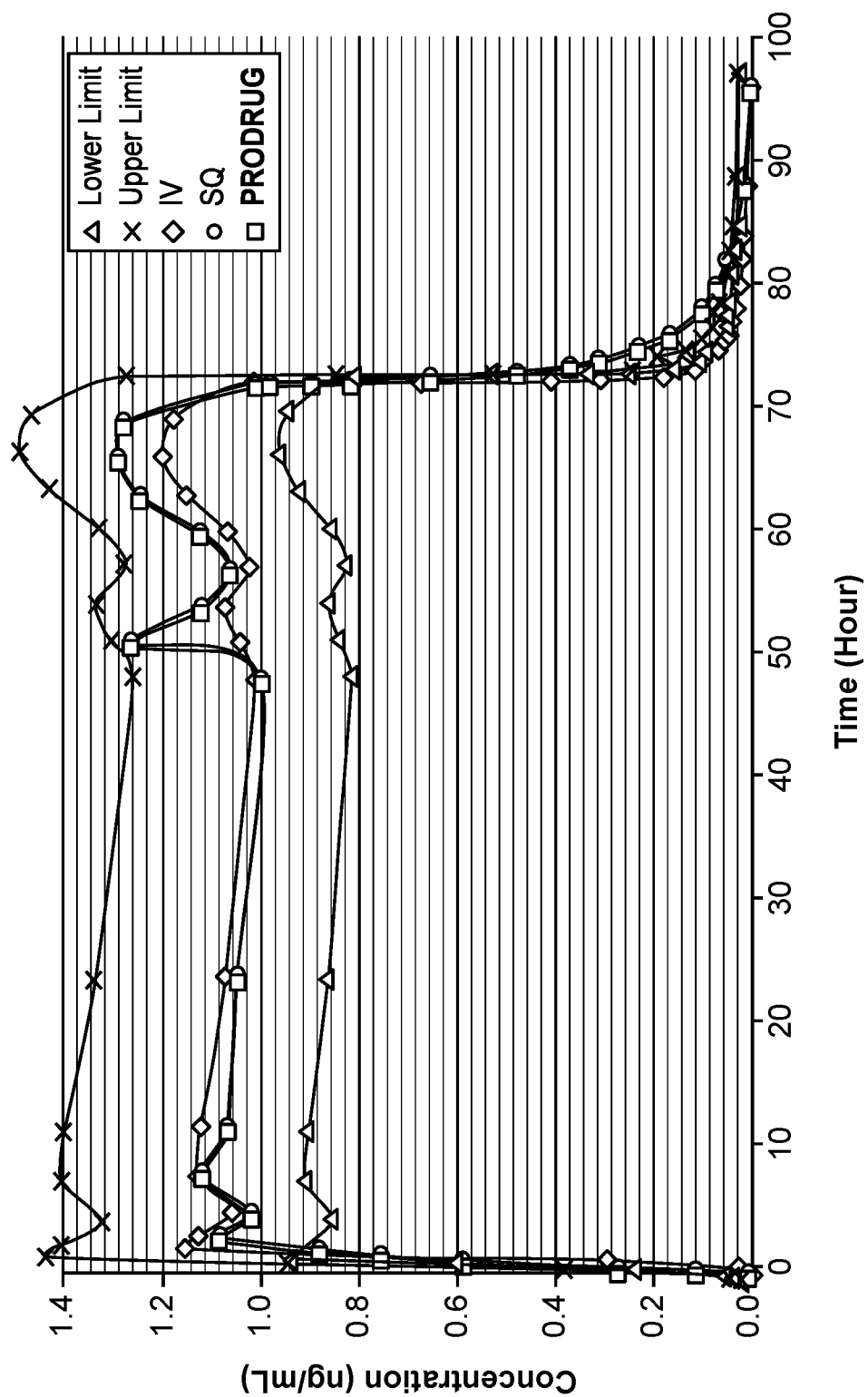

FIG. 8 is a plot presenting plasma concentrations of Remodulin and a prodrug of treprostinil as a function of time. The data points shown for intravenous and subcutaneous Remodulin (shown as "IV" and "SQ" respectively in the figure) were obtained from clinical trials involving patients suffering from pulmonary hypertension to show that subcutaneously administered treprostinil was bioequivalent to intravenously administered treprostinil. The plots marked "Upper Limit" and "Lower Limit" reflect a range of bioequivalence for subcutaneous Remodulin. The plot for the prodrug of treprostinil (shown as "PRODRUG") represents one possible set of data points that would approximate the plot of subcutaneously administered Remodulin, where the prodrug has been converted in vivo to treprostinil free acid, and the amount of free acid treprostinil in plasma is plotted.

Figure 9:
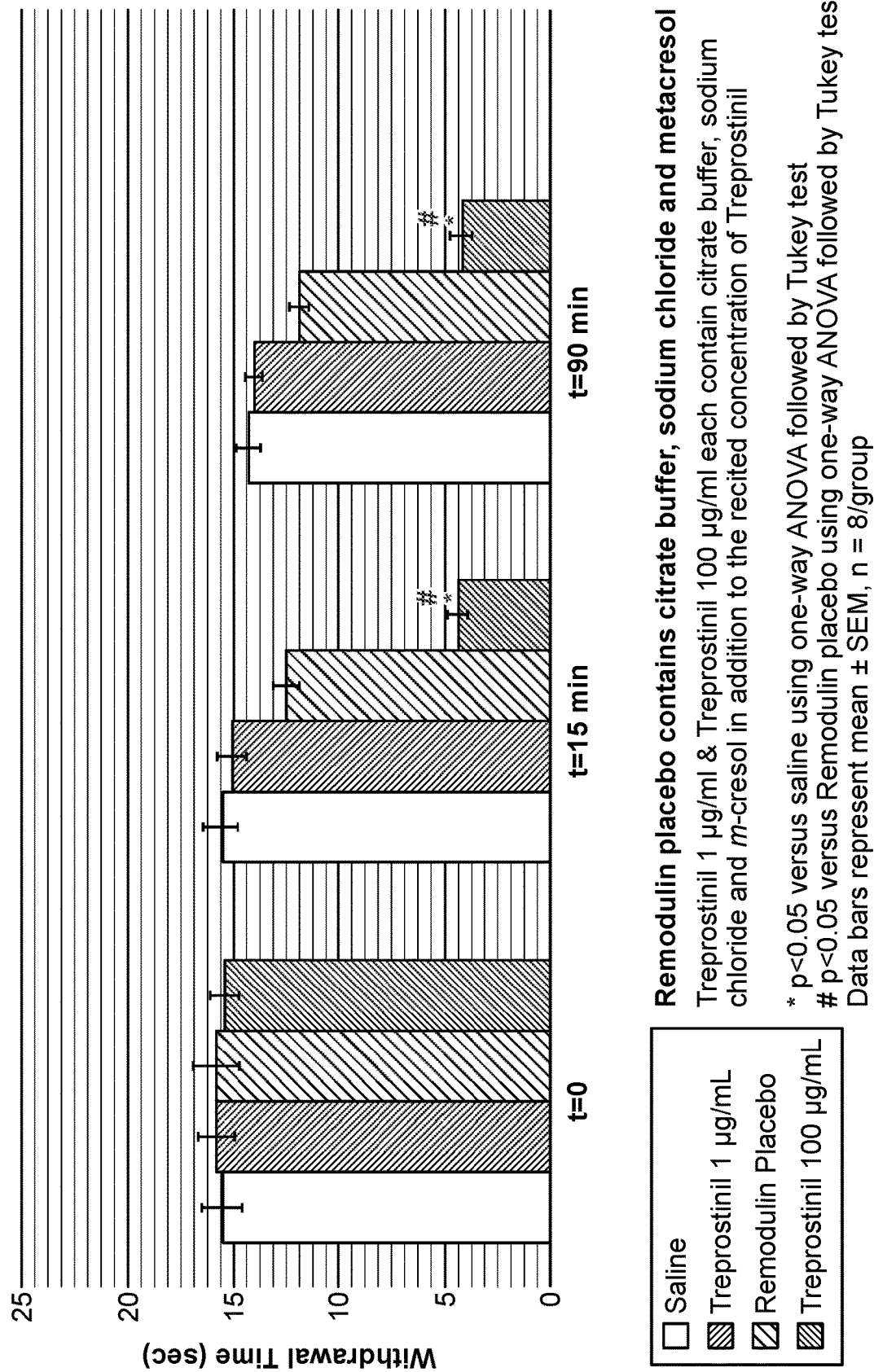

FIG. 9 reports withdrawal time due to site pain in tested rats, which were administered one of the following: a) saline, b) a (Remodulin) placebo formulation, which contained citrate buffer, sodium chloride and m-cresol, while not containing treprostinil; c) a first Remodulin formulation with a treprostinil concentration of 1 µg/mL, where the formulation contained treprostinil, citrate buffer, sodium chloride and m-cresol; d) a second Remodulin formulation with a treprostinil concentration of 100 µg/mL, where the formulation contained treprostinil, citrate buffer, sodium chloride and m-cresol, with the vertical bars showing how quickly the tested rat withdrew its paw in response to a heat stimulus following administration of the formulations at t=0, 15 min and 90 min.

FIG. 10A-D show selected prodrugs.

Figure 11:
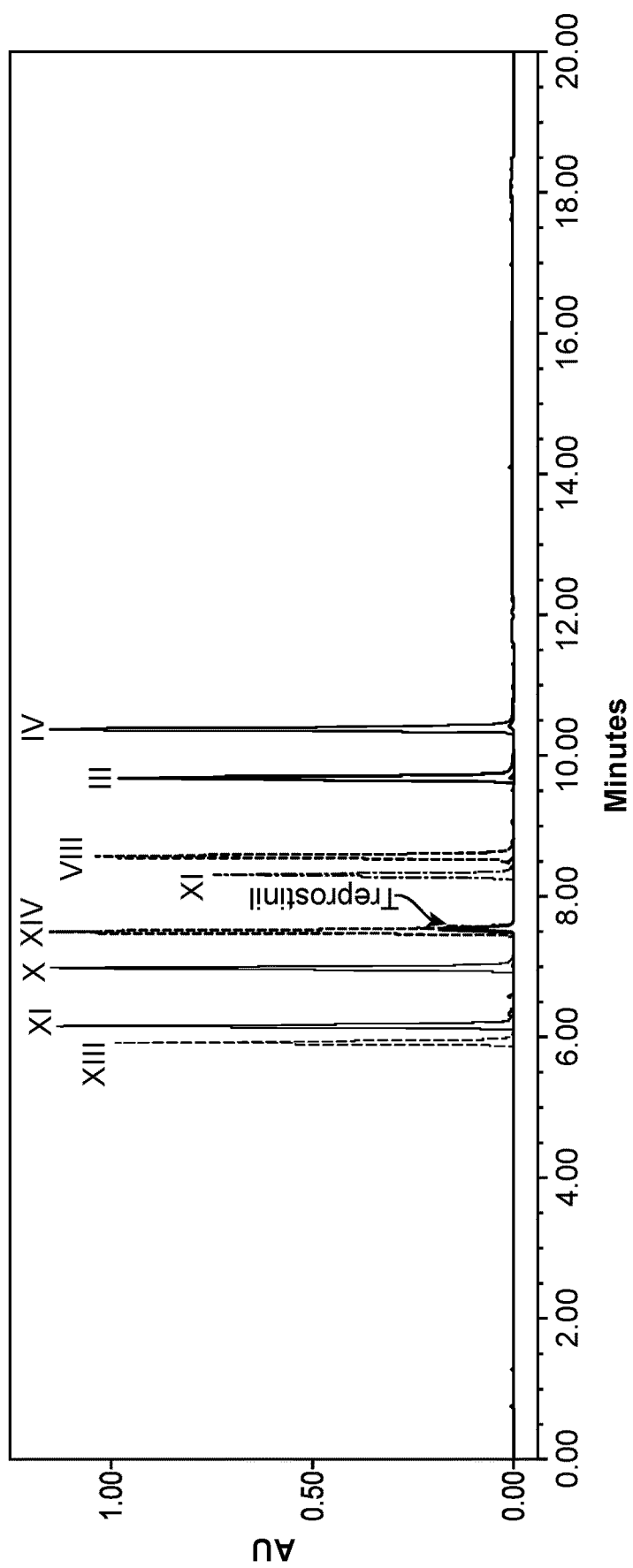

FIG. 11 shows chromatographic overlay of treprostinil and eight selected prodrugs using ACE Excel 2 C18 column. The results of the specificity study indicate that treprostinil is well separated from all prodrugs except Prodrug XIV which co-elutes.

Figure 12:
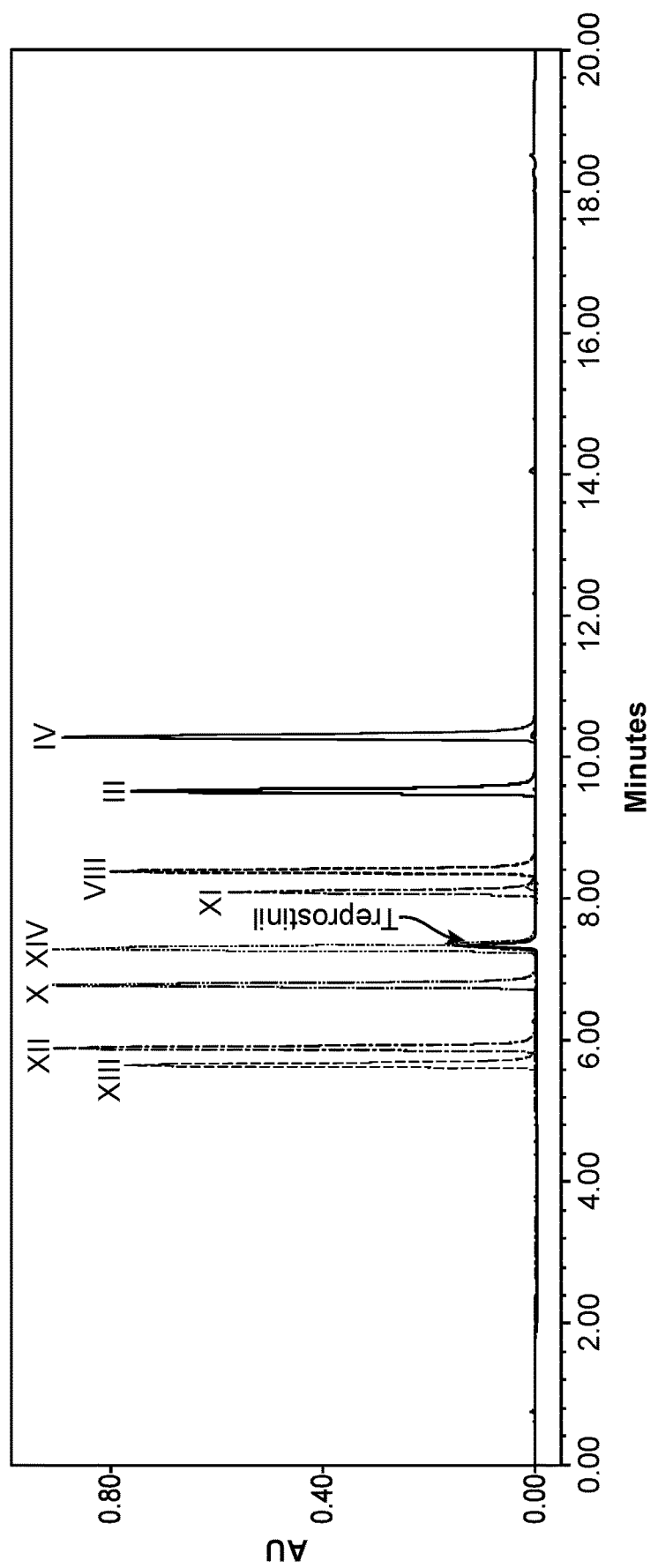

FIG. 12 shows chromatographic overlay of treprostinil and eight selected prodrugs using Waters BEH C18 column.

Figure 13:
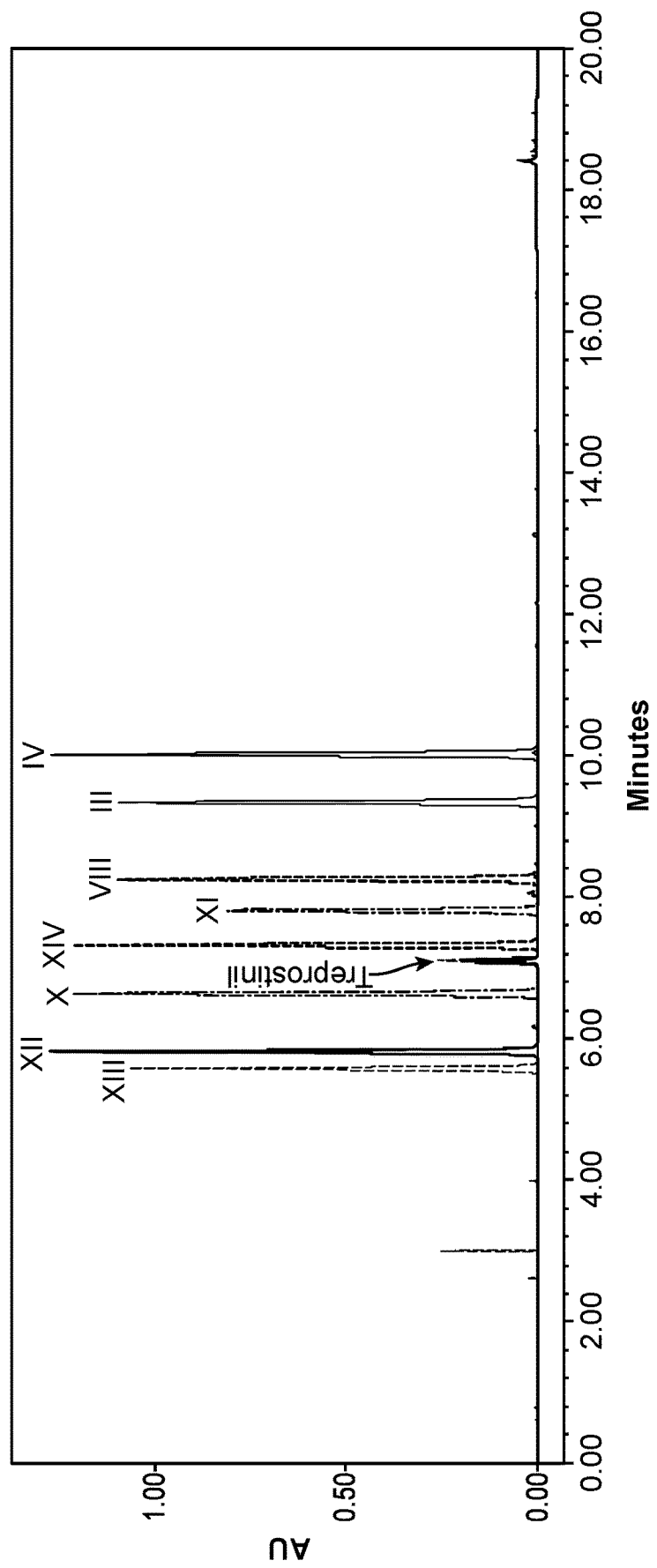

FIG. 13 shows chromatographic overlay of treprostinil and eight selected prodrugs using ACE Excel 2 C18-AR column (C18-Phenyl phase).

Figure 14:
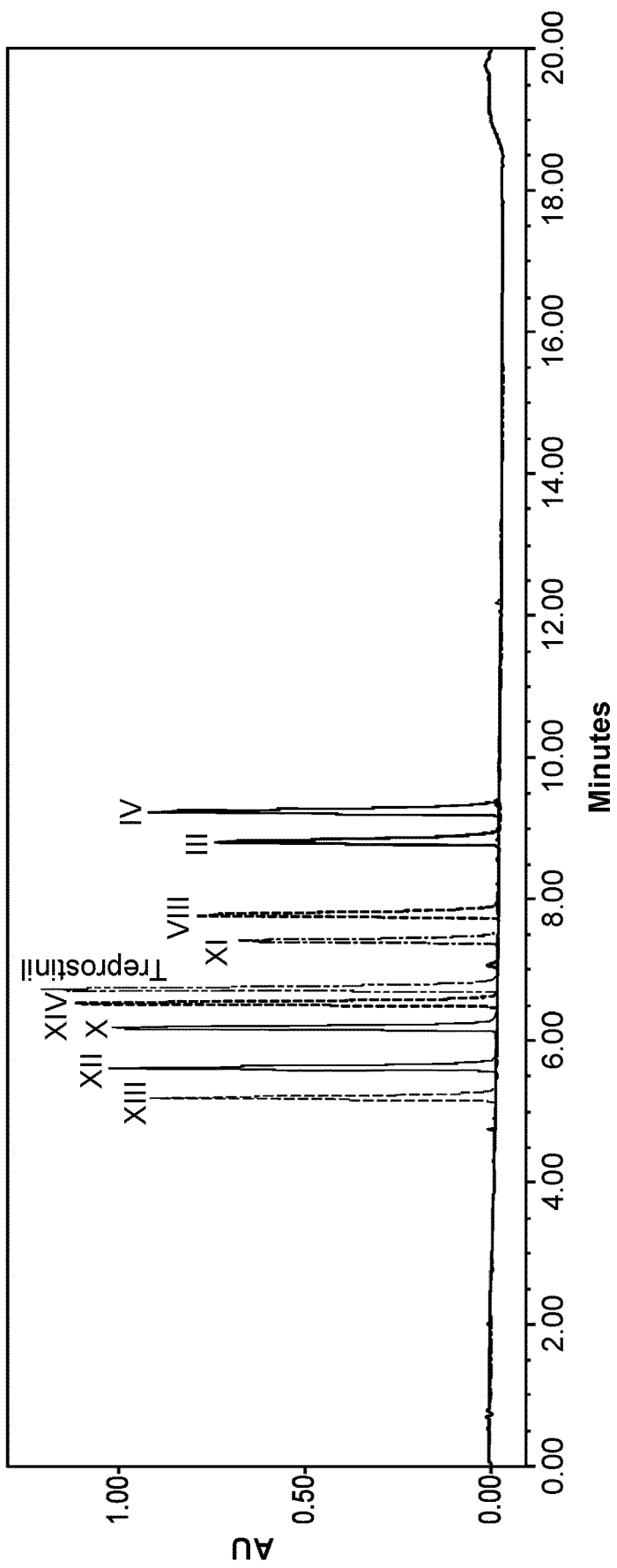

FIG. 14 shows chromatographic overlay of treprostinil and eight selected prodrugs using Waters CSH Phenyl Hexyl column.

FIG. 15 summarizes half-live values for selected prodrugs.

Figure 16:
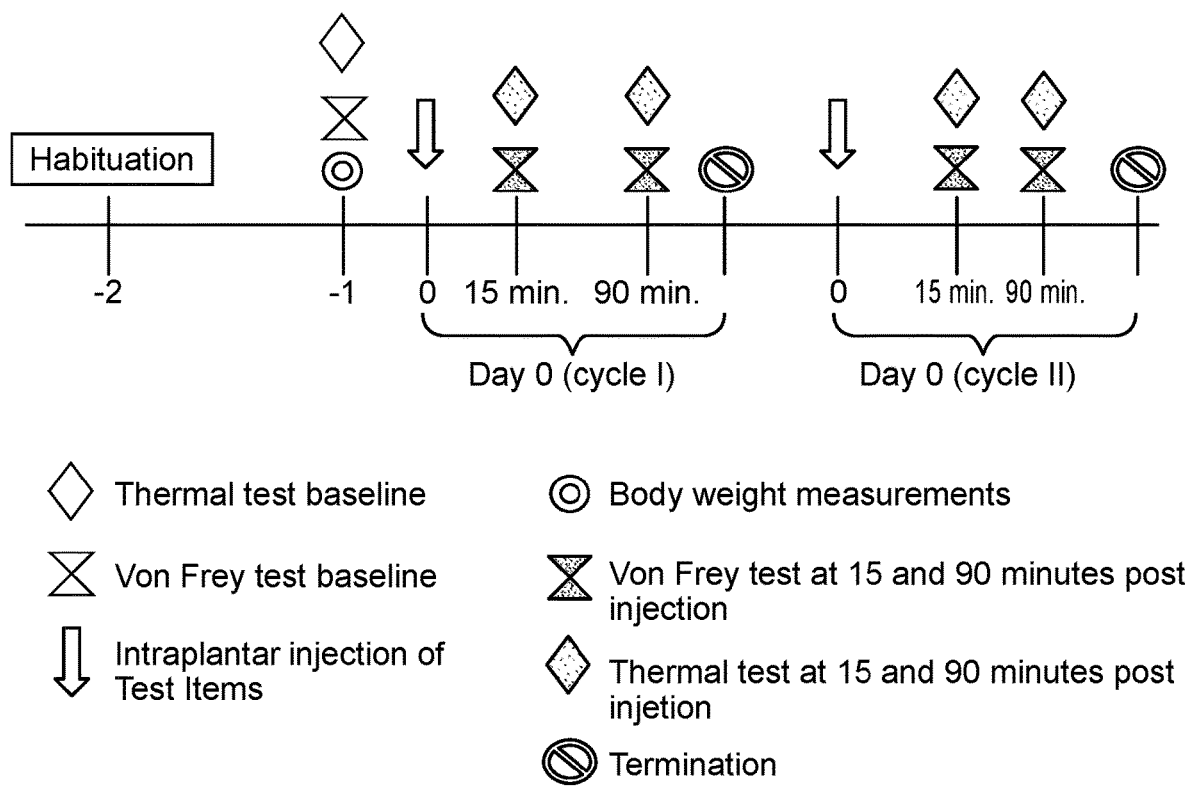

FIG. 16 is a schematic depiction of intraplantar model induction and treatment used in Examples 9 and 11. Thermal test was performed immediately post Von Frey test (up to 10 minutes difference).

Figure 17:
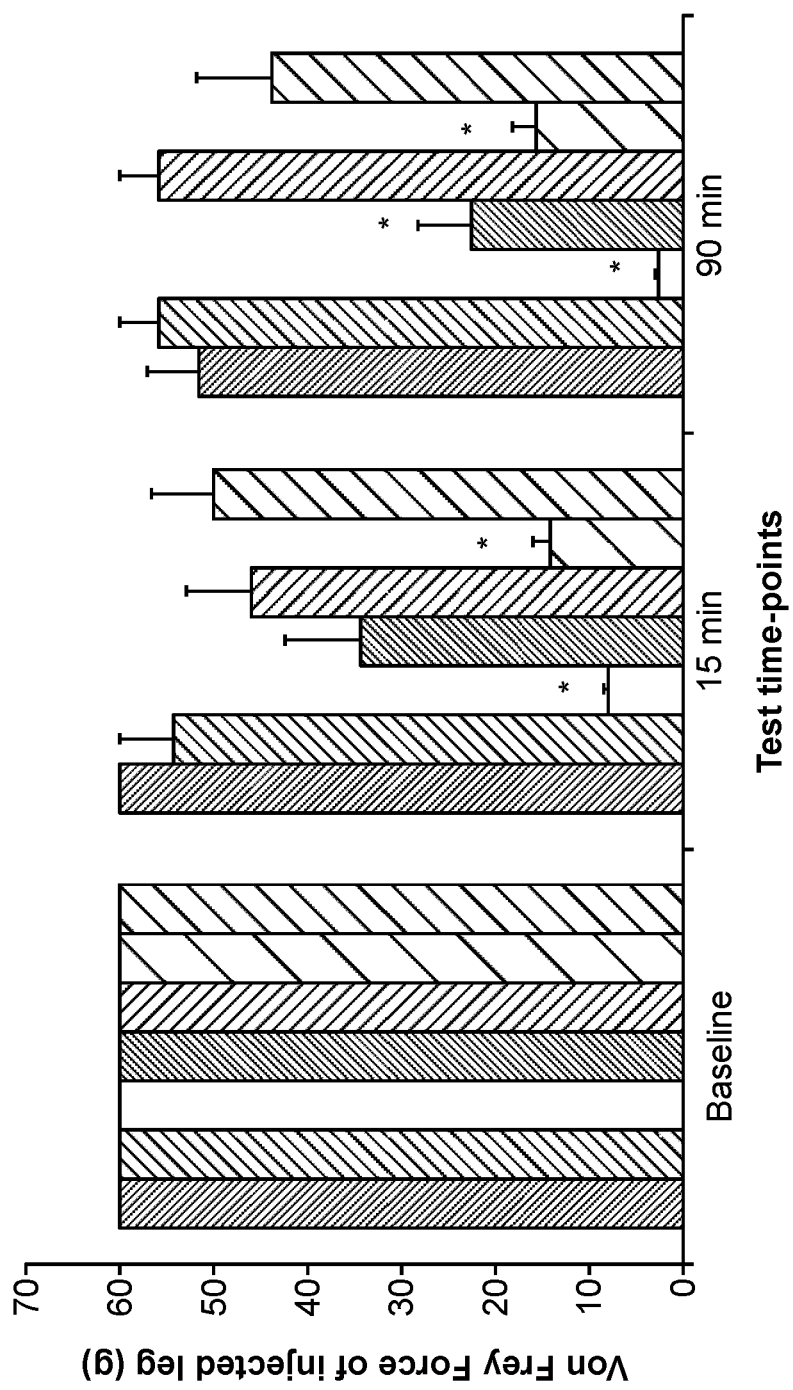

FIG. 17 presents results for Von Frey Response test of cycle 1 (g). Lower force indicates greater sensitivity. For each of baseline, 15 min and 90 min test points, columns represent the following left to right: Saline (Group 1), PBS (Group 2), treprostinil 100 µg/ml (Group 3), Prodrug I 100 µg/ml (Group 4), Prodrug II 100 µg/ml (Group 5), Prodrug VII 100 µg/ml (Group 6), Prodrug VIII 100 µg/ml (Group 7).

Figure 18:
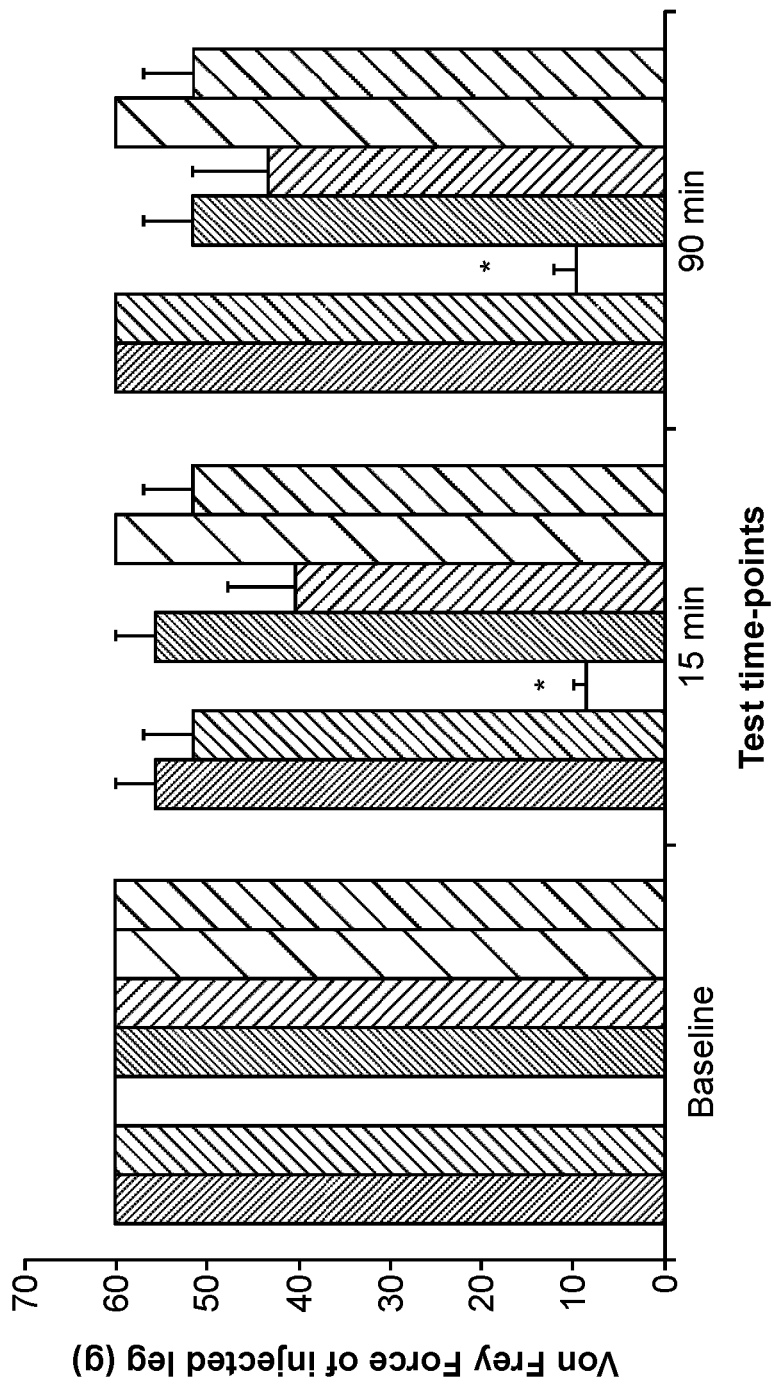

FIG. 18 presents results for Von Frey Response test of cycle 2 (g). Lower force indicates greater sensitivity. For each of baseline, 15 min and 90 min test time-points, columns represent the following left to right: Saline (Group 8), PBS (Group 9), treprostinil 1 µg/ml (Group 10), Prodrug I 1 µg/ml (Group 11), Prodrug II 1 µg/ml (Group 12), Prodrug VII 1 µg/ml (Group 13), Prodrug VIII 1 µg/ml (Group 14).

Figure 19:
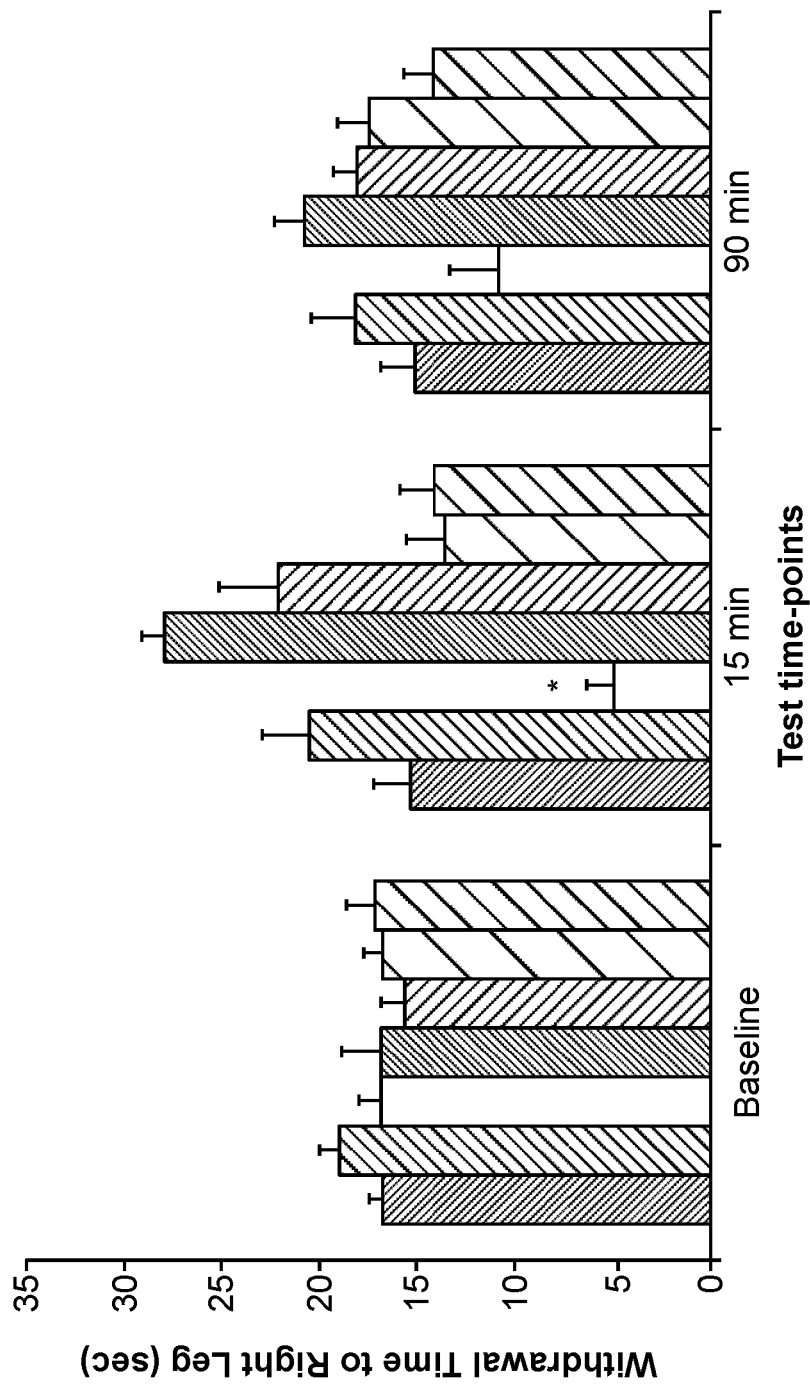

FIG. 19 presents results for Thermal Response test of cycle 1 (sec). Lower/faster time indicates greater sensitivity. For each of baseline, 15 min and 90 min test time-points, columns represent the following left to right: Saline (Group 1), PBS (Group 2), treprostinil 100 µg/ml (Group 3), Prodrug I 100 µg/ml (Group 4), Prodrug II 100 µg/ml (Group 5), Prodrug VII 100 µg/ml (Group 6), Prodrug VIII 100 µg/ml (Group 7).

Figure 20:
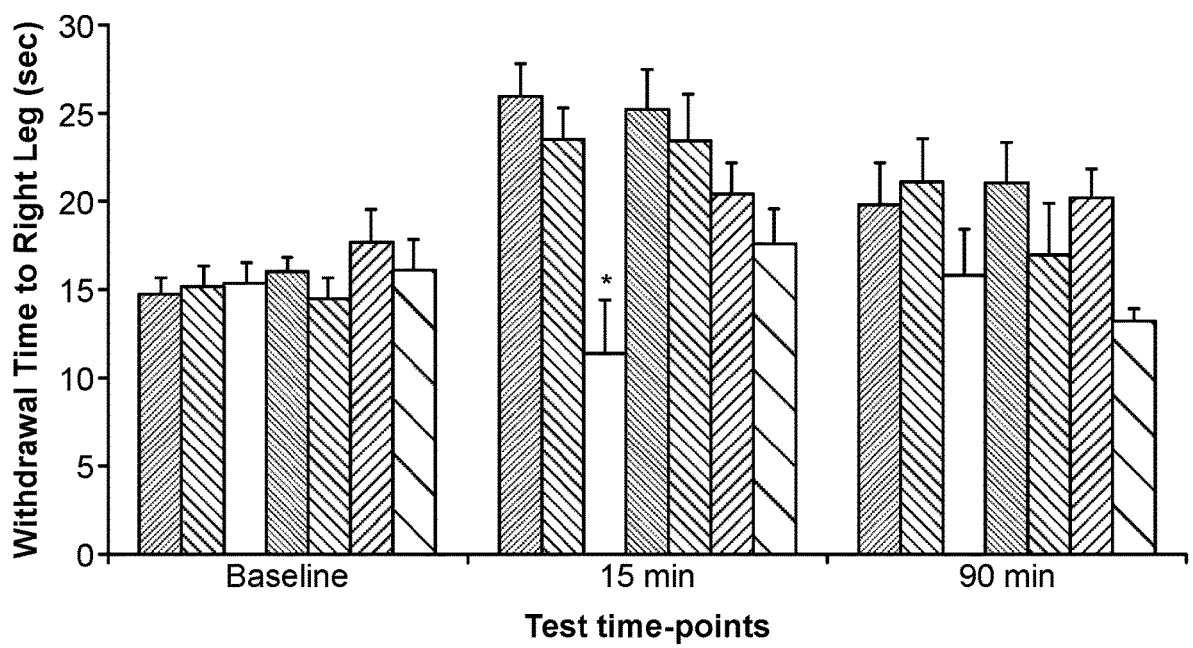

FIG. 20 presents results for Thermal Response test of cycle 2 (sec). Lower/faster time indicates greater sensitivity. For each of Baseline, 15 min and 90 min test time-points, columns represent the following left to right: Saline (Group 8), PBS (Group 9), treprostinil 1 µg/ml (Group 10), Prodrug I 1 µg/ml (Group 11), Prodrug II 1 µg/ml (Group 12), Prodrug VII 1 µg/ml (Group 13), Prodrug VIII 1 µg/ml (Group 14).

Figure 21:
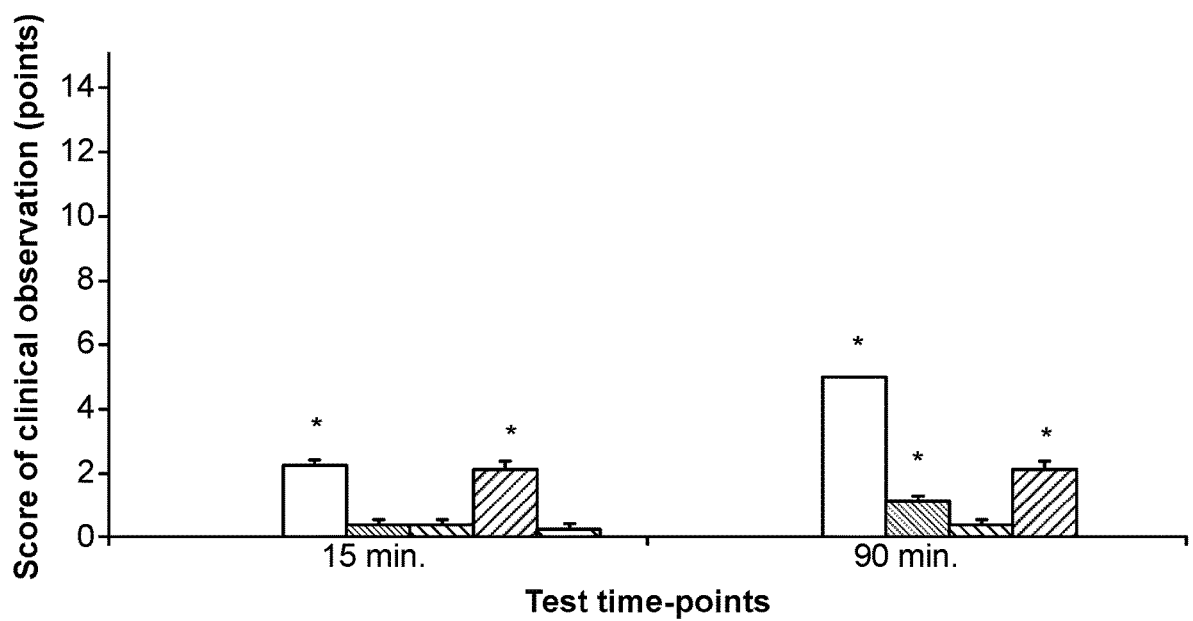

FIG. 21 presents mean clinical score of cycle 1 (points). Increased/Higher score indicates more observations of adverse events. For each of 15 min and 90 min test time-points, data presented the following left to right: Saline (Group 1), PBS (Group 2), treprostinil 100 µg/ml (Group 3), Prodrug I 100 µg/ml (Group 4), Prodrug II 100 µg/ml (Group 5), Prodrug VII 100 µg/ml (Group 6), Prodrug VIII 100 µg/ml (Group 7). For the 15 min time point, non-zero observations are as follows left to right: treprostinil 100 µg/ml (Group 3), Prodrug I 100 µg/ml (Group 4), Prodrug II 100 µg/ml (Group 5), Prodrug VII 100 µg/ml (Group 6), Prodrug VIII 100 µg/ml (Group 7). For the 90 min time point, non-zero observations are as follows left to right: treprostinil 100 µg/ml (Group 3), Prodrug I 100 µg/ml (Group 4), Prodrug II 100 µg/ml (Group 5), Prodrug VII 100 µg/ml (Group 6).

Figure 22:
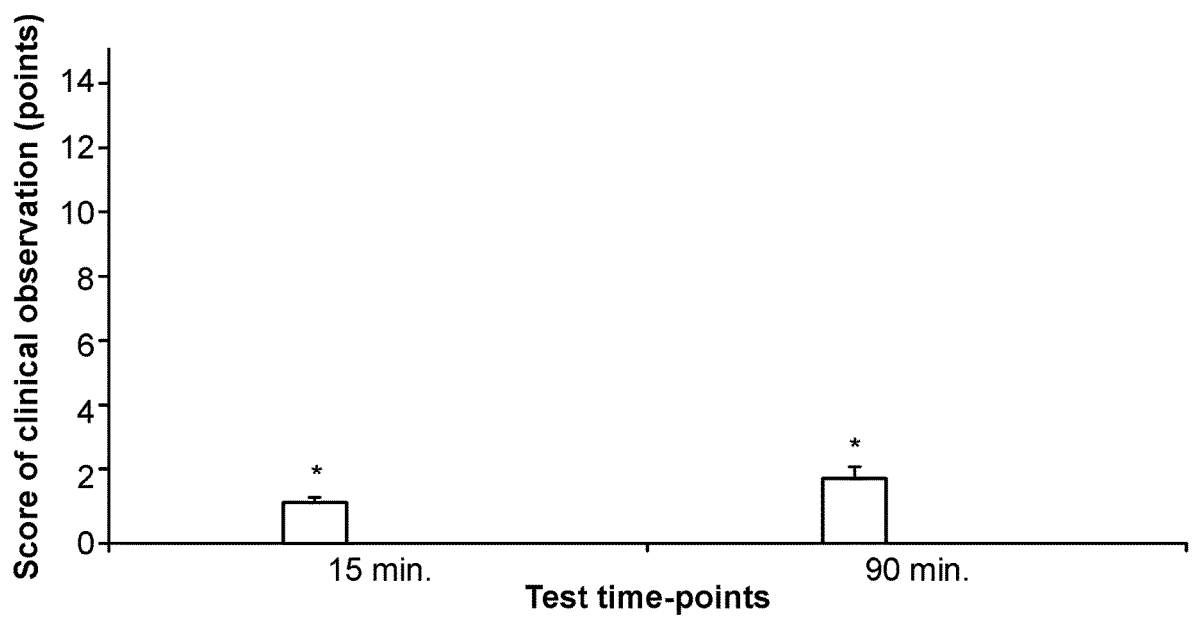

FIG. 22 presents mean clinical score of cycle 2 (points). Increased/Higher score indicates more observations of adverse events. For each of 15 min and 90 min test time-points, data presented the following left to right: Saline (Group 8), PBS (Group 9), treprostinil 1 µg/ml (Group 10), Prodrug I 1 µg/ml (Group 11), Prodrug II 1 µg/ml (Group 12), Prodrug VII 1 µg/ml (Group 13), Prodrug VIII 1 µg/ml (Group 14). For each of 15 min and 90 min test time-points, the only non-zero observations correspond to Treprostinil 1 µg/ml (Group 10).

Figure 23:
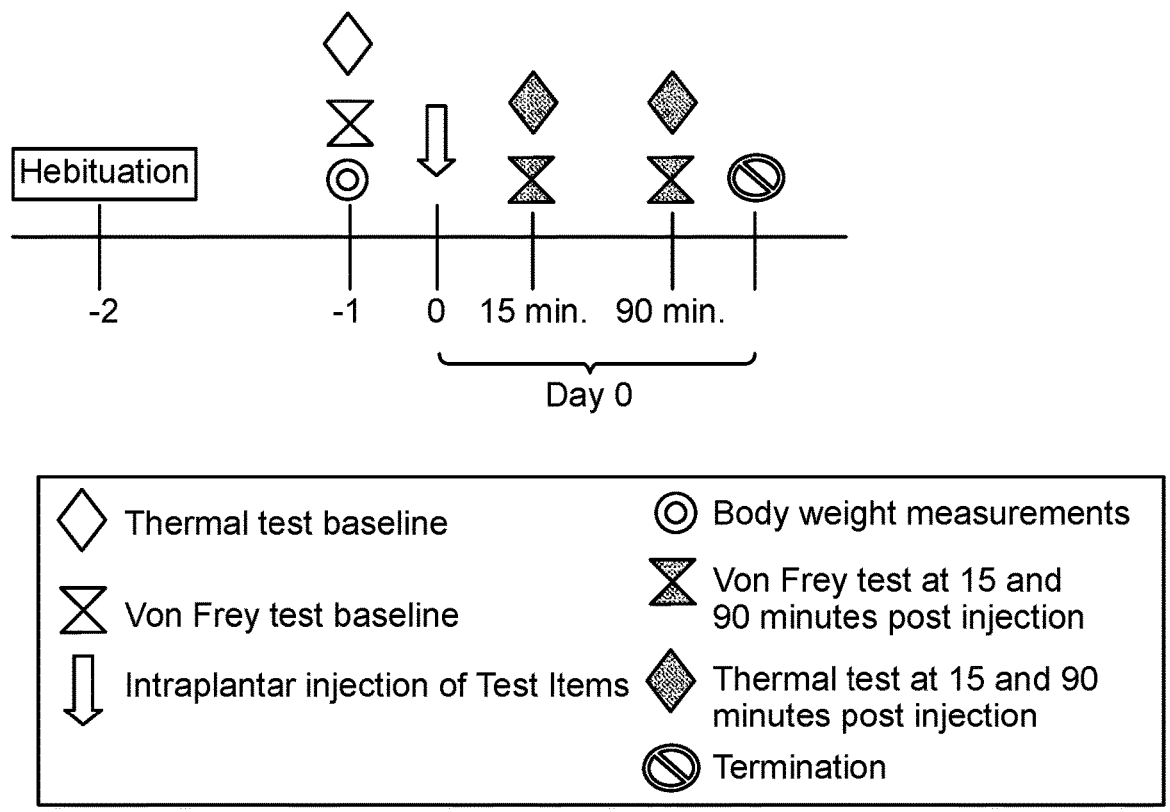

FIG. 23 is a schematic depiction of intraplantar model induction and treatment used in Example 10.

Figure 24:
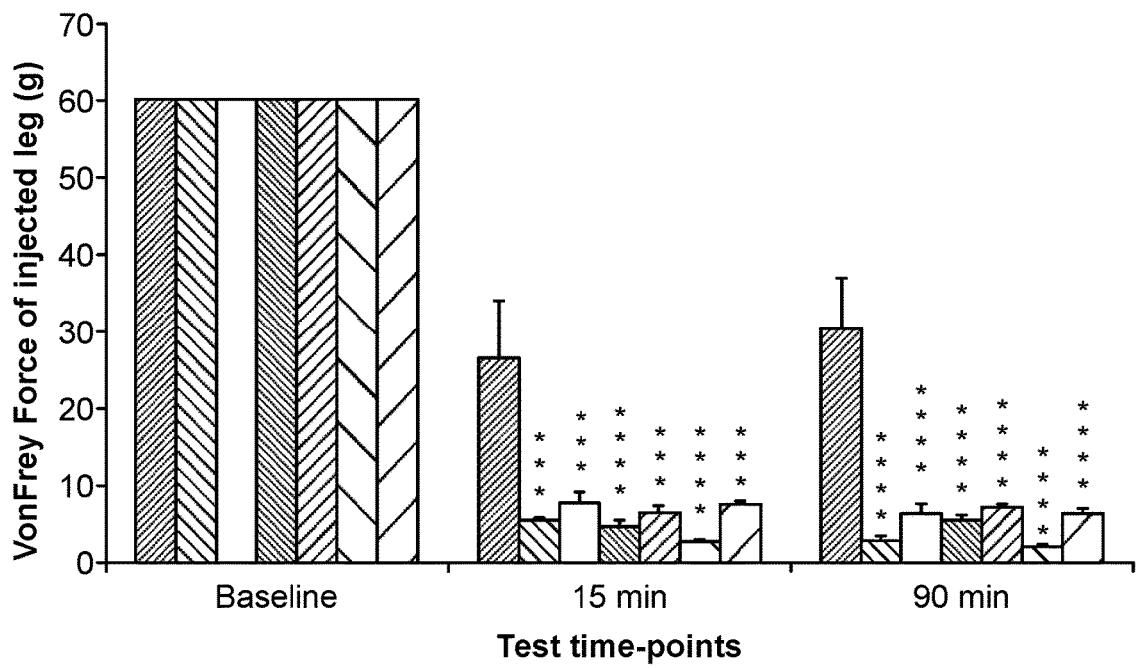

FIG. 24 presents results for Von Frey Response test (g). Lower force indicated greater sensitivity. For each of Baseline, 15 min and 90 min test points, columns represent the following left to right: Phosphate Buffer (Group 1), treprostinil 100 µg/ml (Group 2), treprostinil 1 µg/ml (Group 3), PRODRUG VII 100 µg/ml (Group 4), PRODRUG VII 1 µg/ml (Group 5), Prodrug XV 100 µg/ml (Group 6), Prodrug XV 1 µg/ml (Group 7).

Figure 25:
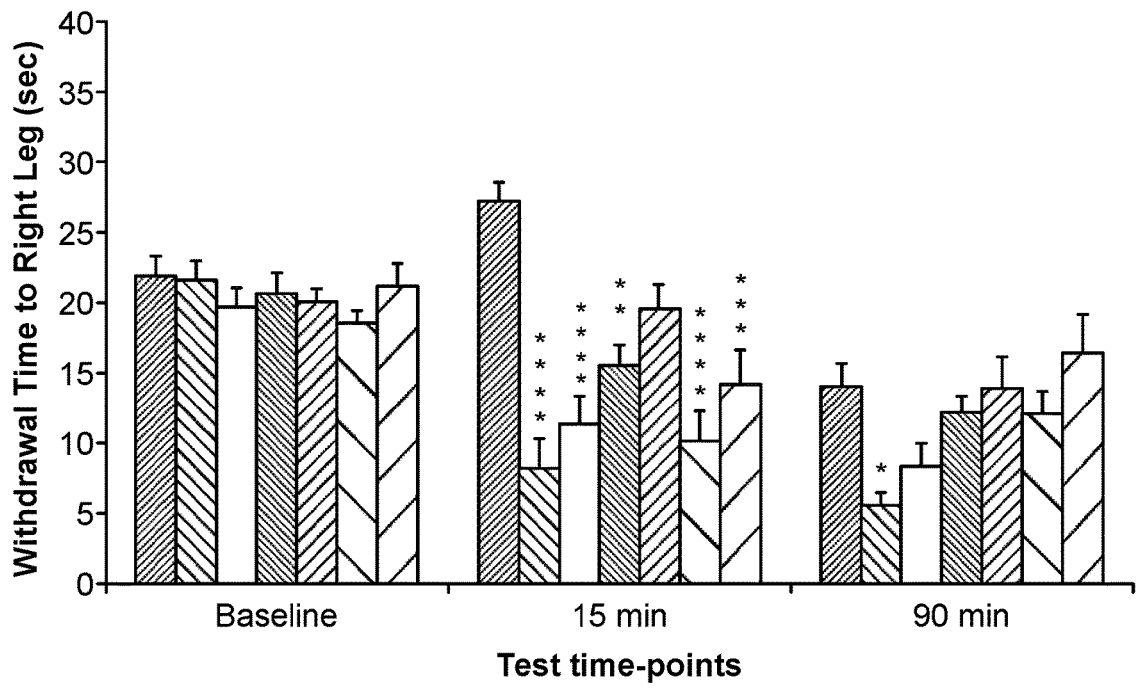

FIG. 25 presents results for Thermal Response test (sec). Lower/faster time indicates greater sensitivity. For each of Baseline, 15 min and 90 min test points, columns represent the following left to right: Phosphate Buffer (Group 1), treprostinil 100 µg/ml (Group 2), treprostinil 1 µg/ml (Group 3), Prodrug VII 100 µg/ml (Group 4), Prodrug VII 1 µg/ml (Group 5), Prodrug XV 100 µg/ml (Group 6), Prodrug XV 1 µg/ml (Group 7).

Figure 26:
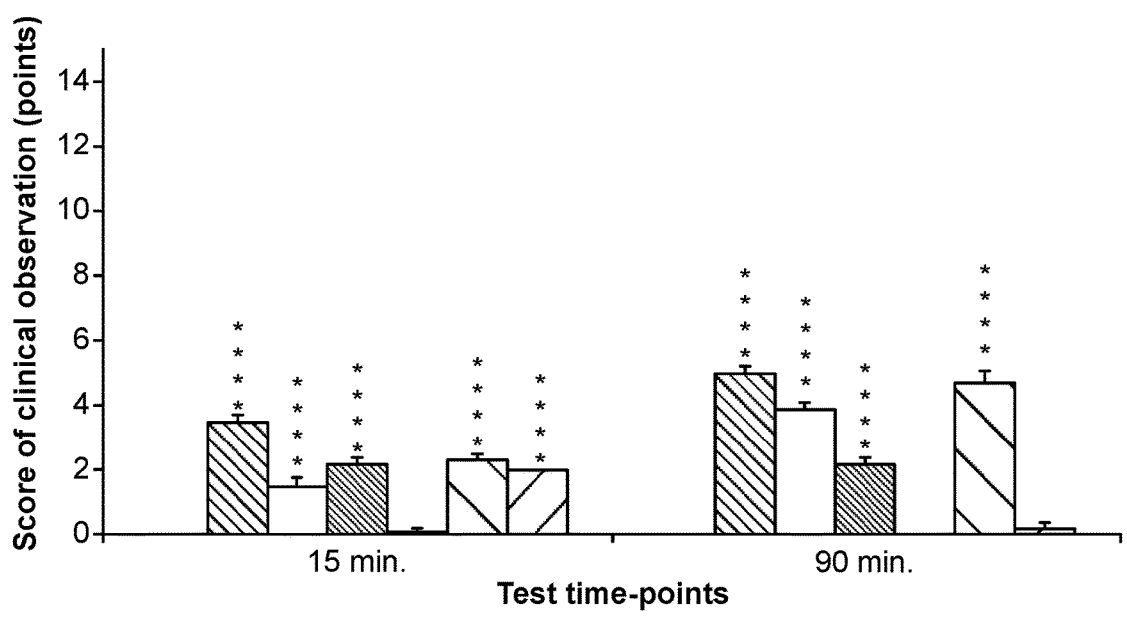

FIG. 26 presents mean clinical score of cycle 1 (points). Increased/Higher score indicates more observations of adverse events. For each of 15 min and 90 min test time-points, data presented the following left to right: Phosphate Buffer (Group 1), treprostinil 100 µg/ml (Group 2), treprostinil 1 µg/ml (Group 3), Prodrug VII 100 µg/ml (Group 4), Prodrug VII 1 µg/ml (Group 5), Prodrug XV 100 µg/ml (Group 6), Prodrug XV 1 µg/ml (Group 7). Zero score was observed for phosphate buffer for each of 15 min and 90 min points. Thus, the first from the left non-zero column represents treprostinil 100 µg/ml (Group 2).

Figure 27:
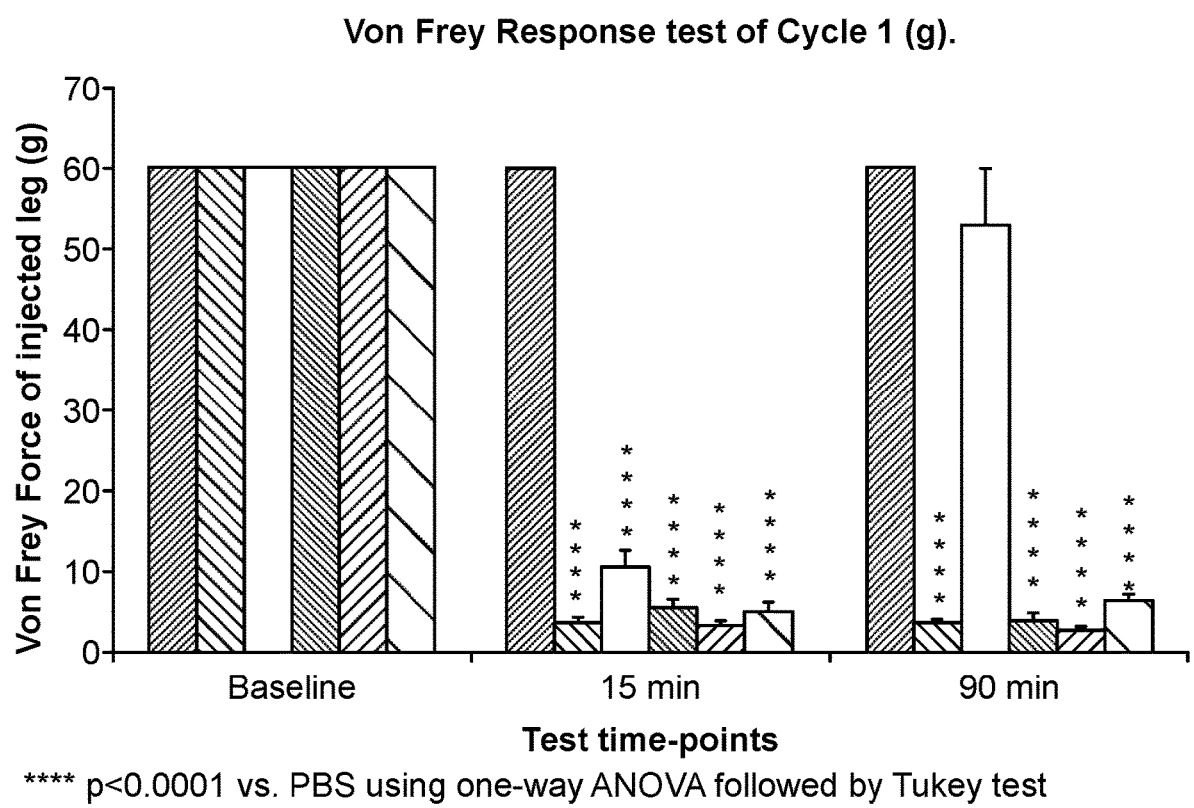

FIG. 27 presents results for Von Frey Response test of cycle 1 (g). Lower force indicates greater sensitivity. For each of baseline, 15 min and 90 min test points, columns represent the following left to right: Phosphate Buffer (Group 1), treprostinil 100 µg/ml (Group 2), PRODRUG VII 100 µg/ml (Group 3), Prodrug III 100 µg/ml (Group 4), Prodrug IV 100 µg/ml (Group 5), Prodrug XIV 100 µg/ml (Group 6).

Figure 28:
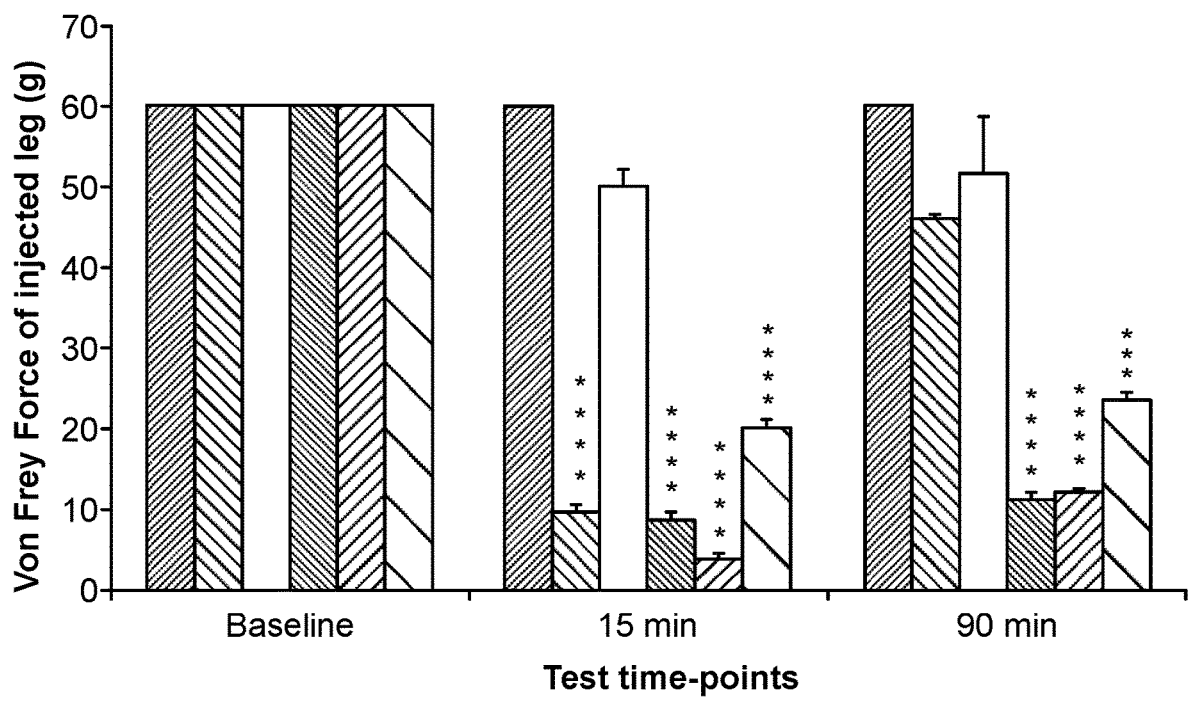

FIG. 28 presents results for Von Frey Response test of cycle 2 (g). Lower force indicates greater sensitivity. For each of baseline, 15 min and 90 min test time-points, columns represent the following left to right: Phosphate Buffer (Group 7), treprostinil 1 µg/ml (Group 8), PROD-RUG VII 1 µg/ml (Group 9), Prodrug III 1 µg/ml (Group 10), Prodrug IV 1 µg/ml (Group 11), Prodrug XIV 1 µg/ml (Group 12).

Figure 29:
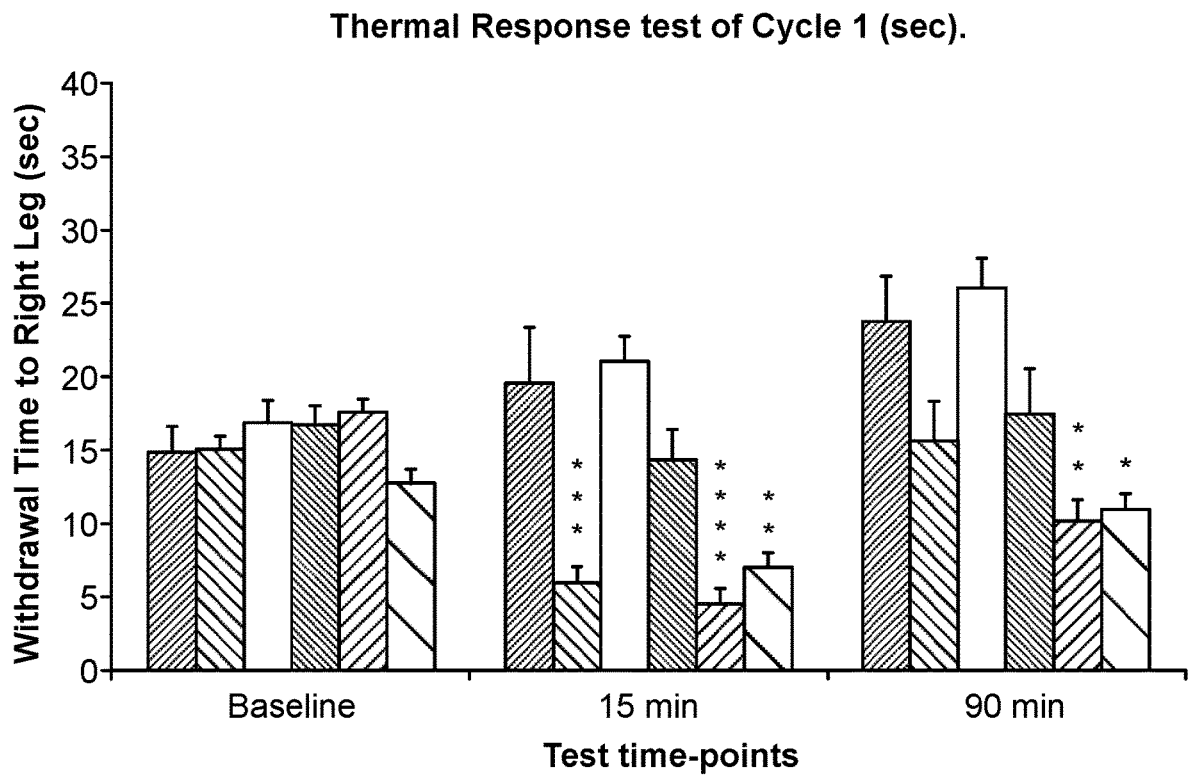

FIG. 29 presents results for Thermal Response test of cycle 1 (sec). Lower/faster time indicates greater sensitivity. For each of baseline, 15 min and 90 min test time-points, columns represent the following left to right: Phosphate Buffer (Group 1), treprostinil 100 µg/ml (Group 2), PROD-RUG VII 100 µg/ml (Group 3), Prodrug III 100 µg/ml (Group 4), Prodrug IV 100 µg/ml (Group 5), Prodrug XIV 100 µg/ml (Group 6).

Figure 30:
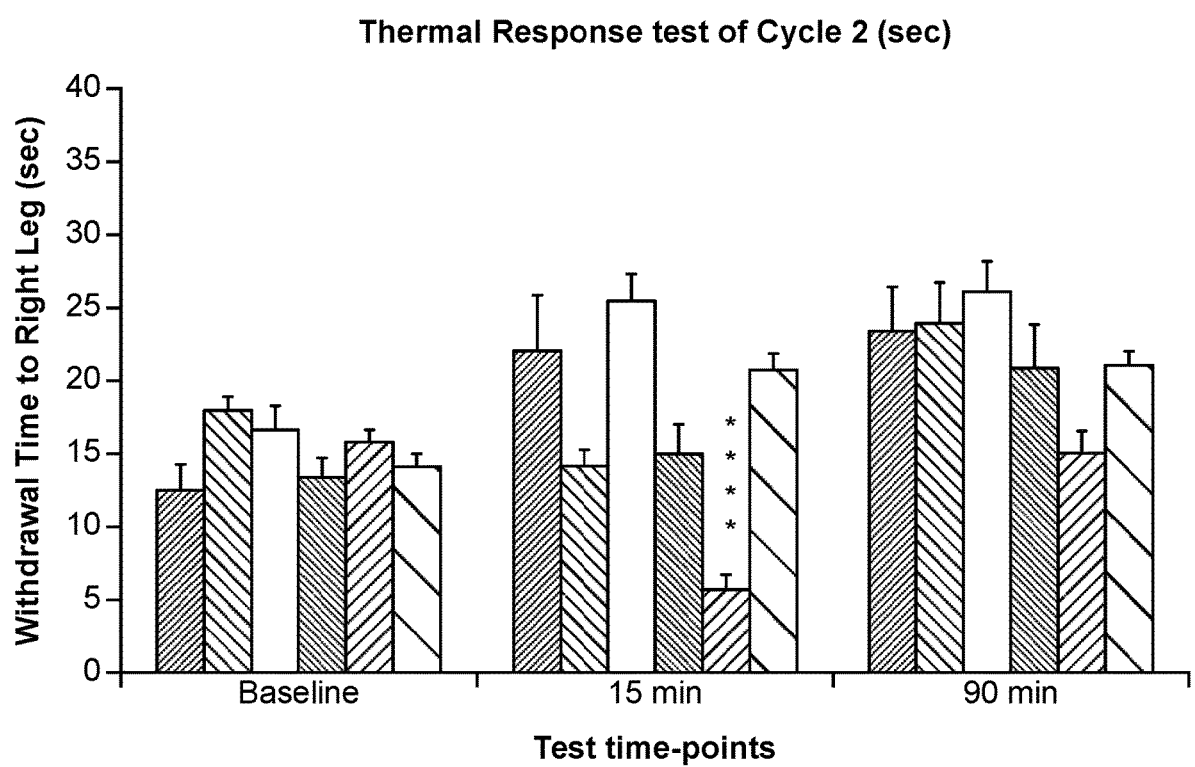

FIG. 30 presents results for Thermal Response test of cycle 2 (sec). Lower/faster time indicates greater sensitivity. For each of baseline, 15 min and 90 min test time-points, columns represent the following left to right: Phosphate Buffer (Group 7), treprostinil 1 µg/ml (Group 8), PROD-RUG VII 1 µg/ml (Group 9), Prodrug III 1 µg/ml (Group 10), Prodrug IV 1 µg/ml (Group 11), Prodrug XIV 1 µg/ml (Group 12).

Figure 31:
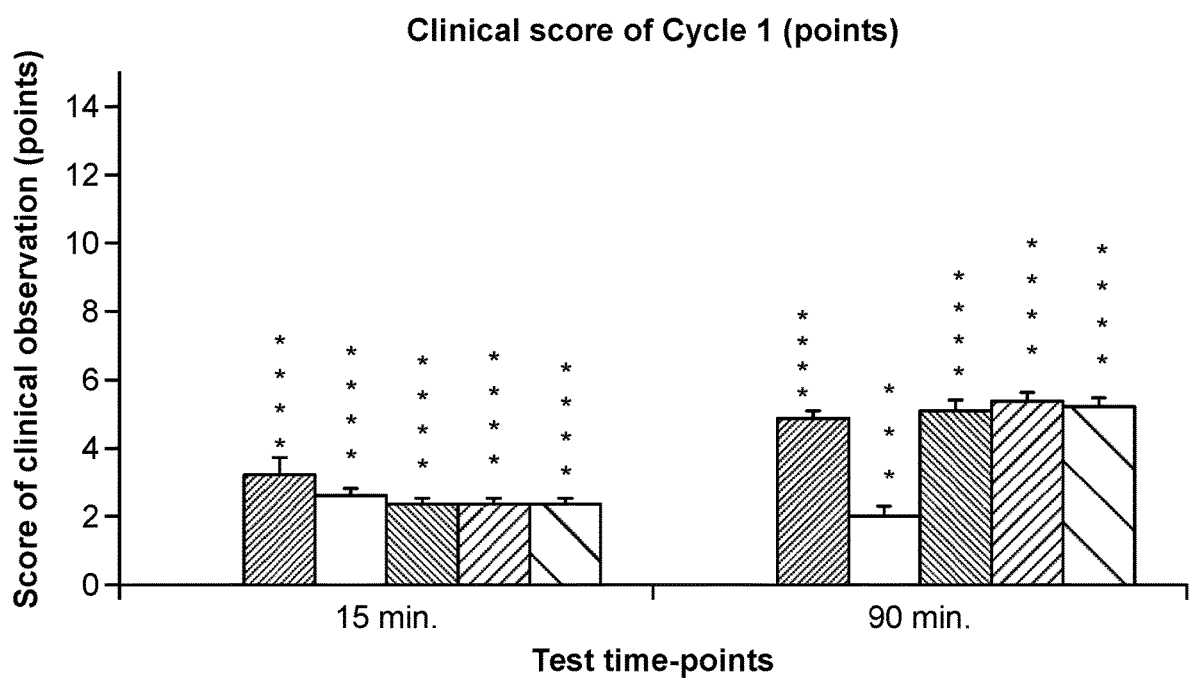

FIG. 31 presents mean clinical score of cycle 1 (points). Increased/Higher score indicates more observations of adverse events. For each of 15 min and 90 min test time-points, data presented the following left to right: Phosphate Buffer (Group 1), treprostinil 100 µg/ml (Group 2), PROD-RUG VII 100 µg/ml (Group 3), Prodrug III 100 µg/ml (Group 4), Prodrug IV 100 µg/ml (Group 5), Prodrug XIV 100 µg/ml (Group 6). Zero score was observed for phosphate buffer for each of 15 min and 90 min points. Thus, the first from the left non-zero column represents Treprostinil 100 µg/ml (Group 2).

Figure 32:
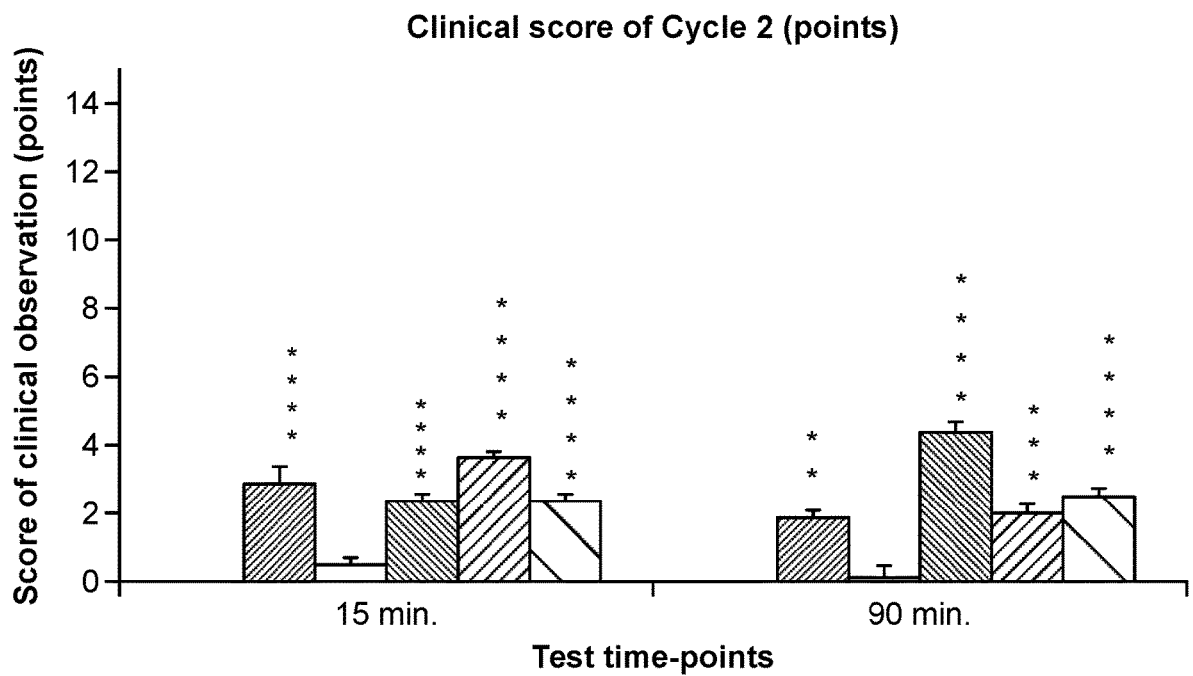

FIG. 32 presents mean clinical score of cycle 2 (points). Increased/Higher score indicates more observations of adverse events. For each of 15 min and 90 min test time-points, data presented the following left to right: Phosphate Buffer (Group 7), treprostinil 1 µg/ml (Group 8), PROD-RUG VII 1 µg/ml (Group 9), Prodrug III 1 µg/ml (Group 10), Prodrug IV 1 µg/ml (Group 11), Prodrug XIV 1 µg/ml (Group 12). Zero score was observed for phosphate buffer for each of 15 min and 90 min points. Thus, the first from the left non-zero column represents Treprostinil 1 µg/ml (Group 8).

Figure 33:
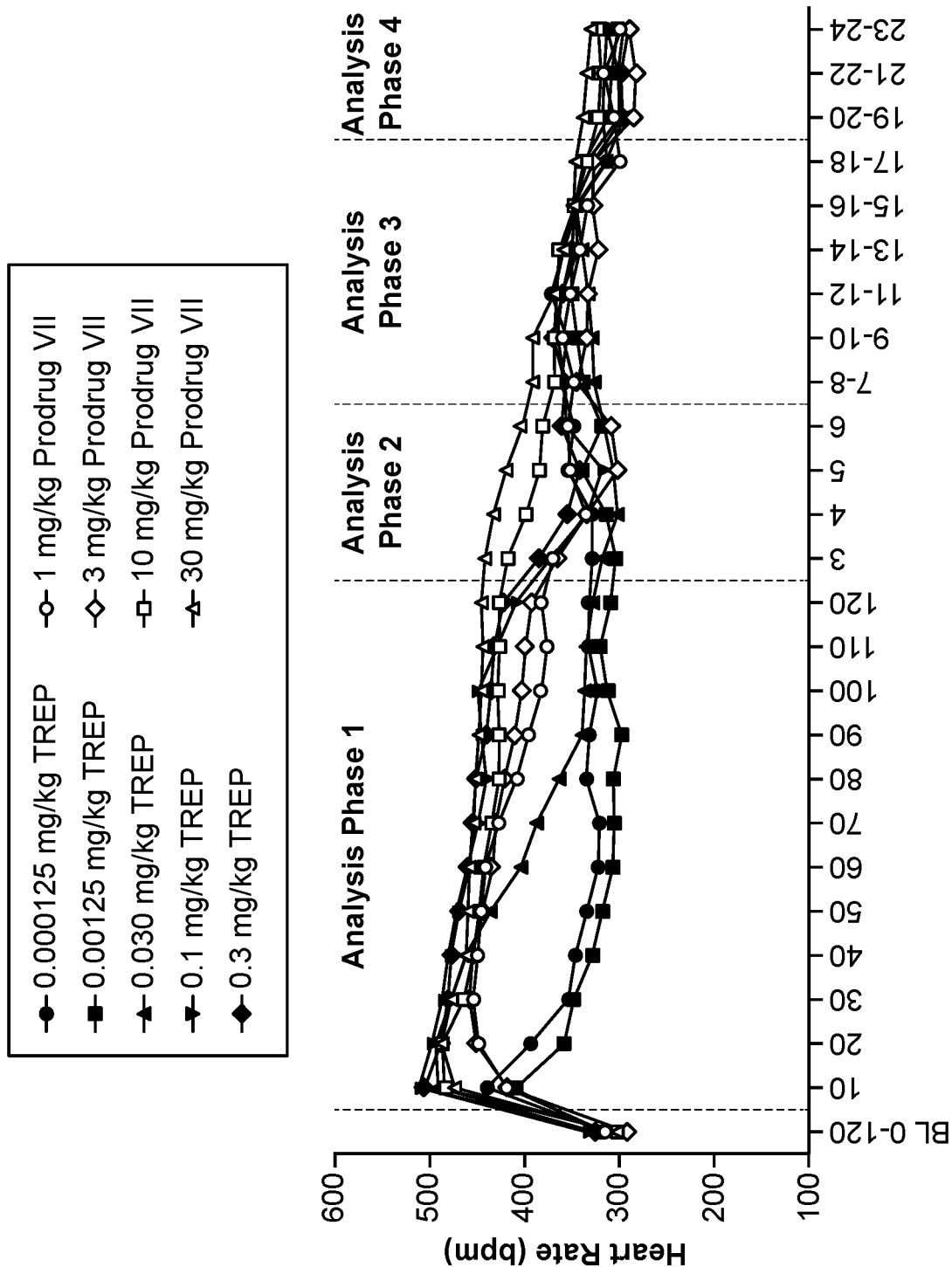

FIG. 33 presents a summary of radiotelemetry data for heart rate. Data presented as Means±SEM.

Figure 34:
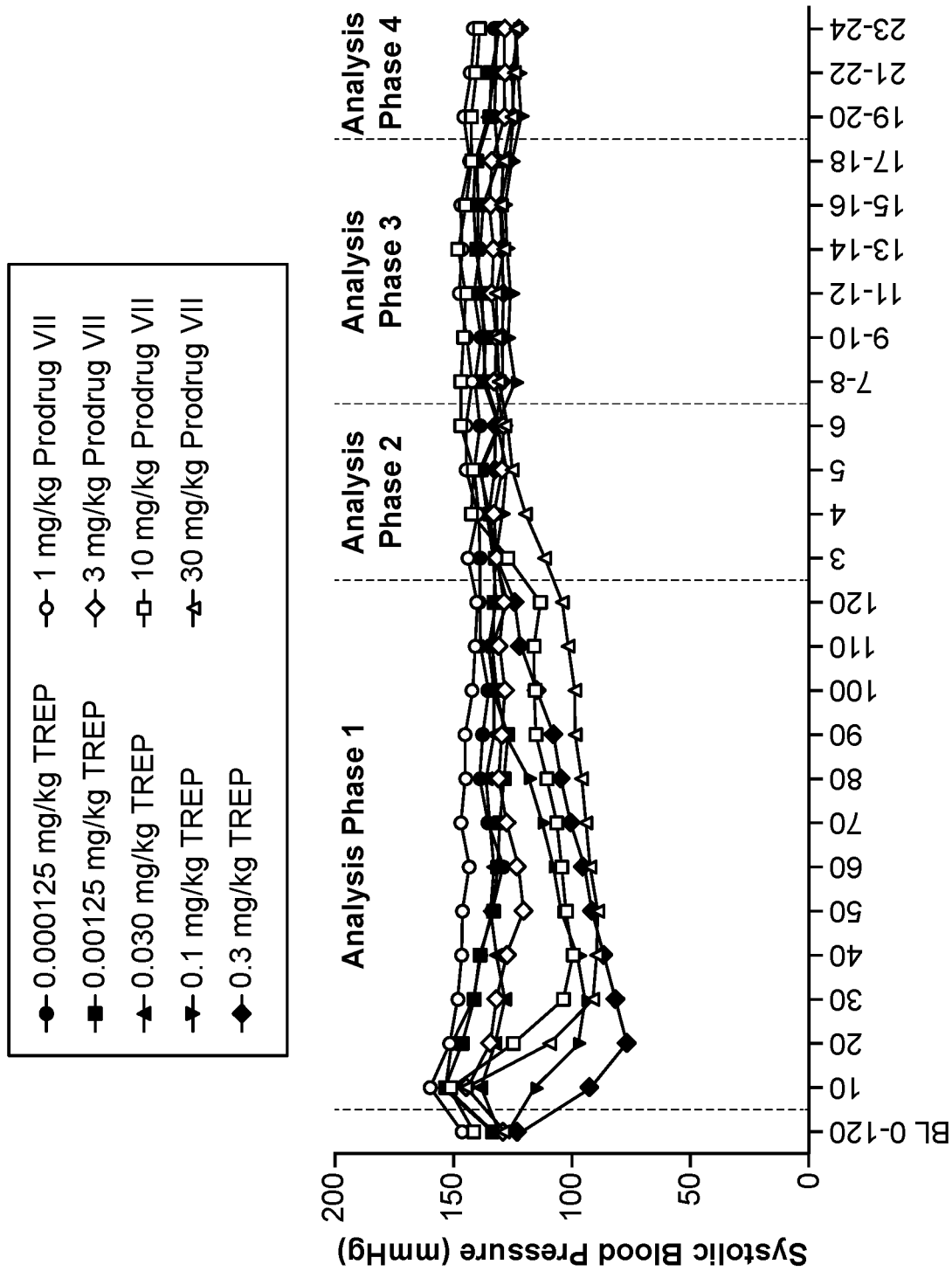

FIG. 34 presents a summary of radiotelemetry data for systolic blood pressure. Data presented as Means±SEM.

Figure 35:
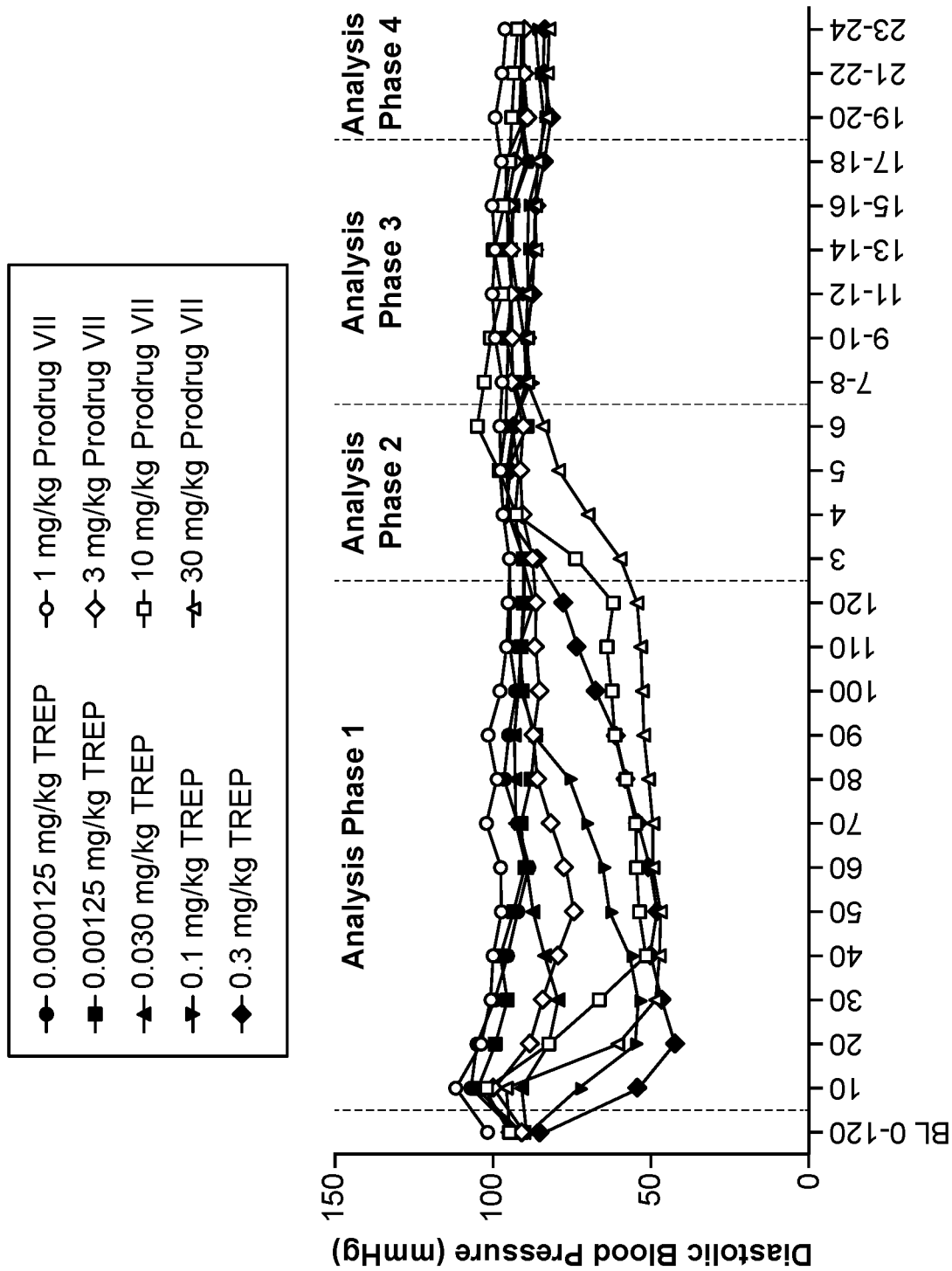

FIG. 35 presents a summary of radiotelemetry data for diastolic blood pressure. Data presented as Means±SEM.

Figure 36:
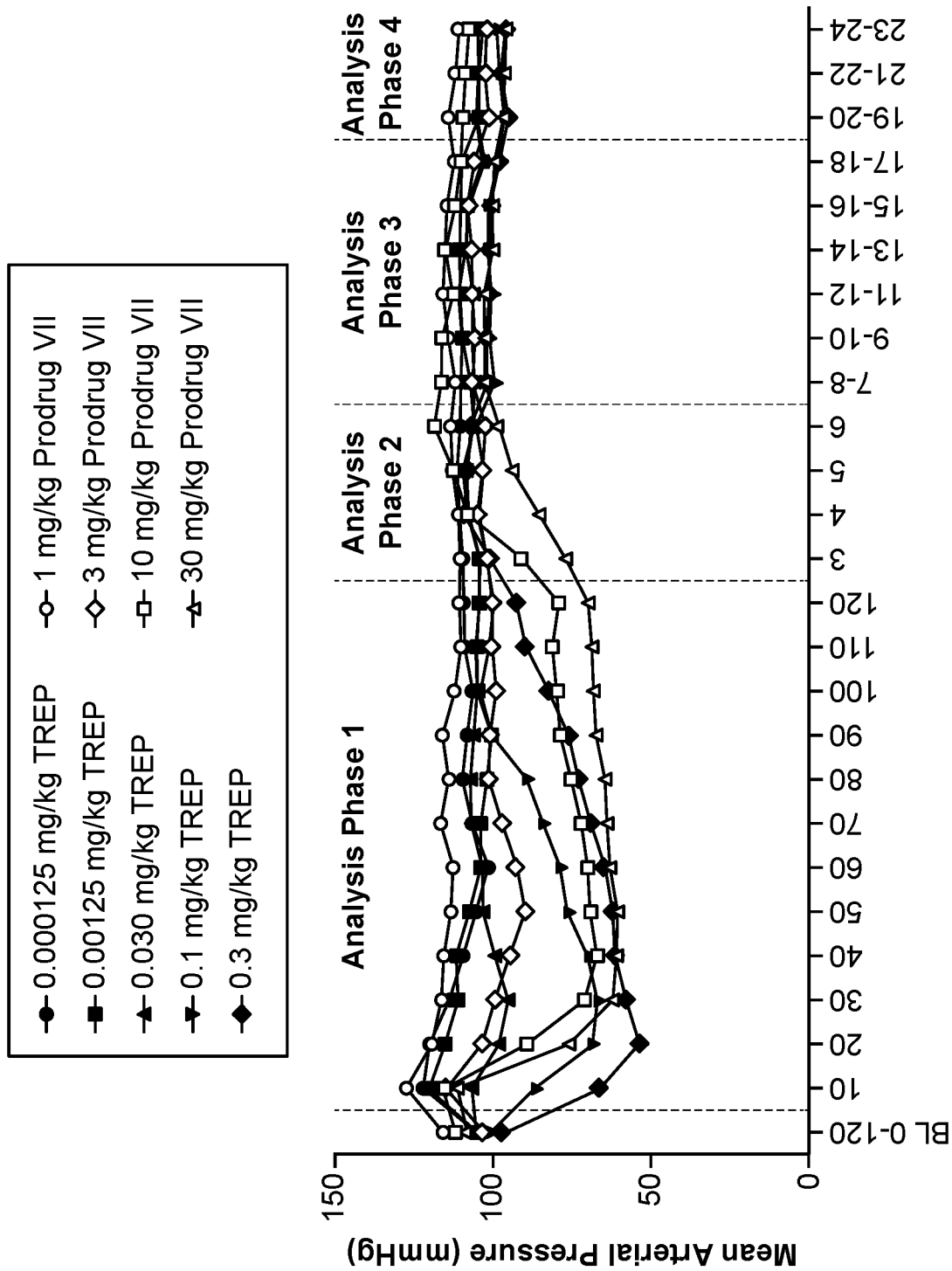

FIG. 36 presents a summary of radiotelemetry data for mean arterial pressure. Data presented as Means±SEM.

Figure 37:
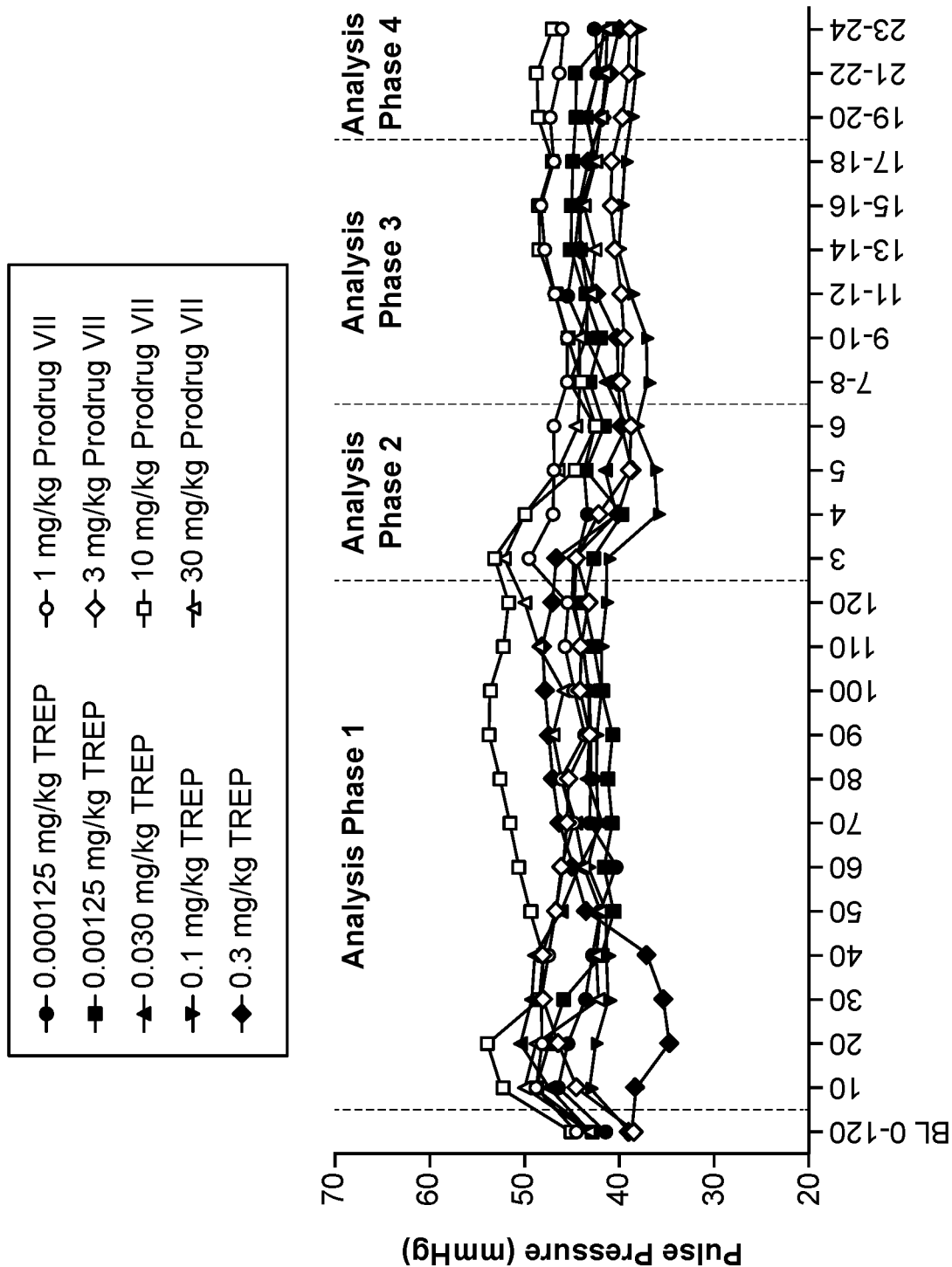

FIG. 37 presents a summary of radiotelemetry data for pulse pressure. Data presented as Means±SEM.

Figure 38:
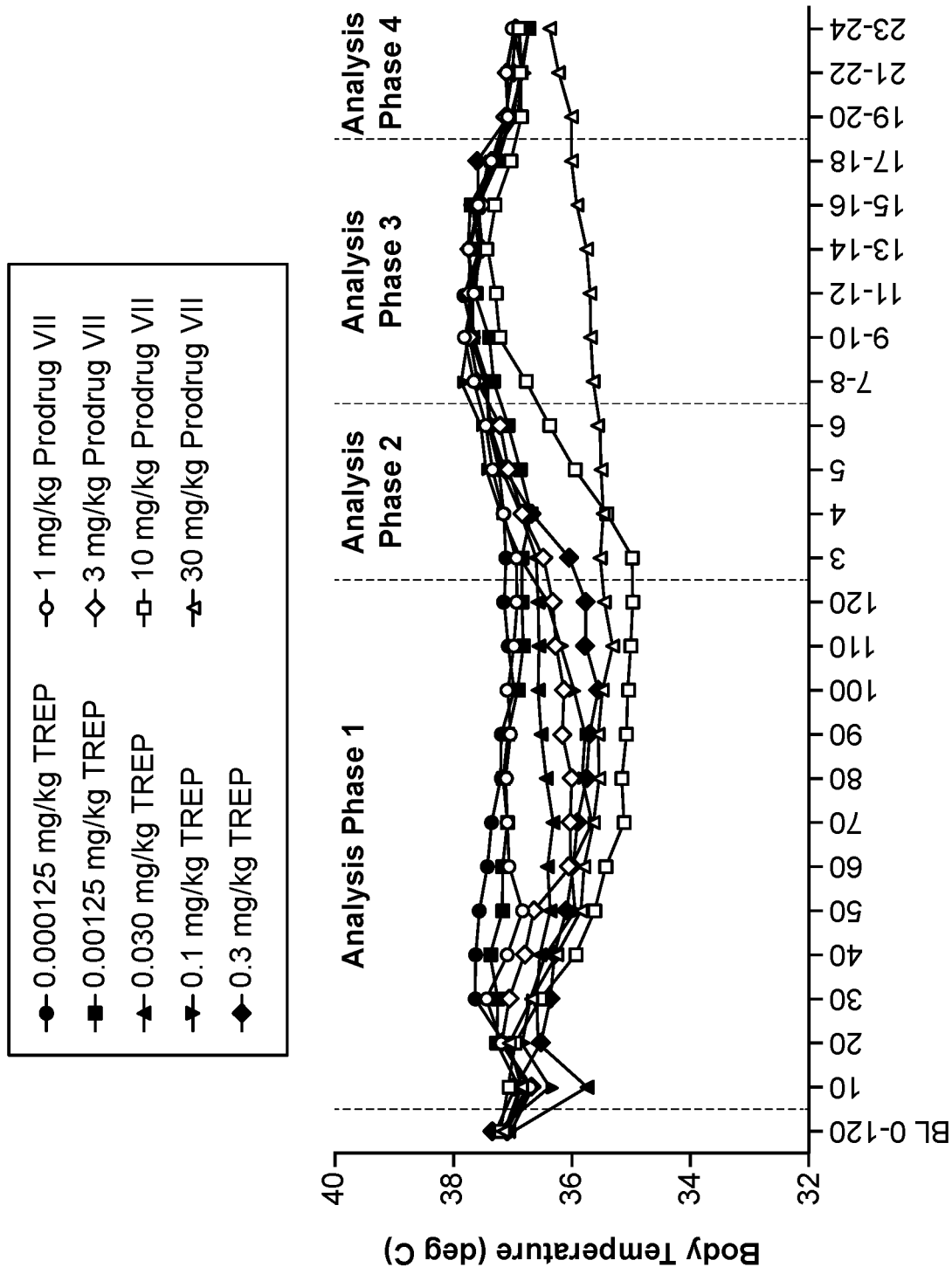

FIG. 38 presents a summary of radiotelemetry data for body temperature. Data presented as Means±SEM.

Figure 39:
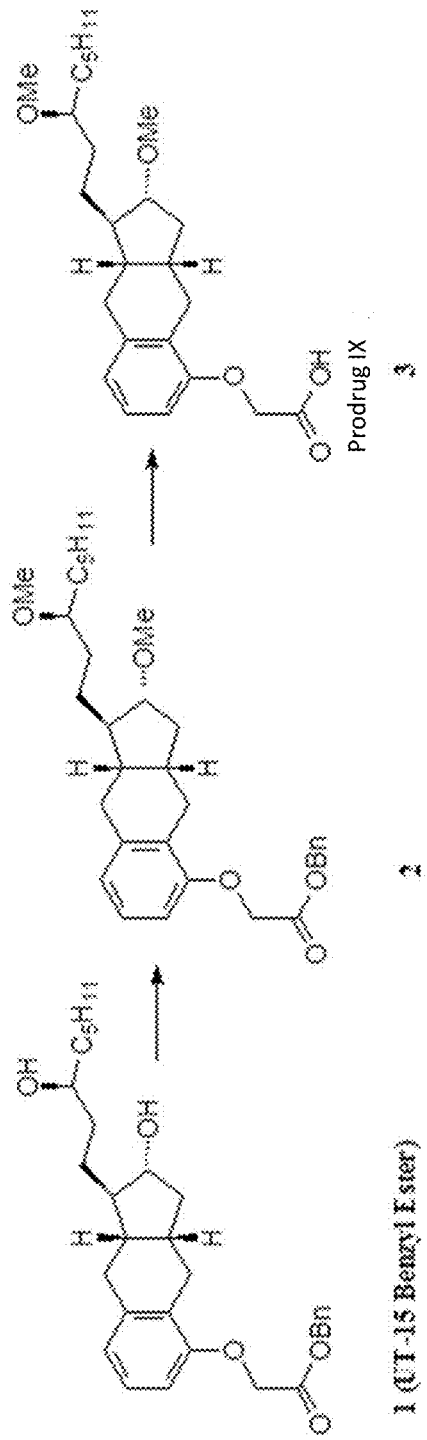

FIG. 39 schematically depicts a scheme for synthesis of Prodrug VIII.

DETAILED DESCRIPTION

Unless otherwise specified, "a" or "an" refers to one or more.

Treprostinil, the active ingredient in Remodulin® (injected or intravenous treprostinil), Tyvaso® (inhaled treprostinil), and Orenitram® (oral solid dosage form of treprostinil), was described in U.S. Pat. No. 4,306,075. Methods of making treprostinil and other prostacyclin derivatives are described, for example, in Moriarty, et al., J. Org. Chem. 2004, 69, 1890-1902, Drug of the Future, 2001, 26(4), 364-374, U.S. Pat. Nos. 6,441,245, 6,528,688, 6,700,025, 6,809,223, 6,756,117, 8,461,393, 8,481,782; 8,242,305, 8,497,393, 8,940,930, 9,029,607, 9,156,786 and 9,388,154 9,346,738; U.S. Published Patent Application Nos. 2012-0197041, 2013-0331593, 2014-0024856, 2015-0299091, 2015-0376106, 2016-0107973, 2015-0315114, 2016-0152548, and 2016-0175319; PCT Publication No. WO2016/0055819 and WO2016/081658.

Various uses and/or various forms of treprostinil are disclosed, for examples, in U.S. Pat. Nos. 5,153,222, 5,234,953, 6,521,212, 6,756,033, 6,803,386, 7,199,157, 6,054,486, 7,417,070, 7,384,978, 7,879,909, 8,563,614, 8,252,839, 8,536,363, 8,410,169, 8,232,316, 8,609,728, 8,350,079, 8,349,892, 7,999,007, 8,658,694, 8,653,137, 9,029,607, 8,765,813, 9,050,311, 9,199,908, 9,278,901, 8,747,897, 9,358,240, 9,339,507, 9,255,064, 9,278,902, and 9,278,903, U.S. Published Patent Application Nos. 2009-0036465, 2008-0200449, 2008-0280986, 2009-0124697, 2014-0275616, 2014-0275262, 2013-0184295, 2014-0323567, 2016-0030371, 2016-0051505, 2016-0030355, 2016-0143868, 2015-0328232, 2015-0148414, 2016-0045470, and 2016-0129087, and PCT Publications Nos. WO00/57701, WO2016/010538, and WO2016038532.

Treprostinil has the following chemical formula:

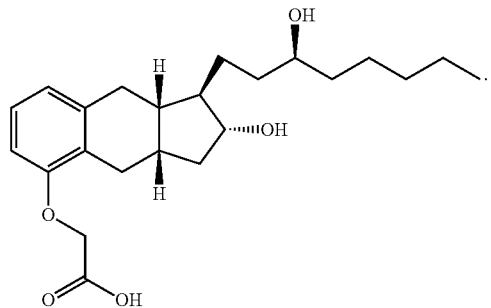 [SMILES: CCCCC[C@H](O)CC[C@@H]1[C@H]2Cc3cccc(OCC(=O)O)c3C[C@H]2C[C@H]1O]

The present inventors discovered that administering certain prodrugs of treprostinil by injection, such as subcutaneous administration, may lead to less or no pain compared to administering treprostinil or a salt of treprostinil, such as treprostinil sodium, via the same administration route in the same concentration.

One embodiment may be a method of treating a disease or condition that can be treated by administering to a patient an effective amount of a prodrug of treprostinil. The condition can be pulmonary hypertension, and the patient can be a human. The administration can occur by injection, such as subcutaneous injection. In some embodiments, the prodrug can be administered substantially continuously to the patient, such as by using an appropriate pump.

Another embodiment may be a method of a method of treating a disease or condition that can be treated by treprostinil comprising selection of a patient, who suffers from the disease or condition and who has experienced site pain upon administering treprostinil or a salt of treprostinil, such as treprostinil sodium, and administering to the patient an effective amount of a prodrug of treprostinil. The condition can be pulmonary hypertension, and the patient can be a human. The administration can occur by injection, such as subcutaneous injection. In some embodiments, the prodrug can be administered substantially continuously to the patient, such as by using an appropriate pump.

Diseases/conditions that may be treated by treprostinil include, but are not limited to, pulmonary hypertension, including pulmonary arterial hypertension (PAH) and chronic thromboembolic pulmonary hypertension; heart failure, such as congestive heart failure; ischemic diseases, such as peripheral vascular disease, Raynaud's phenomenon, Raynaud's disease, Buerger's disease, Scleroderma, renal insufficiency, intermittent claudication, ischemic limb disease, peripheral ischemic lesions; peripheral neuropathy, including diabetic neuropathy; extremity lesions and/or ulcers, such as foot ulcers and/or digital, ulcers (both finger and/or toe), which may or may not be caused by an ischemic disease, such as peripheral vascular disease, Raynaud's phenomenon, Raynaud's disease, Buerger's disease, Scleroderma, intermittent claudication, ischemic limb disease, and/or by peripheral neuropathy, such as diabetic neuropathy; pulmonary fibrosis, cystic fibrosis; asthma; cancer, which may be a cancer selected from the group consisting of lung, liver, brain, pancreatic, kidney, prostate, breast, colon and head-neck cancer.

In some embodiments, less or no pain associated with administering a treprostinil prodrug as compared to administering treprostinil or a salt of treprostinil has a number of benefits. For example, patients that could not tolerate pain associated with treprostinil may be able obtain the benefits of treprostinil treatment by receiving the prodrug. A visual analogue score (VAS score) may be collected continuously from a patient throughout the duration of an infusion, such as subcutaneous infusion. The VAS score may be then plotted as a function of time to calculate a pain area-under-curve (AUC). Less or no pain compared to administering treprostinil or a salt of treprostinil, such as treprostinil sodium, which may be achieved by administering treprostinil prodrug may mean a lower pain AUC for the treprostinil prodrug compared to treprostinil or a salt of treprostinil, such as treprostinil sodium. The VAS score method may allow quantification of more than just pain intensity as it may also allow integration of the intensity as well as monitoring change in the intensity with time. The VAS score method is disclosed, for example, in Lydick E, et al. Quality of Life Research. 1995; 4:41-45; and Van Wijk A J et al. Eur J Pain. 2013; 17:394-401.

The term "effective amount" may mean an amount of a treprostinil prodrug, which may be necessary to treat the disease or condition. In some embodiments, an effective amount of treprostinil prodrug may be the same or similar to an effective amount of treprostinil for treating the same disease or condition. In some embodiments, an effective amount of treprostinil prodrug may be different from an effective amount of treprostinil for treating the same disease or condition. A person of ordinary skill in the art would be able to determine and "effective amount" of the treprostinil prodrug based, for example, on the relevant disease or condition, the amount of treprostinil known to treat, ameliorate, or prevent the disease or condition, and the rate at which the prodrug converts to treprostinil in vivo.

In some embodiments, the prodrug may be a prodrug may be a prodrug disclosed in U.S. Pat. Nos. 7,384,978, 7,417,070, 7,544,713, 8,252,839, 8,410,169, 8,536,363, 9,050,311, 9,199,908, 9,278,901, 9,422,223 and 9,624,156, which are incorporated herein by reference in their entirety.

In some embodiments, the prodrug may be a prodrug disclosed in U.S. Pat. Nos. 9,371,264, 9,394,227, 9,505,737, and 9,643,911, which are incorporated herein by reference in their entirety.

In some embodiments, the prodrug may be one of prodrugs discussed below.

For example, in some embodiments, the prodrug may be a compound having the following formula:

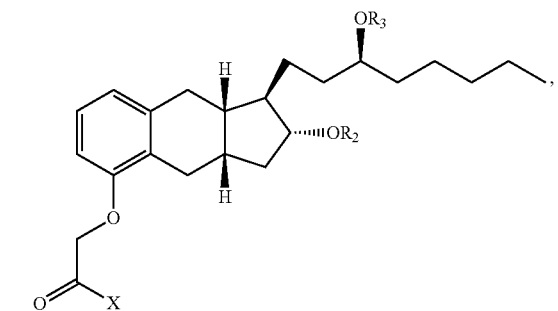

wherein X is $OR_9$ or $NR_1R_6$; wherein $R_9$ is H or $C_1$-$C_4$ alkyl, which may be optionally substituted with a terminal hydroxyl or carboxy group; wherein $R_1$ is H or $C_1$-$C_4$ alkyl and $R_6$ is

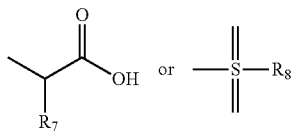

or wherein $R_1$ and $R_6$ are such that $NR_1R_6$ is an amide of an amino acid; $R_7$ is H or $C_1$-$C_4$ alkyl, which may be substituted with a terminal hydroxy or carboxy group; $R_8$ is H or $C_1$-$C_4$ alkyl; each of $R_2$ and $R_3$ is independently selected from H, $C_{1-4}$ alkyl,

phosphate and a group, in which $OR_2$ or $OR_3$ forms an ester of an amino acid; Y is $OR_4$ or $NR_4R_5$, each of $R_4$ and $R_5$ is independently selected from H and $C_{1-4}$ alkyl; with a proviso that all of $R_9$, $R_2$ and $R_3$ are not H; or a pharmaceutically acceptable salt of the compound.

In some embodiments, the prodrug may be a compound having the following formula:

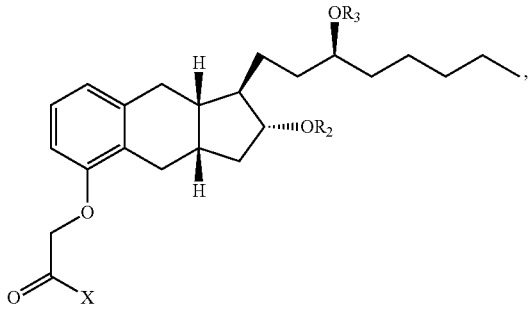

wherein X is OH or $NR_1R_6$, wherein $R_1$ is H or $C_1$-$C_4$ alkyl and $R_6$ is

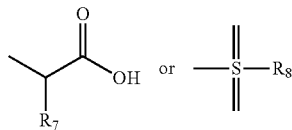

or wherein $R_1$ and $R_6$ are such that $NR_1R_6$ is an amide of an amino acid; $R_7$ is H or $C_1$-$C_4$ alkyl, which may be substituted with a terminal hydroxy or carboxy group, $R_8$ is H or $C_1$-$C_4$ alkyl and each of $R_2$ and $R_3$ is independently selected from H, $C_{1-4}$ alkyl, or

wherein Y is $OR_4$ or $NR_4R_5$, wherein each of $R_4$ and $R_5$ is independently selected from H and $C_{1-4}$ alkyl; with a proviso that when X is OH, both of $R_2$ and $R_3$ are not H; or a pharmaceutically acceptable salt of the compound.

In some embodiments, the prodrug is a compound of the following formula:

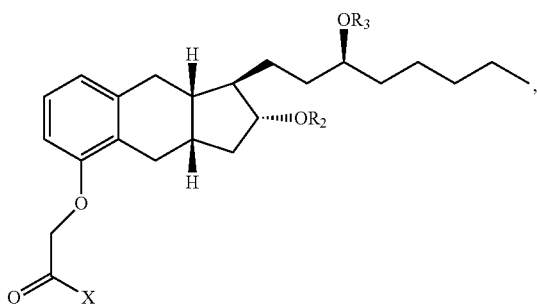

wherein:
X may be OH or

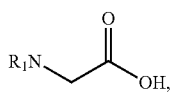

where $R_1$ is H or an alkyl, such as $C_1$-$C_4$ alkyl;
each of $R_2$ and $R_3$ may be independently selected from H, $C_{1-4}$ alkyl,

wherein Y may be $OR_4$ or $NR_4R_5$, each of $R_4$ and $R_5$ is independently selected from H and $C_{1-4}$ alkyl, with a proviso that when X is OH, both of $R_2$ and $R_3$ are not H; or a pharmaceutically acceptable salt thereof.

Examples of $C_{1-4}$ alkyl may include methyl, ethyl, propyl, isopropyl, n-butyl, sec-butyl, isobutyl or t-butyl.

Examples of $C_{1-4}$ alkyl substituted with a terminal hydroxyl group may include hydroxymethyl; hydroxyl ethyl; hydroxypropyl; 4-hydroxybutyl; 2-methyl-3-hydroxy propyl.

Examples of $C_{1-4}$ alkyl substituted with a terminal carboxy group may include carboxymethyl, carboxyethyl, carboxypropyl, 4-carboxybutyl, 2-methyl-3-carboxy propyl.

In some embodiments, X may be OH. In such a case, in certain embodiments, each of $R_2$ and $R_3$ may be each independently selected from a $C_{1-4}$ alkyl. $R_2$ and $R_3$ may be the same or different. In some cases, $R_2$ and $R_3$ may be the same. For example, both of $R_2$ and $R_3$ may be ethyl. Yet in some other cases, $R_2$ and $R_3$ may be different. For example, $R_2$ may be methyl and $R_3$ may be ethyl or vice versa.

In some embodiments, when X is OH, each of $R_2$ and $R_3$ may be independently selected from H and

In some cases, one of $R_2$ and $R_3$ may be

while the other is H. Yet in some other cases, both of $R_2$ and $R_3$ may be represented as

while being the same or different. In some embodiments, Y may be $OR_4$. In such a case, $R_4$ may be H or $C_{1-4}$ alkyl, such as methyl. In some cases, Y may be $NR_4R_5$. In such a case, each of $R_4$ and $R_5$ may be independently selected from H and $C_{1-4}$ alkyl, such as methyl. In some embodiments, $R_4$ and $R_5$ may be the same. For example, in some embodiments, both of $R_4$ and $R_5$ may be H or both of $R_4$ and $R_5$ may be methyl. Yet in some embodiments, $R_4$ and $R_5$ may be different. For example, one of $R_4$ and $R_5$ may be H, while the other may be methyl.

In some embodiments, when X is OH, at least one $R_2$ and $R_3$ may be phosphate. In certain cases, both of $R_2$ and $R_3$ may be phosphate. In certain other cases, one of $R_2$ and $R_3$ may be phosphate and the other may be H.

In some embodiments, when X is OH, at least one of $R_2$ or $R_3$ may be a group, in which $OR_2$ (or $OR_3$) forms an ester of an amino acid. In certain embodiments, one of $R_2$ or $R_3$ may be a group, in which $OR_2$ (or $OR_3$) forms an ester of an amino acid, while the other may be H. For example, $OR_2$ may form an ester of an amino acid, while $R_3$ is H; or $OR_3$ may form an ester of an amino acid, while $R_2$ is H. In certain embodiments, $R_2$ and $R_3$ may be such that $OR_2$ and $OR_3$ each form an ester of an amino acid. In certain cases, $OR_2$ and $OR_3$ may form an ester of the same amino acid. Yet in certain cases, $OR_2$ may form an ester of a first amino acid, while $OR_3$ may form an ester of a second amino acid, which is different from the first amino acid.

Amino acid(s) may be a D-isomer amino acid or an L-isomer amino acid. In certain embodiments, an amino acid may be a naturally occurring amino acid. Yet, in some embodiments, an amino acid may be an artificial amino acid. Examples of amino acids include, but not limited to, carbamic acid, glycine, alanine, valine, leucine, isoleucine, methionine, proline, phenylalanine, tryptophan, serine, threonine, asparagine, glutamine, tyrosine, cysteine, lysine, arginine, histidine, asparatice acid, glutamic acid. When $OR_2$ ($OR_3$) forms an ester of an amino acid, $R_2$ ($R_3$) may have

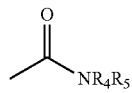

($R_4$ and $R_5$ as defined above) or

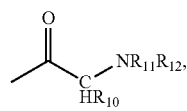

where $R_{10}$ is selected from the group consisting of amino acid side chains, $R_{11}$ and $R_{12}$ may be H. In the embodiments wherein the amino acid is proline, $R_{11}$ together with $R_{10}$ forms a pyrrolidine ring structure, while $R_{12}$ is H. $R_{10}$ may be, for example, one the naturally occurring amino acid side chains, for example —$CH_3$ (alanine), —$(CH_2)_3HCNH_2NH$ (arginine), —$CH_2CONH_2$ (asparagine), —$CH_2COOH$ (aspartic acid), —$CH_3SH$ (cysteine), —$(CH_2)_2CONH_2$ (glutamine), —$(CH_2)_2COOH$ (glutamic acid), —H (glycine), —$CHCH_3CH_2CH_3$ (isoleucine), —$CH_2CH(CH_3)_2$ (leucine), —$(CH_2)_4NH_2$ (lysine), —$(CH_2)_2SCH_3$ (methionine), —$CH_2Ph$ (phenylalanine), —$CH_2OH$ (serine), —$CHOHCH_3$ (threonine), —$CH(CH_3)_2$ (valine),

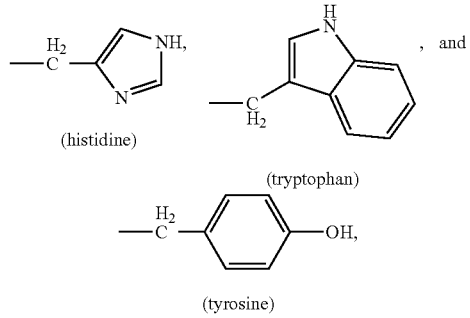

—$(CH_2)_3NHCONH_2$ (citrulline) or —$(CH_2)_3NH_2$ (ornithine). Ph designates a phenyl group.

In some embodiments, each of $R_2$ and $R_3$ are H. In such case, in certain embodiments, X may be $NR_1R_6$. $R_1$ may be H or $C_1$-$C_4$ alkyl. $R_6$ may be

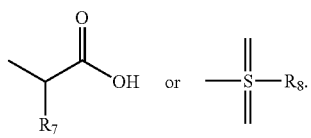

$R_7$ may be H or $C_1$-$C_4$ alkyl, which may be optionally substituted with a terminal hydroxy or carboxy group, $R_8$ may be H or $C_1$-$C_4$ alkyl. In certain embodiments, $R_1$ and $R_6$ are such that $NR_1R_6$ may form an amide of an amino acid.

In certain embodiments, $R_1$ may be H. In such case, in some embodiments, $R_6$ may be

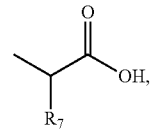

where $R_7$ may be H or $C_1$-$C_4$ alkyl, which may be optionally substituted with a terminal hydroxy or carboxy group.

In certain embodiments, $R_1$ may be H and $R_6$ may

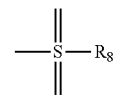

where $R_8$ may be H or $C_1$-$C_4$ alkyl, such as methyl or ethyl.

In certain embodiments, when $R_2$ and $R_3$ are each H, $NR_1R_6$ may form an amide of an amino acid, which may be an amino acid discussed above. $NR_1R_6$ may be, for example, or

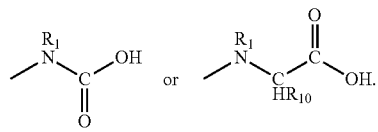

In certain cases, $R_1$ may be H and $R_{10}$ may be as defined above. In case of proline being the amino acid, $R_1$ and $R_{10}$ may form together a pyrrolidine ring structure.

In certain cases, when $R_2$ and $R_3$ are each H, X may be $OR_9$, $R_9$ may be $C_1$-$C_4$ alkyl, which may be optionally substituted with a terminal hydroxyl or carboxy group. When $R_9$ is $C_1$-$C_4$ alkyl is substituted with a terminal carboxy group, $R_9$ may be carboxymethyl, carboxyethyl, carboxypropyl, 4-carboxybutyl, 2-methyl-3-carboxy propyl.

In some embodiments, the prodrug may be a compound having one of the following formulas:

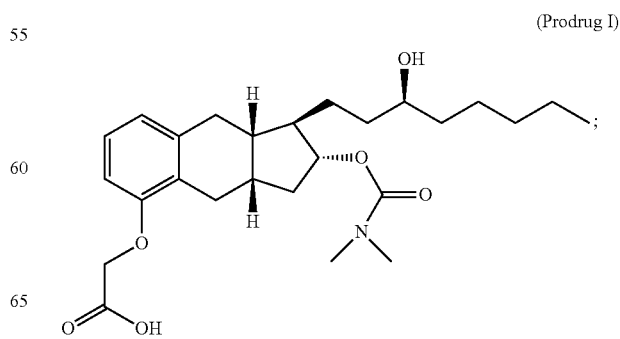

(Prodrug I)

(Prodrug II);

(Prodrug III);

(Prodrug IV);

(Prodrug V);

(Prodrug VI);

(Prodrug VII);

(Prodrug VIII);

(Prodrug IX);

(Prodrug X)

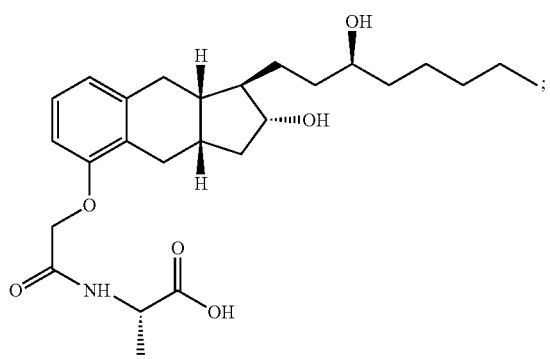

(Prodrug XI)

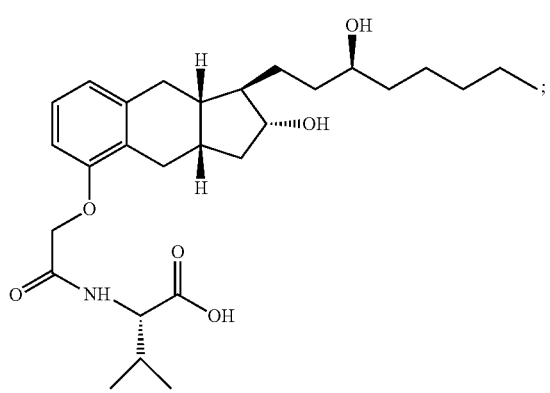

(Prodrug XII)

(Prodrug XIII)

(Prodrug XIV)

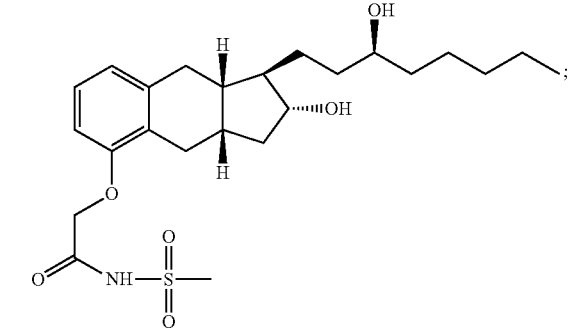

(Prodrug XV)

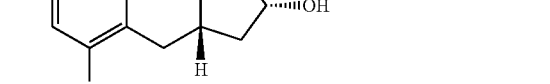

These prodrugs may have one or more advantages compared to treprostinil in addition to or alternative to reduction in site pain compared to administration of treprostinil or a salt thereof. For example, some of these prodrugs may have improved stability or greater tolerance in at least some patient populations.

At least some of these prodrugs may have half-life in human plasma of less than 150 minutes or less than 120 minutes or less than 90 minutes or less than 60 minutes or less than 50 minutes or less than 45 minutes or less than 40 minutes or less than 30 minutes or less than 20 minutes or less than 15 minutes or less than 12 minutes or about 10 minutes.

In certain embodiments, a prodrug of treprostinil may have equilibrium water solubility of at least 1 mg/mL, or at least 2 mg/mL or at least 3 mg/mL or at least 4 mg/mL or at least 5 mg/mL or at least 6 mg/mL. In certain embodiments, a prodrug of treprostinil may have equilibrium water solubility from 3 to 40 mg/mL or from 3 to 35 mg/mL or from 5 to 15 mg/mL or any value or subrange within these ranges. The solubility of the prodrug may be greater if pH is increased in a vehicle used in solubility measurement and/or if one or more salts are removed from the vehicle.

Although Remodulin® is approved by FDA for subcutaneous administration, some patients experience site pain as the result of such administration. Although the present invention is not bound by any particular theory, this site pain may be the result of the presence of treprostinil itself as opposed to inactive ingredients, such as m-cresol, or treprostinil in combination with any inactive ingredient. FIG. 9 reports withdrawal time at t=0, 15 min, and 90 min due to site pain by tested rats using the rat paw pain model, in which rats were administered one of the following: a) saline, b) a placebo formulation that contained citrate buffer, sodium chloride, and m-cresol but no treprostinil (shown as "Remodulin Placebo" in FIG. 9); c) a Remodulin formulation with a treprostinil concentration of 1 μg/mL containing treprostinil, citrate buffer, sodium chloride and m-cresol (shown as "Treprostinil 1 μg/mL" in FIG. 9); and d) a Remodulin formulation with a treprostinil concentration of 100 μg/mL containing treprostinil, citrate buffer, sodium chloride and m-cresol (shown as "Treprostinil 100 μg/mL" in FIG. 9). The vertical bars in FIG. 9 show how quickly the tested rats withdrew their paws in response to a heat stimulus following administration of the formulations at t=0, 15 min and 90 min. The data indicates that tested rats were more sensitive to the heat stimulus and withdrew their paws more quickly in the case of the formulations that contained treprostinil, whereas the Remodulin Placebo (containing the inactive ingredients of Remodulin but no treprostinil) did not increase their sensitivity.

Although the present invention is not limited by its theory of operation, site pain during subcutaneous administration may be due to treprostinil binding to one or more of the IP, DP or EP receptors at the site of the injection. Treprostinil may bind to these receptors at three functional locations, which correspond to three hydroxyl groups on the molecule, see e.g., Tsai and Wu, Eicosanoids, 2(3): 131-43 (1989). Accordingly, prodrugs of treprostinil with one or more groups attached to treprostinil's hydroxyl group(s), or other modifications that reduce binding to these receptors, may have less affinity for the receptors locally at the site of administration than treprostinil.

The phrase "prodrug of treprostinil" (also referred to "treprostinil prodrug" or just "prodrug" depending on context) as used herein refers to any derivative of treprostinil that converts in whole or in part to treprostinil in vivo following administration. The prodrug of treprostinil may have reduced affinity for one or more of the IP, DP or EP receptors locally at the site of injection as compared to treprostinil. In some embodiments, a "prodrug of treprostinil" can be a treprostinil derivative with one or more hydroxyl groups of the treprostinil structure modified to have reduced affinity for one or more of the IP, DP or EP receptors as compared to treprostinil, but which can be converted in vivo into active treprostinil following subcutaneous administration and subsequent diffusion into the blood. In some embodiments, the prodrug of treprostinil is completely or substantially converted in vivo to treprostinil outside the subcutaneous space, such as in the bloodstream. Preferred prodrugs include the compounds of formula I above. Other preferred prodrugs of treprostinil include amide, carbonate, or carbamate esters of treprostinil. In some embodiments, the prodrug of treprostinil has greater than 50%, 75%, 85%, 90%, 95%, or 98% conversion to treprostinil in vivo following administration. In some embodiments, this conversion takes place in 15 minutes, 30 minutes, 45 minutes, 1 hour, 2 hour, or 3 hours following administration. Prodrugs of treprostinil include pharmaceutically acceptable salts of such prodrugs.

Preferably, the prodrug of treprostinil is stable during storage, for example, by not hydrolyzing into treprostinil spontaneously in a solution before administering or during initial injection and at the site of injection. Preferably, the prodrug formulations of the present invention are free of treprostinil or substantially free of treprostinil in free acid form. In some embodiments, less than 10%, 5%, 2%, 1%, or 0.1% of the prodrug of treprostinil converts to treprostinil during a defined storage period. In some embodiments, that defined storage period can be 1, 2, 3, 6, or 12 months.

The prodrug of treprostinil when administered subcutaneously is preferably bioequivalent to subcutaneous administration of Remodulin. In one embodiment, the administered prodrug provides a plasma concentration of treprostinil that is between 80-125% of the $C_{max}$ and AUC for subcutaneous Remodulin. See, e.g., http://www.fda.gov/downloads/Drugs/GuidanceComplianceRegulatoryInformation/Guidances/UCM377465.pdf. In another embodiment, the $C_{max}$ and AUC values are between 95% and 105% of the subcutaneous Remodulin $C_{max}$ and AUC levels. Remodulin is preferably infused subcutaneously at 1.25 ng/kg/min, but if this initial dose cannot be tolerated due to side effects, the FDA approved label provides for reducing the infusion rate to 0.625 ng/kg/min.

FIG. 8 presents plasma concentration of treprostinil as a function of time. The lower and upper limits in FIG. 8 correspond respectively to 75% and 125% of the plasma concentration for subcutaneously administered Remodulin, which represents one preferred range of bioequivalent plasma concentrations for targeting with the prodrugs of the invention. FIG. 8 shows a plot for one possible subcutaneously administered prodrug formulation of treprostinil, which fits between the lower and upper limits, and therefore is bioequivalent to subcutaneously administered Remodulin in terms of plasma concentrations of treprostinil measured over a certain time period.

The disclosed treprostinil prodrugs, such as amide, carbamate, and carbonate prodrugs, may have one or more advantages over common ester prodrugs especially for parenteral administering, including subcutaneous administration. For example, the disclosed treprostinil prodrugs, such as amide, carbamate and carbonate prodrugs, may be more stable than common ester prodrugs, which may have a tendency to hydrolyze, thereby prematurely converting to treprostinil when it is not desired, e.g., in a solution or at an injection site.

A "pharmaceutically acceptable salt" includes a salt with an inorganic base, organic base, inorganic acid, organic acid, or basic or acidic amino acid. A salt of an inorganic base may be a salt of an alkali metal such as sodium or potassium; a salt of an alkaline earth metal such as calcium and magnesium or aluminum; and a salt of ammonia. A salt of an organic base may be, for example, trimethylamine, triethylamine, pyridine, picoline, ethanolamine, diethanolamine, and triethanolamine. A salt of an inorganic acid may be, for example, a salt of hydrochloric acid, a salt of hydroboric acid, a salt of nitric acid, a salt of sulfuric acid, or a salt of phosphoric acid. A salt of an organic acid may be, for example, a salt of one of the following acids: formic acid, acetic acid, trifluoroacetic acid, fumaric acid, oxalic acid, lactic acid, tartaric acid, maleic acid, citric acid, succinic acid, malic acid, methanesulfonic acid, benzenesulfonic acid, and p-toluenesulfonic acid. A salt of a basic amino acid may be, for example, for example, a salt of arginine, lysine or ornithine. A salt of an acidic amino acid may be, for example, a salt of aspartic acid or glutamic acid.

"Pulmonary hypertension" refers to all forms of pulmonary hypertension, WHO Groups 1-5. Pulmonary arterial hypertension, also referred to as PAH, refers to WHO Group 1 pulmonary hypertension. PAH includes idiopathic, heritable, drug- or toxin-induced, and persistent pulmonary hypertension of the newborn (PPHN).

Treprostinil prodrugs of the invention may be provided in a form of a pharmaceutical composition, which may also comprise a pharmaceutically acceptable carrier, excipient, binder, diluent or the like. Such pharmaceutical composition may be manufactured by methods known in the art such as granulating, mixing, dissolving, encapsulating, lyophilizing, emulsifying or levigating processes, among others. The composition may be in the form of, for example, granules, powders, tablets, capsules, syrup, suppositories, injections, emulsions, elixirs, suspensions and solutions. The composition may be formulated for a number of different administration routes, such as, for oral administration, transmucosal administration, rectal administration, transdermal or subcutaneous administration, as well as intrathecal, intravenous, intramuscular, intraperitoneal, intranasal, intraocular or intraventricular injection. The treprostinil prodrug may be administered by any of the above routes, for example in a local rather than a systemic administration, including as an injection or as a sustained release formulation.

In one embodiment, the pharmaceutical composition can compromise a prodrug of treprostinil and a carrier, such as sterile water. In some embodiments, the prodrug of treprostinil is formulated for subcutaneous administration, and such formulation may or may not include m-cresol or another preservative.

For oral, buccal, and sublingual administration, powders, suspensions, granules, tablets, pills, capsules, gelcaps, and caplets may be acceptable as solid dosage forms. These can be prepared, for example, by mixing one or more treprostinil prodrugs, or pharmaceutically acceptable salts thereof, with at least one additive or excipient such as a starch or other additive. Suitable additives or excipients may be sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. Optionally, oral dosage forms may contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Additionally, dyestuffs or pigments may be added for identification. Tablets may be further treated with suitable coating materials known in the art.

Liquid dosage forms for oral administration may be in the form of pharmaceutically acceptable emulsions, syrups, elixirs, suspensions, slurries and solutions, which may contain an inactive diluent, such as water. Pharmaceutical formulations may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oil include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution.

Alternatively, sterile oils may be employed as solvents or suspending agents. Preferably, the oil or fatty acid is non-volatile, including natural or synthetic oils, fatty acids, mono-, di- or tri-glycerides.

For injection, the pharmaceutical formulation may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these. The compounds may be formulated for parenteral administration by injection such as by bolus injection or continuous infusion. A unit dosage form for injection may be in ampoules or in multi-dose containers. Besides those representative dosage forms described above, pharmaceutically acceptable excipients and carries are generally known to those skilled in the art and are thus included in the instant invention. Such excipients and carriers are described, for example, in "Remingtons Pharmaceutical Sciences" Mack Pub. Co., New Jersey (1991), which is incorporated herein by reference.

A treprostinil prodrug may be formulated in a formulation suitable for parenteral administration that may comprise sterile aqueous preparations of a treprostinil prodrug, or a pharmaceutically acceptable salt thereof, where the preparations may be isotonic with the blood of the intended recipient. These preparations may be administered by means of subcutaneous injection, although administration may also be effected intravenously or by means of intramuscular or intradermal injection. Such preparations may conveniently be prepared by admixing the compound with water or a glycine or citrate buffer and rendering the resulting solution sterile and isotonic with the blood. Injectable formulations according to the invention may contain from 0.1 to 5% w/v based on weight of treprostinil in the prodrug and may be administered at a rate of 0.1 ml/min/kg. Alternatively, the invention may administered at a rate of 0.625 to 50 ng/kg/min based on weight of treprostinil in the prodrug. Alternatively, the invention may be administered at a rate of 10 to 15 ng/kg/min based on weight of treprostinil in the prodrug.

In some embodiments, a concentration of a treprostinil prodrug in a formulation for parenteral administration, such as intravenous infusion or subcutaneous infusion (including continuous subcutaneous infusion), may be from 0.0005 to 30 mg/mL or from 0.0007 to 50 mg/mL or from 0.001 to 15 mg/mL or any value or subrange within these ranges. Exemplary concentrations may include 0.1 mg/mL, 1 mg/mL, 2.5 mg/mL, 5 mg/mL or 10 mg/mL.

In some embodiments, a formulation of a treprostinil prodrug for parenteral administration, such as intravenous infusion or subcutaneous infusion (including continuous subcutaneous infusion), may be prepared by admixing the prodrug with a vehicle, such as a buffer. In certain embodiments, the vehicle may be a phosphate containing vehicle, i.e. at least one phosphate salt, which may be for example, dibasic phosphate, such as sodium dibasic phosphate or potassium dibasic phosphate, or tribasic phosphate, such as sodium tribasic phosphate or potassium phosphate. In certain embodiments, the vehicle may also contain a halogen salt, such as a chloride salt, which may be, for example, sodium chloride or potassium chloride. The halogen salt, such as sodium chloride may be used to adjust tonicity of the vehicle. In certain embodiments, it may be preferred that a phosphate and a halogen salt have the same cation. For example, when a phosphate is sodium phosphate, such as sodium tribasic phosphate or sodium tribasic phosphate, a halogen salt may a sodium halogen salt such as sodium chloride. Similarly, when a phosphate is potassium phosphate, such as potassium tribasic phosphate or potassium tribasic phosphate, a halogen salt may a potassium halogen salt such as potassium chloride. A solvent in the vehicle may contain water. In certain embodiments, water may be the only solvent in the vehicle. Yet in certain embodiments, the vehicle may contain one or more additional solvent in addition to water. In some embodiments, an additional solvent may be a preservative, such as m-cresol.

Preferably, the vehicle is isotonic with blood of a patient, such as a human being. The term isotonic may mean that the osmolarity and ion concentrations of the vehicle match those of the patient, such as human being. Non-limiting example of vehicles include phosphate-buffered saline, which is a water based salt solution containing disodium hydrogen phosphate, sodium chloride and, in some formulations, potassium chloride and potassium dihydrogen phosphate. Other examples may include a vehicle containing 20 mM disbasic sodium phosphate with 125 mM sodium chloride and a vehicle containing 15 mM sodium phosphate tribasic, 125 mM sodium chloride and 0.3% w/w m-cresol.

In certain embodiments, a treprostinil prodrug may be administered subcutaneously. In some embodiments, the subcutaneous administration may be continuous subcutaneous infusion, such as continuous subcutaneous infusion by an infusion pump, which is preferably portable or implantable.

In some embodiments, a treprostinil prodrug may be administered subcutaneously at a rate (dose) of 0.1 to 100 ng/kg/min or 0.2 to 70 ng/kg/min or 0.3 to 50 ng/kg/min or 0.6 to 10 ng/kg/min based on weight of treprostinil in the prodrug or any value or subrange within these ranges. In some embodiments, the infusion may start at an initial rate (dose), which may be later increased or decreased based on a patient's response to the initial rate (dose). For example, an initial rate (dose) may be 1.25 ng/kg/min, which may be increased in increments of 1.25 ng/kg/min per week or 2.5 ng/kg/min per week depending on the patient's tolerance. If the patient does not tolerate the initial rate (dose) due to, for example, a side effect, which may be, for example, mild to moderate hepatic insufficiency and/or headache, the initial rate (dose) may be reduced down to 0.625 ng/kg/min. After the patient develops a tolerance to the lower rate (dose), the rate (dose) may be increased.

The treprostinil prodrugs may be used for one or more of the same purposes for which treprostinil is known to be useful. For example, the treprostinil prodrugs may be used for administering to a subject, such as a human being, for treating a disease or disorder, which may be treated with treprostinil, such as pulmonary hypertension, including pulmonary arterial hypertension and chronic thromboembolic pulmonary hypertension. For therapeutic purposes, such as treating pulmonary hypertension, a treprostinil prodrug may be administered to a subject, such a human being, in a therapeutically effective amount, which may be an amount of the treprostinil prodrug, which is sufficient to ameliorate one or more symptoms of a disease or disorder, which may be treated with treprostinil, such as pulmonary hypertension.

The treprostinil prodrugs may be used therapeutically, including in cytoprotection, reducing cell proliferation, promoting vasodilation and/or inhibiting platelet aggregation. In some embodiments, the treprostinil prodrugs may be used in treatment of a vascular disease, such as pulmonary hypertension, heart failure (including congestive heart failure), or peripheral vascular disease. The treprostinil prodrugs may have vasodilating effects so that they may be used for treating pulmonary hypertension, which may, for example, result from one or more forms of connective tissue disease, such as lupus, scleroderma or mixed connective tissue disease.

The treprostinil prodrugs may be also used in cancer, coagulation disorders, and inflammatory diseases. Use of treprostinil for inhibiting metastasis of cancer cells is disclosed in US 2003-0108512 and U.S. Pat. No. 6,803,386, which are both incorporated herein in their entirety. Treprostinil prodrugs may be prepared according to methods illustrated in FIGS. 1-6 and as demonstrated in examples below.

Scheme 2 illustrates synthesis of acetate amide Prodrug VII. This synthesis may start with treprostinil reacted with $NH_2CH_2COOBn$ to form a protected acetato amide compound of the following formula:

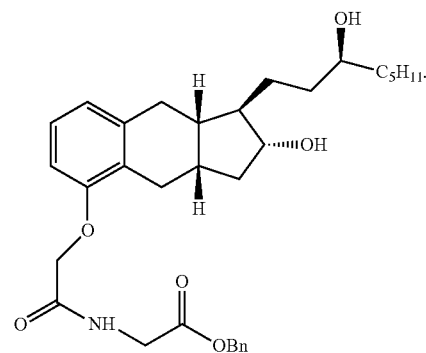

In some embodiments, an alkyl, such as $C_1$-$C_4$ alkyl, e.g. methyl or ethyl, may be used instead of benzyl. In such case, $NH_2CH_2COOR_4$, where $R_4$ is an alkyl, may be used for reacting with treprostinil while forming a protected acetato amide compound instead of $NH_2CH_2COOBn$.

The protected acetato amide compound may then transferred into acetato amide Prodrug VII. In case of Bn, such reaction may involve using Pd/C and $H_2$. In case of an alkyl, such as methyl or ethyl, the protected acetato amide compound may be reacted with a base, such as NaOH or KOH, to be transferred into acetato amide Prodrug VII.

Figure 6:
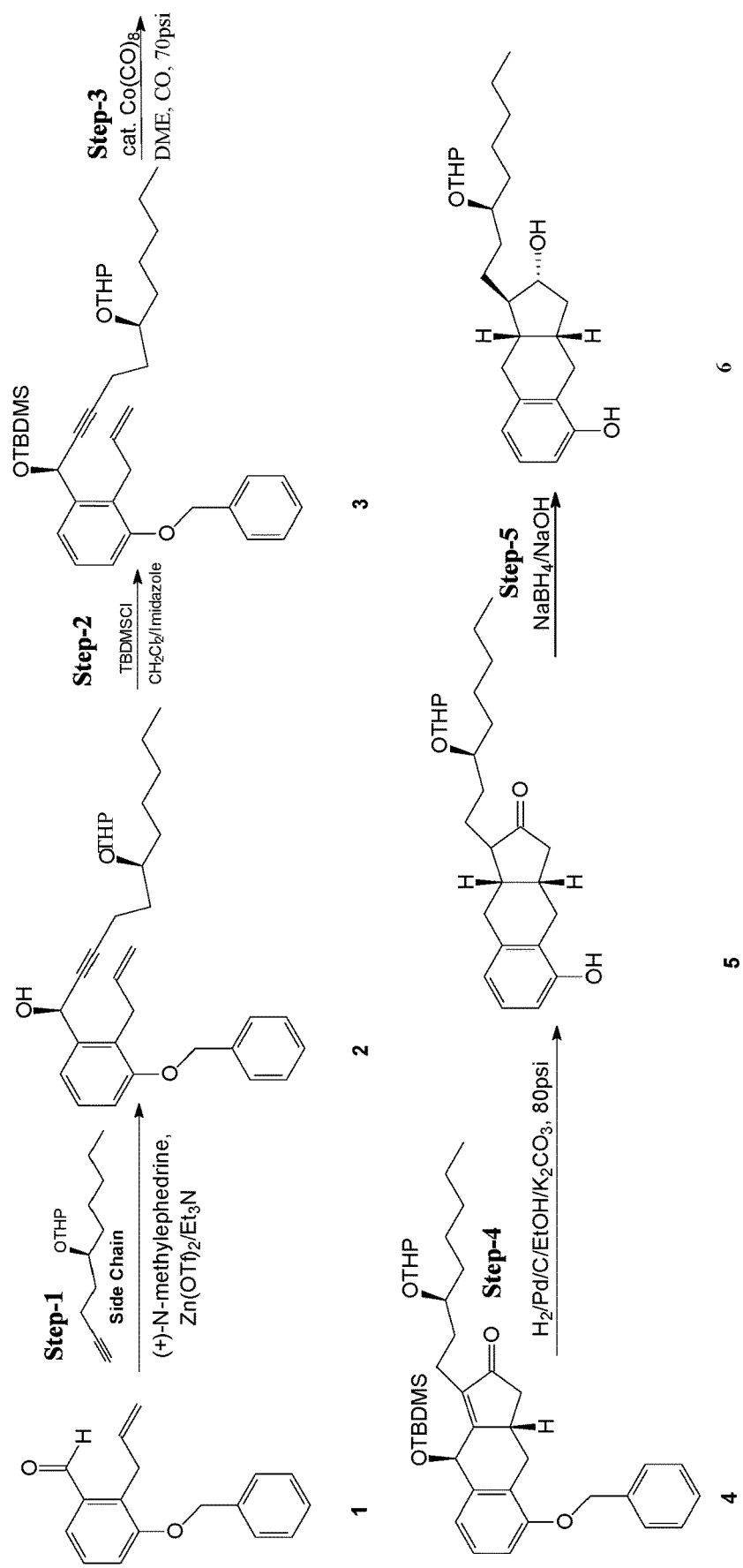
FIG. 6 is a scheme illustrating synthesis of a key starting material.

FIG. 6 illustrates synthesis of a starting compound of the following formula:

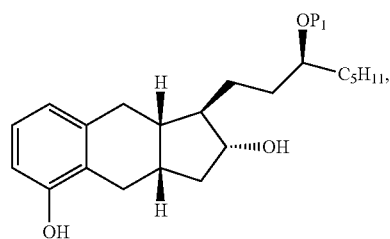

where $P_1$ may be a hydroxyl protecting group, such as 2-tetrahydropyranyl (THP) or a silyl protecting group, such as tert-Butyldimethylsilyl ether (TBDMS/TBS), Trimethylsilyl (TMS) Triethylsilyl (TES), tert-Butyldiphenylsilyl (TBDPS), Triisopropylsilyl (TIPS). This compound may be used as an important starting compound for synthesizing several treprostinil prodrugs. The process in FIG. 6 corresponds to the first five reaction of Scheme 2 of U.S. Pat. No. 8,940,930, which is incorporated herein in its entirety.

Besides the process disclosed in FIG. 6, the starting compound may also be synthesized for example, using methods disclosed U.S. Pat. Nos. 6,756,117 and 6,809,223. The synthesis of the starting compound may start a compound of the following formula:

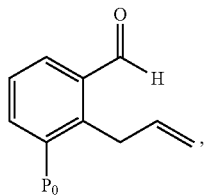

where $P_0$ is a hydroxyl protecting group, such as benzyl or a substituted benzyl. A substituted benzyl group may be optionally substituted at one or more meta, ortho or para positions with one or more substituents, which may be independently selected from the group consisting of —$NO_2$, —CN, halogen (e.g., —F, —Cl, —Br or —I), (C1-C3)alkyl, halo(C1-C3)alkyl, (C1-C3)alkoxy and halo(C1-C3)alkoxy. This compound

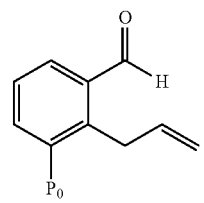

may be reacted with

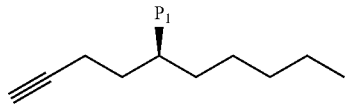

in the presence of (+)-N-methylephedrine, $Zn(OTf_2)/Et_3N$ or using (1S,2S)-3-(tertiary-butyldimethylsilyloxy)-2-N,N-dimethylamino-L-(para-nitrophenyl)-propane-1-ol to form a compound of the following formula

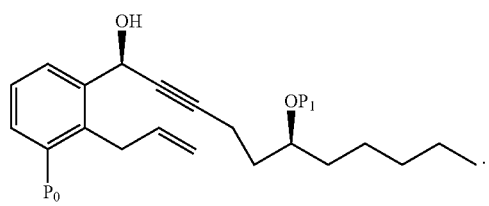

This compound may then transferred into the key starting compound using the reactions disclosed in U.S. Pat. No. 6,940,930.

The starting compound of the following formula

Figure 1:
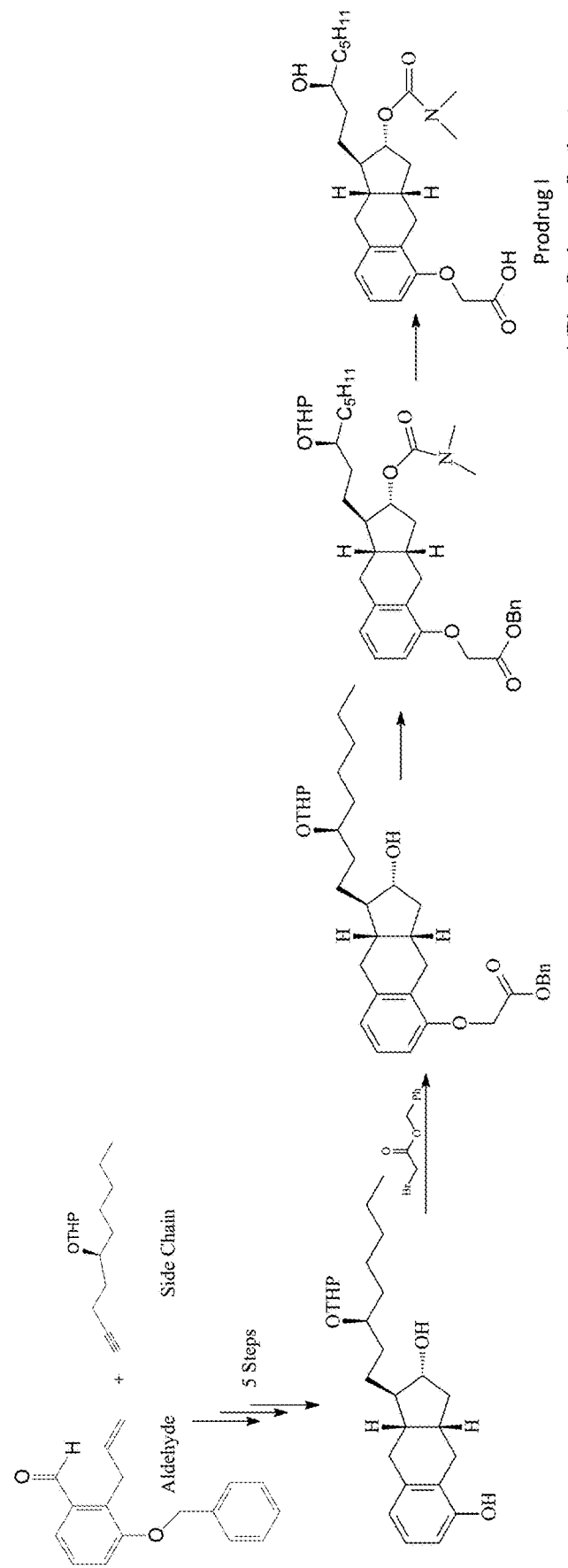
FIG. 1 is a scheme illustrating synthesis of cyclopentyl ring carbamate prodrug I.
Figure 2:
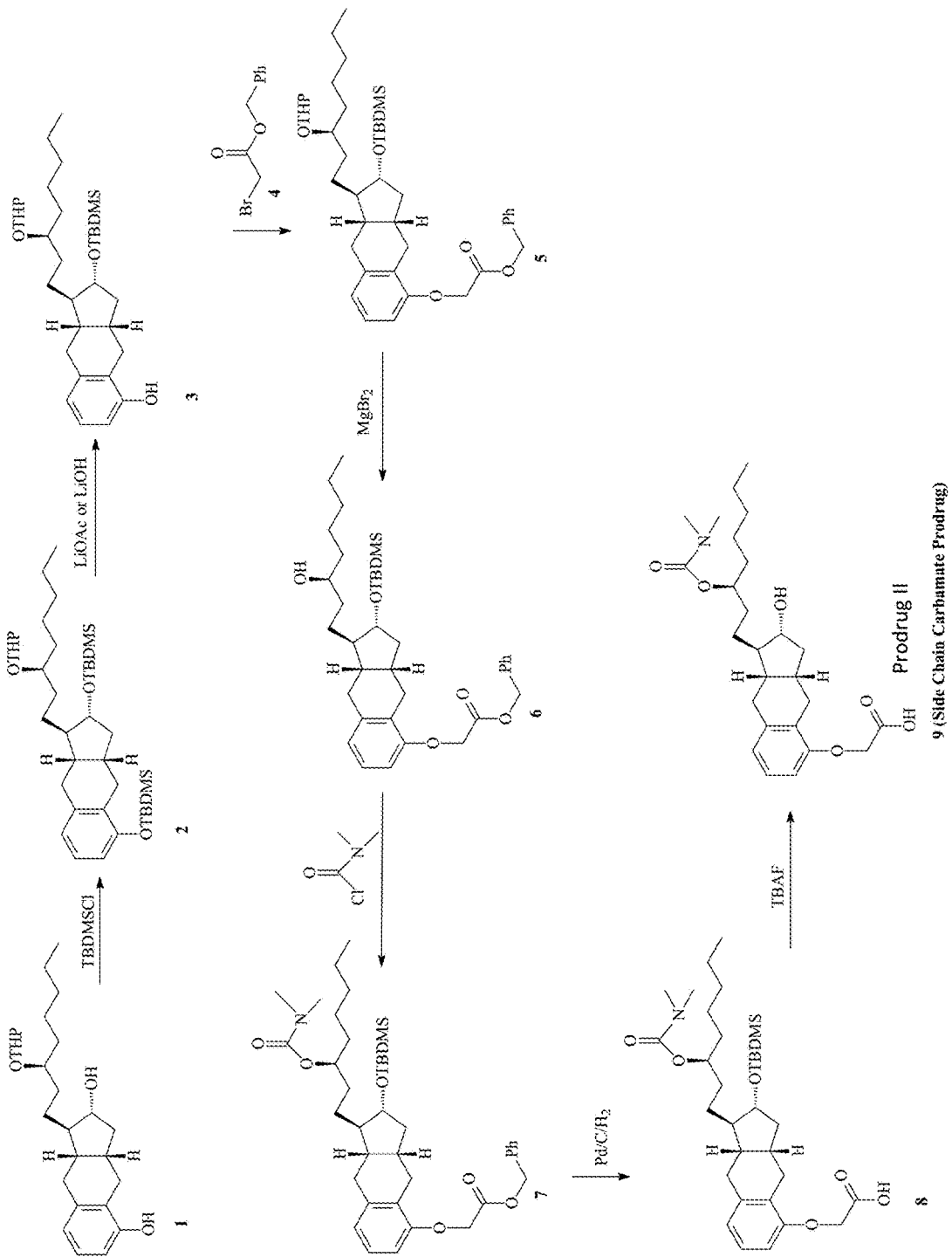
FIG. 2 is a scheme illustrating synthesis of side chain carbamate prodrug II.
Figure 3:
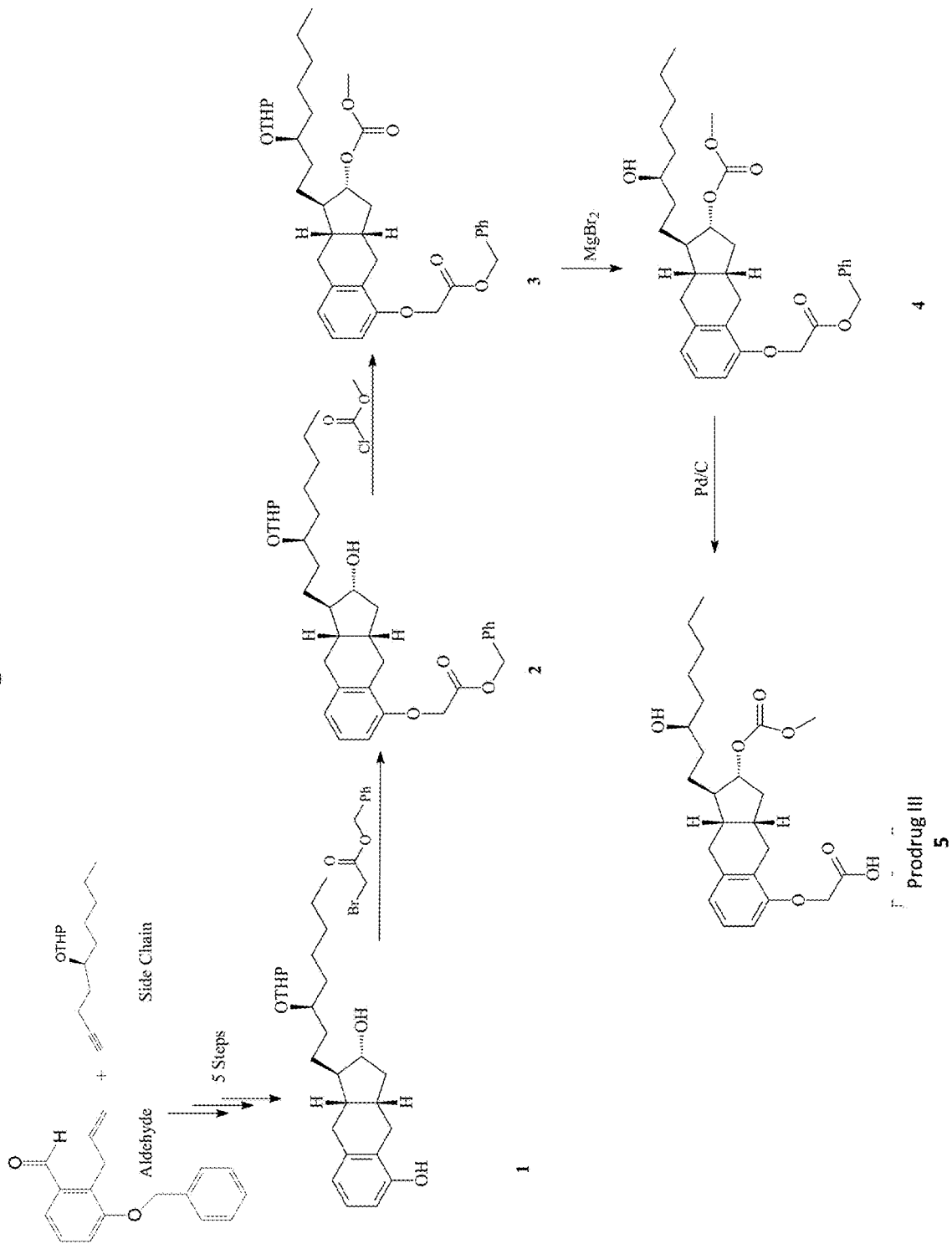
FIG. 3 is a scheme illustrating synthesis of cyclopentyl ring carbonate prodrug III.
Figure 4:
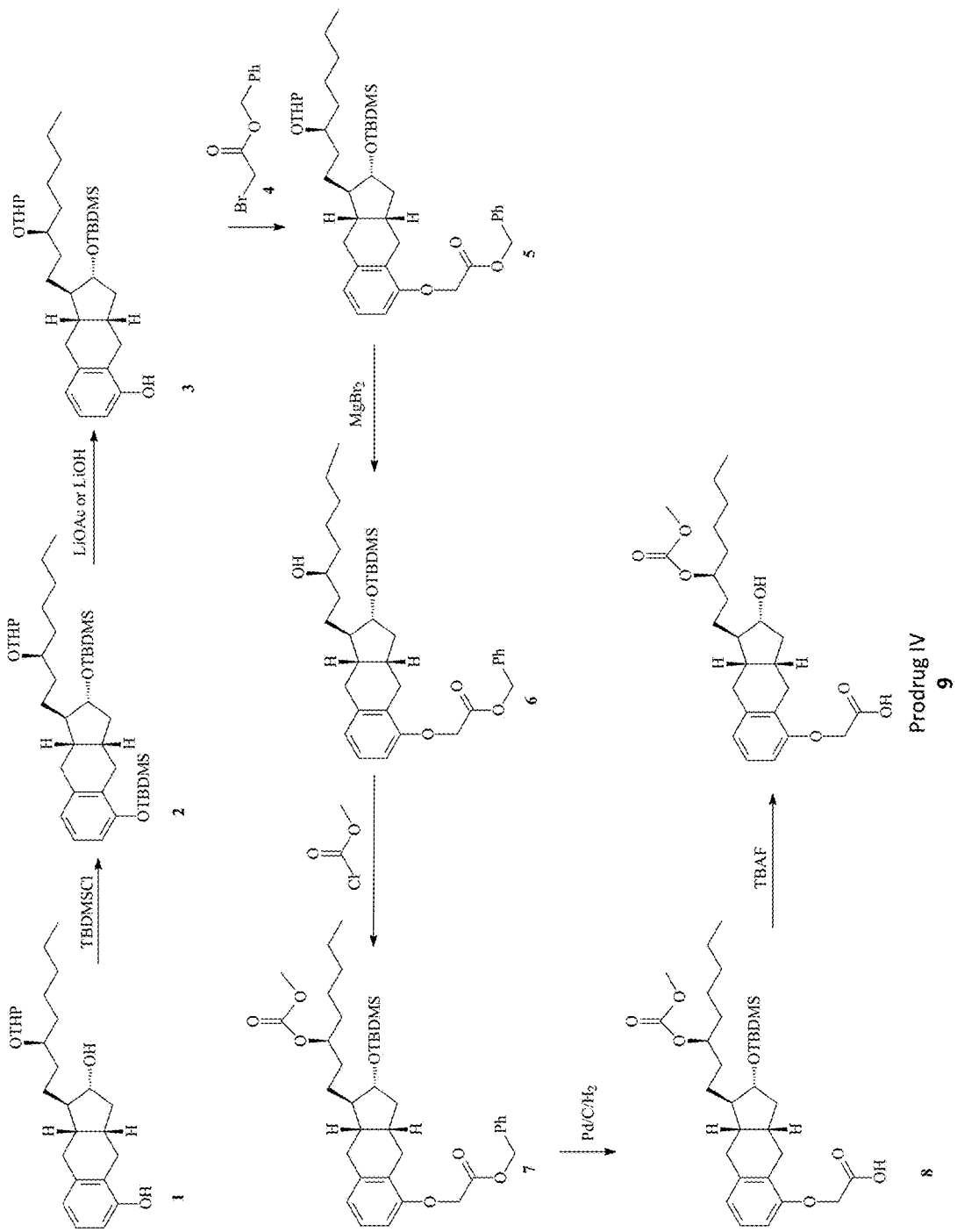
FIG. 4 is a scheme illustrating synthesis of side chain carbonate prodrug IV.
Figure 5:
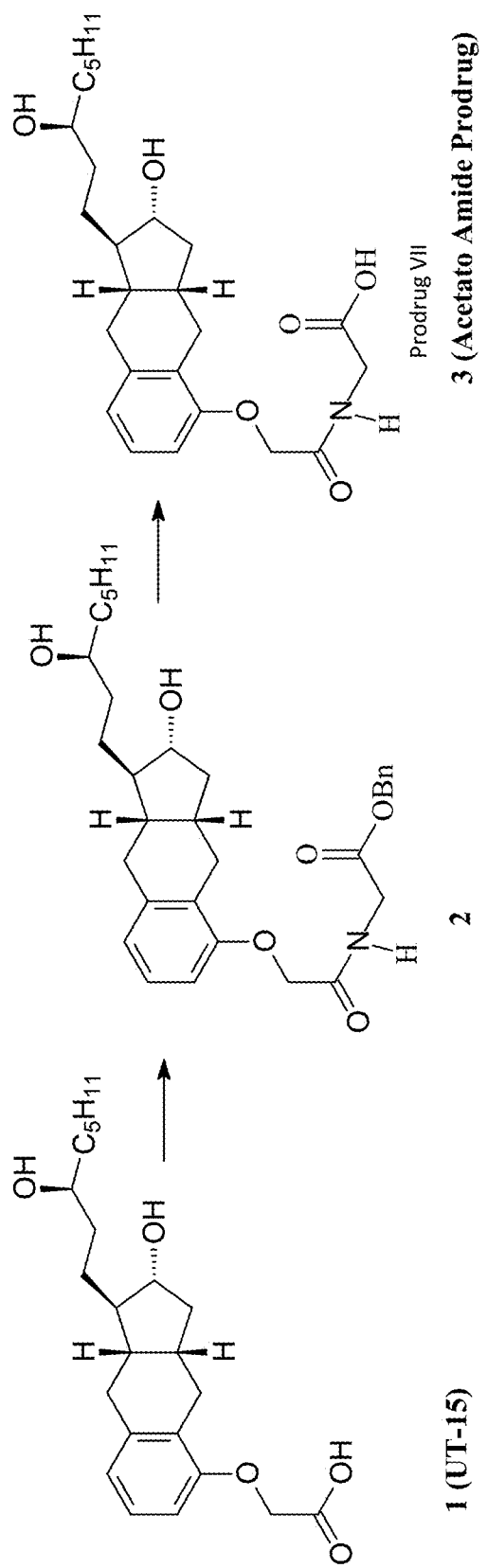
FIG. 5 is a scheme illustrating synthesis of acetate amide prodrug VII.

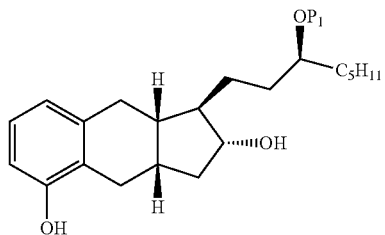

may be used for synthesizing cyclopentyl ring prodrugs of treprostinil, i.e. compounds with X being OH and $R_3$ being H, or side chain prodrugs of treprostinil, i.e. compounds with X being OH and $R_2$ being H. Synthesis of cyclopentyl ring prodrugs is illustrated in FIGS. 1 and 3, while synthesis of side chain prodrugs is shown in FIGS. 2 and 4.

For synthesizing the cyclopentyl ring prodrugs, the starting compound of the following formula

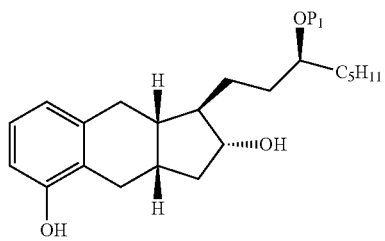

may be converted into a double-protected compound of the following formula:

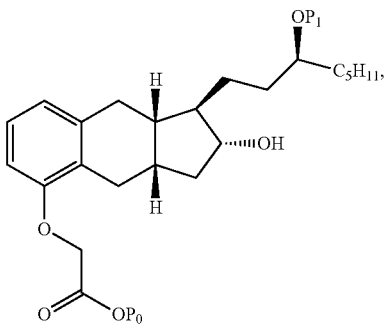

where $P_0$ is a hydroxyl protecting group, such as benzyl, substituted benzyl or al alkyl, such as $C_1$-$C_4$ alkyl, including methyl and ethyl. For example, the intermediate compound of the following formula

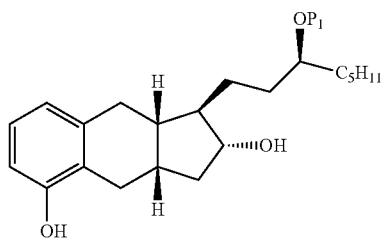

may be reacted with

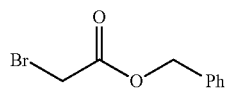

to form a double protected compound

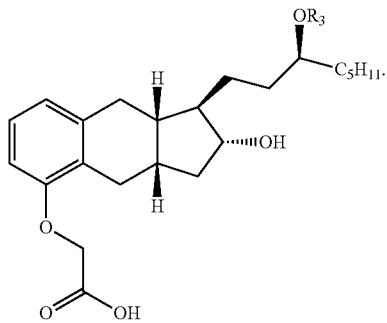

The double protected compound

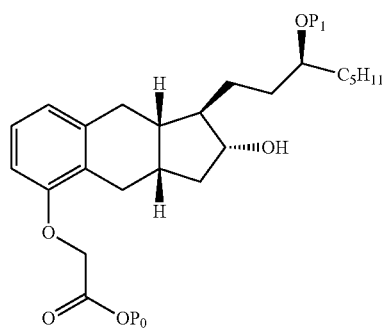

may be converted into a double protected prodrug compound of the following formula

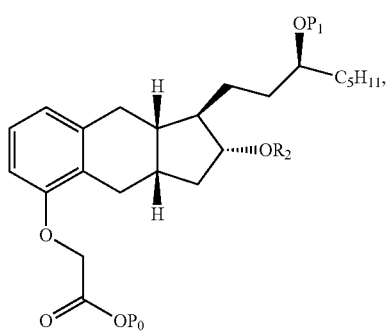

where $R_2$ may be

wherein Y is $OR_4$ or $NR_4R_5$, each of $R_4$ and $R_5$ is independently selected from H and $C_{1-4}$ alkyl, or Y is Cl, Br or $OCCl_3$. This may be accomplished by reacting the double protected compound with

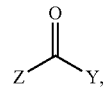

wherein Z is Cl, Br or $OCCl_3$. For example, when $R_2$ is

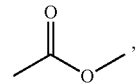

the double protected compound may be reacted with

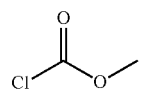

to form a respective double protected prodrug compound. When $R_2$ is

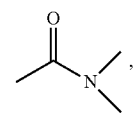

the double protected compound may be reacted

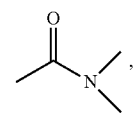

or a mix of $Cl_3CO\text{—}C(=O)\text{—}OCCl_3/HN(CH_3)\text{—}CH_3$ to form a respective double protected prodrug compound.

Each of $P_0$ and $P_1$ protecting groups may be then replaced with H to deprotect the carboxy group's hydroxyl and the side chain's hydroxyl. In some embodiments, such as the one illustrated in FIG. 1, deprotection of the carboxy group's hydroxyl and the side chain's hydroxyl (replacement of each of $P_0$ and $P_1$) may be performed in a single reaction. Yet in some other embodiments, deprotection of the carboxy group's hydroxyl and the side chain's hydroxyl in two separate reactions. In some cases, as illustrated in FIG. 3, the side chain's hydroxyl group may be deprotected first followed by deprotection of the carboxy group's hydroxyl. Yet in some other cases, the carboxy group's hydroxyl group may be deprotected first followed by deprotection of the side chain's hydroxyl. Deprotection of the side chain's hydroxyl may be performed in the presence of a lewis acid, such as $MgBr_2$, salts of copper, such as copper sulfate, acidic resins, such as amberlyst, mineral acids, such as HCl and $H_2SO_4$. Deprotection of hydroxyl protecting groups is disclosed "Green's protecting groups in organic synthesis" ISBN 978-0-471-69754-1, 4th edition, 2007, page 62; John Wiley and Sons). Deprotection of the carboxy group's hydroxyl may be performed for example, in the presence of one or more of a palladium carbon catalyst, platinum oxide and hydrogen gas.

For synthesizing the side chain prodrugs, the starting compound

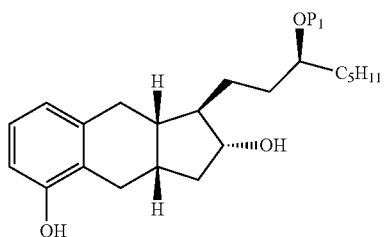

may be converted into a triple protected triol compound of the following formula:

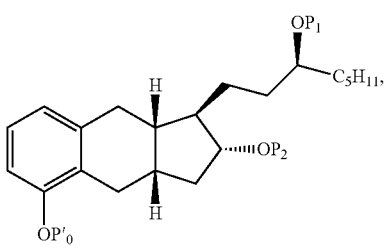

wherein P'$_0$ and P$_2$ may the same or different hydroxyl protecting group, which may be for example, a silyl protecting group, such as tert-Butyldimethylsilyl ether (TBDMS/TBS), Trimethylsilyl (TMS) Triethylsilyl (TES), tert-Butyldiphenylsilyl (TBDPS), Triisopropylsilyl (TIPS). In some embodiments, it may be preferred to have P'$_0$ and P$_2$ to be the same. For example, in FIGS. 2 and 4, the key intermediate compound is reacted with TBDMSCl to form a triple protected triol compound with both P'$_0$ and P$_2$ being TBDMS.

The triple protected triol compound may be then converted into a double protected triol compound of the following formula

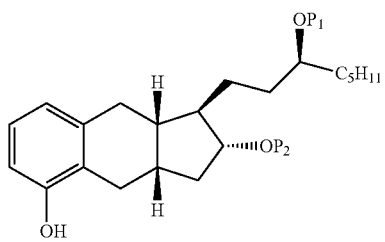

by deprotecting the conjugated ring's hydroxyl. Such conversion may be performed in the presence of a Li containing compound, such as LiOAc or LiOH.

The double protected triol compound may be converted then into a triple protected carboxy acid compound of the following formula

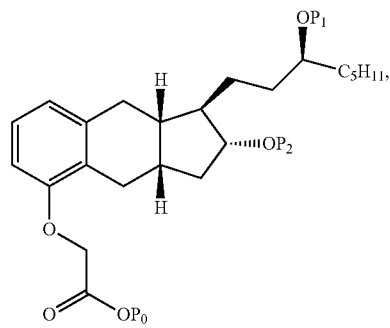

where P$_0$ is a hydroxyl protecting group, such as benzyl or a substituted benzyl. The double protected triol compound may be converted into a triple protected carboxy acid compound by reacting with

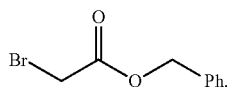

The triple protected carboxy acid compound may be then converted into a double protected carboxy acid compound of the following formula:

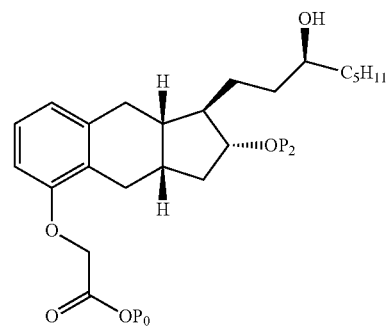

by deprotecting the side chain's hydroxyl's group. Deprotection of the side chain's hydroxyl may be performed in the presence of a lewis acid, such as MgBr$_2$, salts of copper, such as copper sulfate, acidic resins, such as amberlyst, mineral acids, such as HCl and H$_2$SO$_4$. Deprotection of hydroxyl protecting groups is disclosed "Green's protecting groups in organic synthesis" ISBN 978-0-471-69754-1, 4th edition, 2007, page 62; John Wiley and Sons).

The double protected carboxy acid compound may be then converted into a double protected prodrug compound of the following formula:

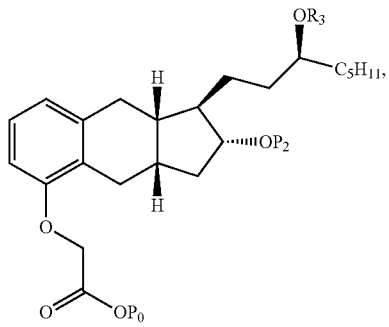

where $R_3$ may be

wherein Y is $OR_4$ or $NR_4R_5$, each of $R_4$ and $R_5$ is independently selected from H and $C_{1-4}$ alkyl, or Y is Cl, Br or $OCCl_3$. This may be accomplished by reacting the double protected carboxy acid compound with

where Z is Cl, Br or $OCCl_3$. For example, when $R_3$ is

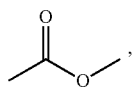

the double protected carboxy acid compound may be reacted with

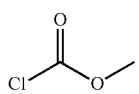

to form a respective double protected prodrug compound. When $R_3$ is

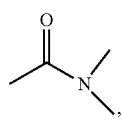

the double protected compound may be reacted

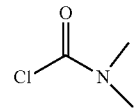

or a mix of $Cl_3CO$—$C(=O)$—$OCCl_3/HN(CH_3)$—$CH_3$ to form a respective double protected prodrug compound.

The double protected prodrug compound may converted into a side chain prodrug

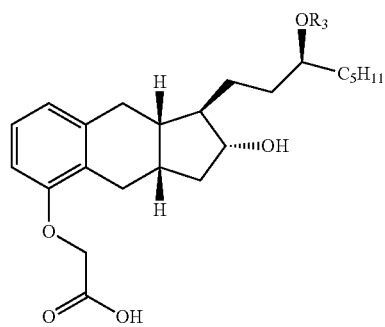

by deprotecting the cyclopentyl ring's hydroxyl and the carboxy group's hydroxyl. Deprotections of the cyclopentyl ring's hydroxyl and the carboxy group's hydroxyl may be performed in a single reaction or two separate reactions. In the latter case, deprotection of the cyclopentyl ring's hydroxyl may follow or precede deprotection of the carboxy group's hydroxyl. In FIGS. 2 and 4, deprotection of the cyclopentyl ring's hydroxyl and deprotection of the carboxy group's hydroxyl are performed as two separate reactions with the latter following the former. Deprotection of the carboxy group's hydroxyl may be performed in the presence of one or more of palladium, carbo, platinum oxide and hydrogen cgas. Deprotection of the cyclopentyl ring's hydroxyl may be performed in the presence of tetra-n-butylammonium fluoride (TBAF and n-Bu$_4$NF) or a mineral acid, such as HCl or $H_2SO_4$.

Treprostinil Amino Acid amide prodrugs, such as prodrugs J, K, L or M, may be prepared by reacting treprostinil with a protected amino acid, which is an amino acid in which hydrogen in its carboxy group is replaced with a hydroxyl protecting group, such as benzyl. As the result of such reaction a protected amino acid amide prodrug may be formed. The hydroxyl protecting group may be then removed from the protected amino acid amide prodrug to form a treprostinil amino acid amide prodrug, such as prodrugs J, K, L or M.

Embodiments described herein are further illustrated by, though in no way limited to, the following working examples.

WORKING EXAMPLES

Example 1

Synthesis of Treprostinil Carbamate Pro-Drugs

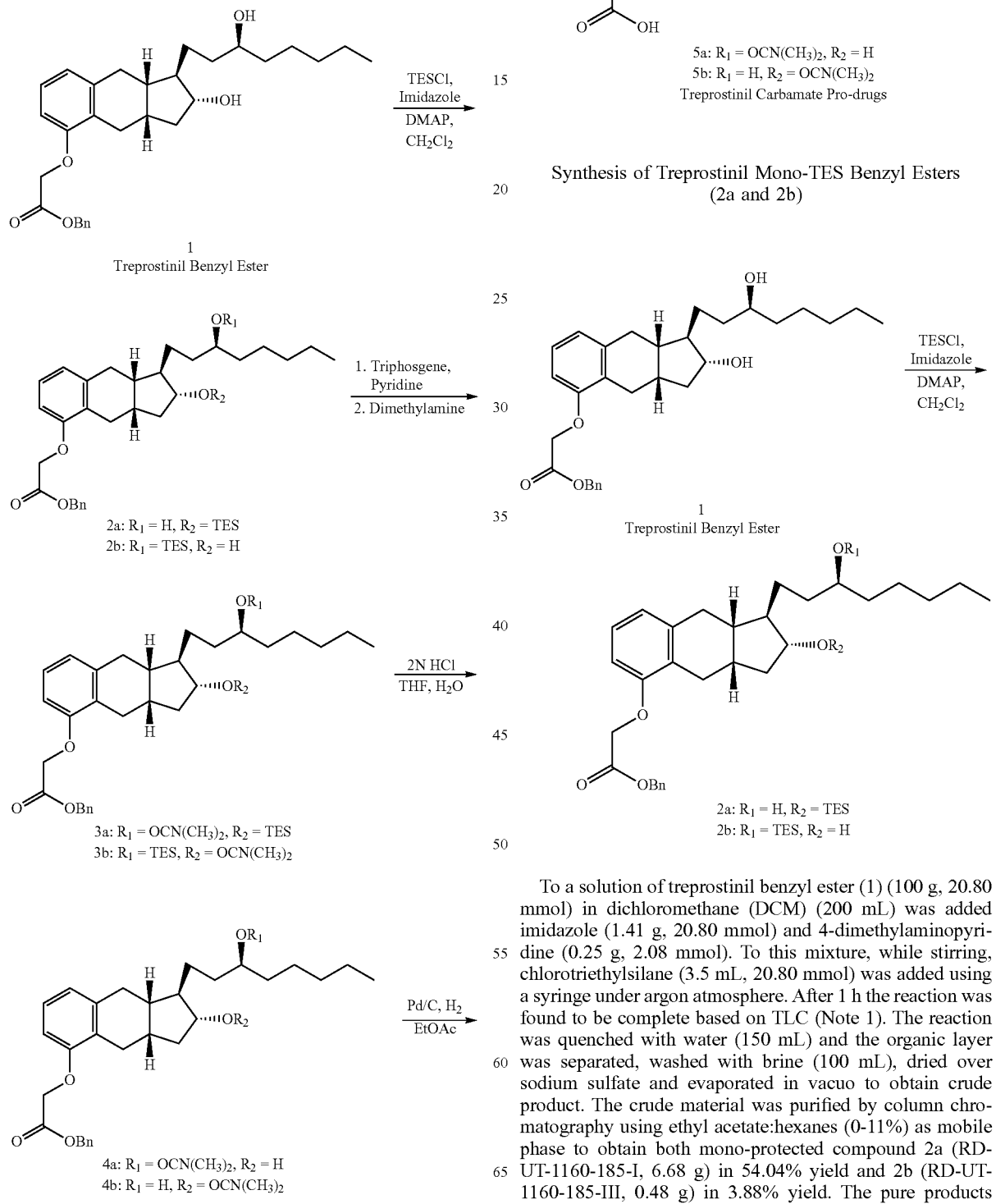

Synthesis of Treprostinil Mono-TES Benzyl Esters (2a and 2b)

To a solution of treprostinil benzyl ester (1) (100 g, 20.80 mmol) in dichloromethane (DCM) (200 mL) was added imidazole (1.41 g, 20.80 mmol) and 4-dimethylaminopyridine (0.25 g, 2.08 mmol). To this mixture, while stirring, chlorotriethylsilane (3.5 mL, 20.80 mmol) was added using a syringe under argon atmosphere. After 1 h the reaction was found to be complete based on TLC (Note 1). The reaction was quenched with water (150 mL) and the organic layer was separated, washed with brine (100 mL), dried over sodium sulfate and evaporated in vacuo to obtain crude product. The crude material was purified by column chromatography using ethyl acetate:hexanes (0-11%) as mobile phase to obtain both mono-protected compound 2a (RD-UT-1160-185-I, 6.68 g) in 54.04% yield and 2b (RD-UT-1160-185-III, 0.48 g) in 3.88% yield. The pure products were characterized by $^1$H NMR.

Note 1: A silica gel TLC was used to monitor the progress of the reaction using 20% EtOAc:Hexanes as mobile phase.

Experimental for Synthesis of Side Chain Carbamate Treprostinil Pro-Drug (5a)

Synthesis of TES Side Chain Carbamate Benzyl Ester (3a)

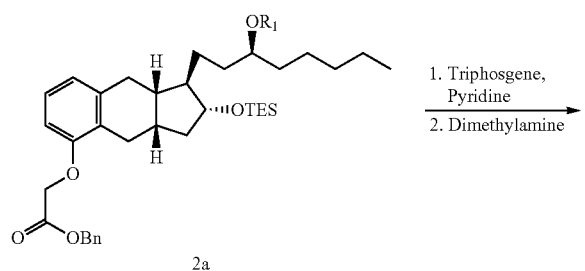

2a

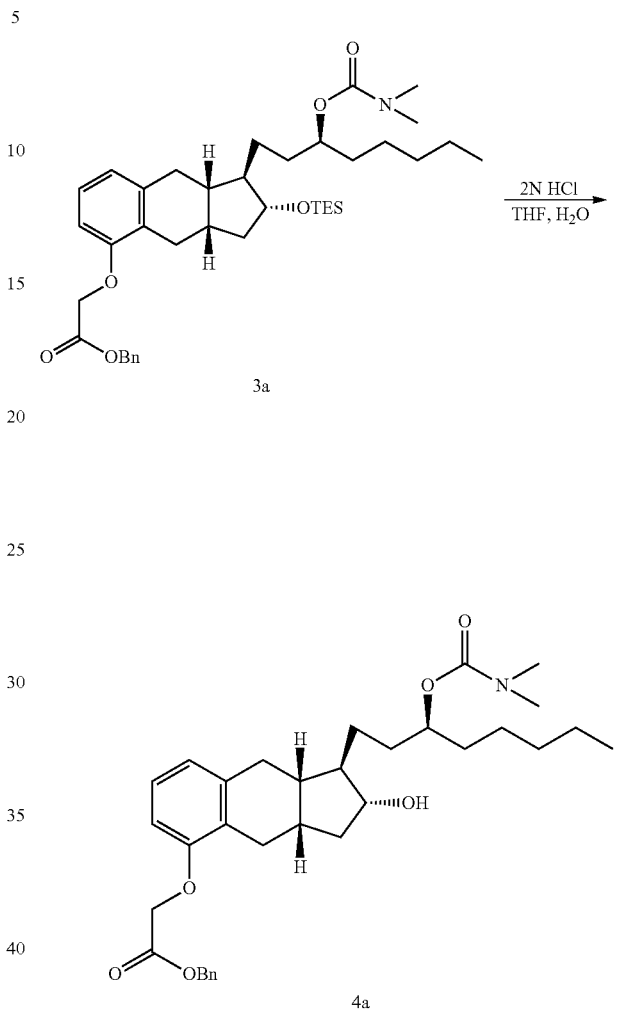

Synthesis of Side Chain Carbamate Benzyl Ester (4a)

3a

4a

To a solution of treprostinil mono-TES benzyl ester (2a) (0.5 g, 0.841 mmol) in 15 mL of toluene was added pyridine (0.14 mL, 1.682 mmol) and stirred under argon. To this an ice-cold solution of triphosgene (0.37 g, 1.261 mmol) in toluene (12 mL) was added drop-wise over a period of 0.5 h. After stirring for additional 0.5 h, reaction was found to be complete based on TLC (Note 1). The dropping funnel was charged with dimethylamine solution (2.0 M in THF) (6.0 mL) and added to the reaction mixture over a period of 0.5 h. After stirring for additional 1 h the reaction was found to be complete based on TLC (Note 1). The reaction was quenched with water (20 mL). The organic layer was separated and aqueous layer was extracted with MTBE (2×20 mL). The combined organic layers were washed with brine (20 mL), dried over sodium sulfate and evaporated in vacuo to obtain crude product. This was purified by column chromatography using ethyl acetate:hexanes (0 to 12%) as mobile phase to obtain pure TES side chain carbamate benzyl ester (3a) (RD-UT-1160-188, 0.32 g) and impure product (RD-UT-1160-188-Fr-22-23, 0.20 g) with a total yield of 93.4%. The pure product was characterized by $^1$H NMR.

Note 1: A silica gel TLC was used to monitor the progress of the reaction using 30% EtOAc:Hexanes as mobile phase.

To a solution of TES side chain carbamate benzyl ester (3a) (0.295 g, 0.443 mmol) in THF (20 mL) and water (4 mL) was added a 2N HCl aqueous solution (0.22 mL, 0.443 mmol). This was stirred at ambient temperature for 1 h upon which TLC showed completion of the reaction (Note 1). This reaction mixture was extracted with ethyl acetate (2×40 mL) and the combined organic layers were washed with water (20 mL), brine (20 mL), dried over sodium sulfate and evaporated in vacuo to obtain crude material. This was purified by column chromatography using ethyl acetate: hexanes (0 to 40%) as mobile phase to obtain pure side chain carbamate benzyl ester (4a) (RD-UT-1160-194, 0.26 g) a yield of 106.5% (with residual solvents). The pure product was characterized by $^1$H NMR and $^{13}$C NMR.

Note 1: A silica gel TLC was used to monitor the progress of the reaction using 60% EtOAc:Hexanes as mobile phase.

Synthesis of Side Chain Carbamate Treprostinil Pro-Drug (5a)

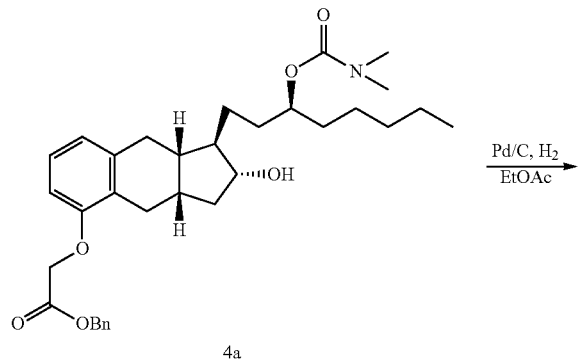

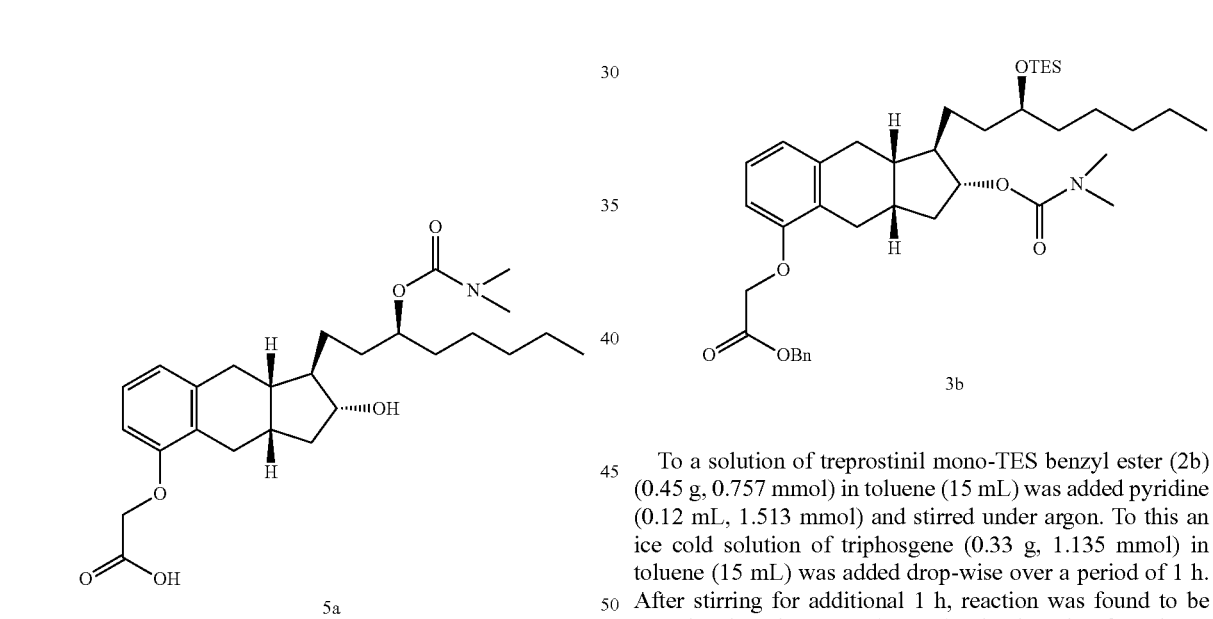

To a solution of side chain carbamate benzyl ester (4a) (0.25 g, 0.443 mmol) in ethyl acetate (15 mL) was added palladium on carbon (25 mg) and the reaction system was evacuated using vacuum and replaced with hydrogen gas under balloon pressure. This was stirred for 6 h at room temperature and the reaction was found to be complete based on TLC (Note 1). The reaction mixture was filtered through Celite and the filterate was evaporated in vacuo to obtain side chain carbamate treprostinil pro-drug (5a) (0.18 g) (RD-UT-1160-198) with 86.1% yield and 98.62% chemical purity (HPLC). The product was characterized by $^1$H NMR, $^{13}$C NMR, IR and LC-MS.

Note 1: A silica gel TLC was used to monitor the progress of the reaction using 60% EtOAc:Hexanes as mobile phase.

Experimental for Synthesis of Cyclopentyl Carbamate Treprostinil Pro-Drug (5b)

Synthesis of TES Cyclopentyl Carbamate Benzyl Ester (3b)

To a solution of treprostinil mono-TES benzyl ester (2b) (0.45 g, 0.757 mmol) in toluene (15 mL) was added pyridine (0.12 mL, 1.513 mmol) and stirred under argon. To this an ice cold solution of triphosgene (0.33 g, 1.135 mmol) in toluene (15 mL) was added drop-wise over a period of 1 h. After stirring for additional 1 h, reaction was found to be complete based on TLC (Note 1). The dropping funnel was charged with dimethylamine solution (2.0 M in THF) (6.0 mL) and added to the reaction mixture over a period of 0.5 h. After stirring for additional 1 h the reaction was found to be complete based on TLC (Note 1). The reaction was quenched with water (20 mL). The organic layer was separated and aqueous layer was extracted with MTBE (2×20 mL). The combined organic layers were washed with brine (20 mL), dried over sodium sulfate and evaporated in vacuo to obtain crude product. This was purified by column chromatography using ethyl acetate:hexanes (0 to 14%) as mobile phase to obtain pure TES cyclopentyl carbamate benzyl ester (3b) (RD-UT-1160-195, 0.44 g) with a yield of 87.5%. The pure product was characterized by $^1$H NMR.

Note 1: A silica gel TLC was used to monitor the progress of the reaction using 30% EtOAc:Hexanes as mobile phase.

Synthesis of Cyclopentyl Carbamate Benzyl Ester (4b)

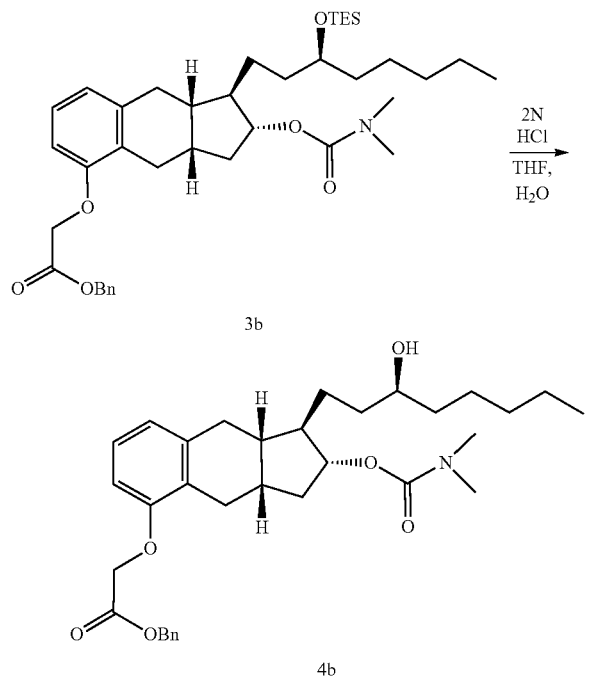

To a solution of TES cylcopentyl carbamate benzyl ester (3b) (0.42 g, 0.631 mmol) in THF (12 mL) and water (3 mL) was added a 2N HCl aqueous solution (0.31 mL, 0.631 mmol). This was stirred at ambient temperature for 1 h upon which TLC showed completion of the reaction (Note 1). This reaction mixture was extracted with ethyl acetate (2×30 mL) and the combined organic layers were washed with brine (20 mL), dried over sodium sulfate and evaporated in vacuo to obtain crude material. This was purified twice by column chromatography using ethyl acetate:hexanes (0 to 40%) as mobile phase to obtain pure cyclopentyl carbamate benzyl ester (4b) (RD-UT-1160-205, 0.32 g) a yield of 93.4%. The pure product was characterized by $^1$H NMR, $^{13}$C NMR.

Note 1: A silica gel TLC was used to monitor the progress of the reaction using 60% EtOAc:Hexanes as mobile phase.

Synthesis of Cyclopentyl Carbamate Treprostinil Pro-Drug (5b)

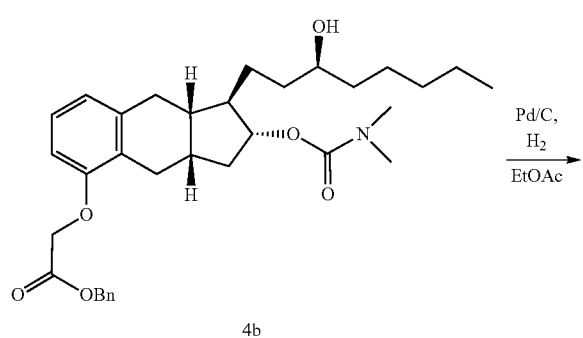

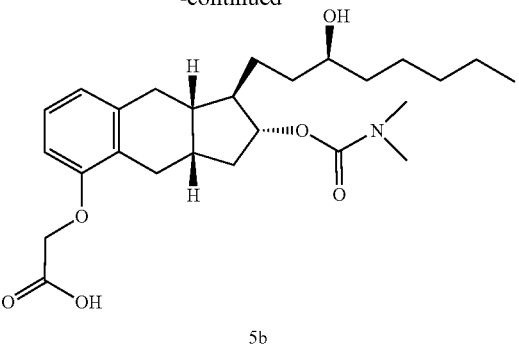

To a solution of cyclopentyl carbamate benzyl ester (4b) (0.31 g, 0.562 mmol) in 15 mL of ethyl acetate was added palladium on carbon (30 mg) and the reaction system was evacuated using vacuum and replaced with hydrogen gas under balloon pressure. This was stirred for 6 h at room temperature and the reaction was found to be complete based on TLC (Note 1). The reaction mixture was filtered through Celite and evaporated in vacuo to obtain cyclopentyl carbamate treprostinil pro-drug (5b) (0.24 g) (RD-UT-1160-198) in 92.6% yield and 99.39% chemical purity (HPLC). The product was characterized by $^1$H NMR, $^{13}$C NMR, IR and LC-MS.

Note 1: A silica gel TLC was used to monitor the progress of the reaction using 60% EtOAc:Hexanes as mobile phase.

Example 2

Synthesis of Treprostinil Glycolamide Prodrug (Prodrug VII)

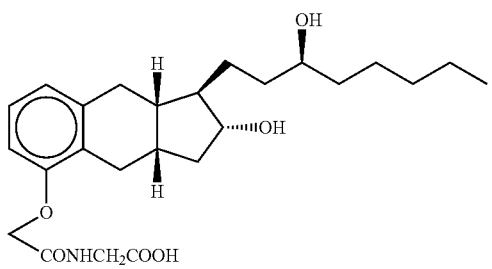

Discussion

Two methods for the synthesis of glycolamide prodrug (Scheme 2) were explored: first, via the reaction of treprostinil (UT-15) and glycine methyl ester to obtain amide intermediate Amide I followed by NaOH hydrolysis; second, via the reaction of UT-15 with glycine benzyl ester p-toluenesulfonate to form the amide intermediate Amide II followed by hydrogenation. The first route involved strong basic conditions for the hydrolysis step and caused the hydrolysis of both ester bond and amide bond and lead to the formation of UT-15. The second route involved non-basic hydrogenolysis for the de-benzylation of Amide II and provided clean desired product without any amide bond cleavage and did not lead to the formation of UT-15. Finally, the second route was used to make glycolamide prodrug of treprostinil (Prodrug VII).

Scheme 2: Synthesis of Glycolamide Prodrug

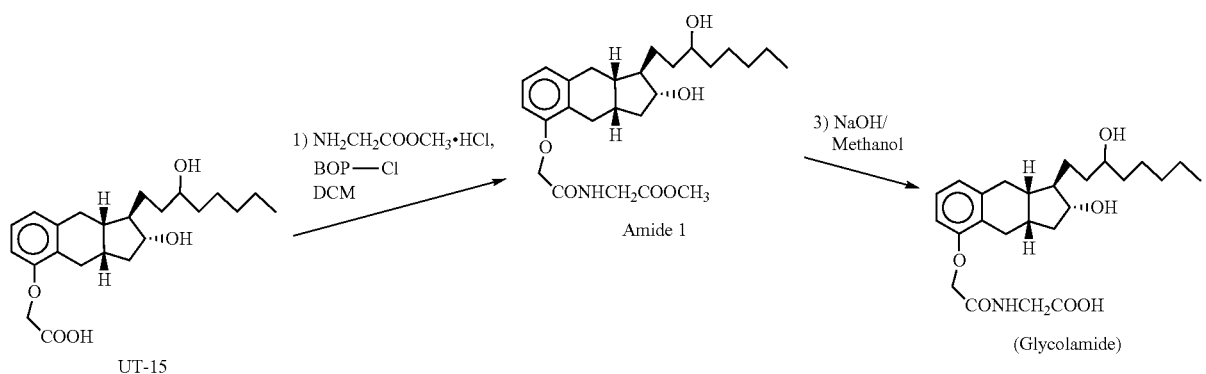

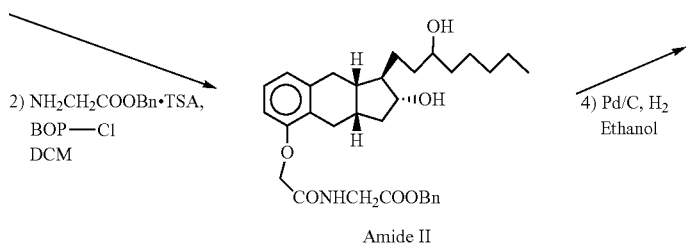

Step 1: Synthesis of Amide II

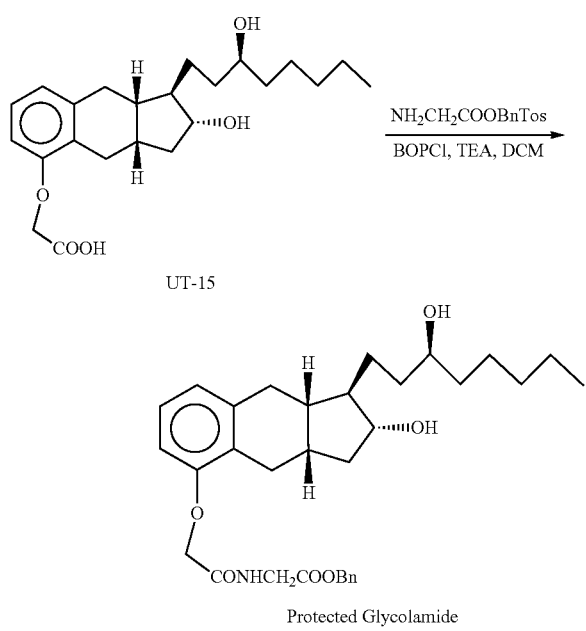

A 50 ml round bottom flask equipped with magnetic stir bar was charged with a solution of UT-15 (0.5 g, 1.28 mmol) in anhydrous DCM (20 ml) under argon. To this solution was added Bop-Cl (0.49 g, 1.92 mmol) followed by glycine benzyl ester p-toluenesulfonate (0.43 g, 1.28 mmol) at room temperature under argon. The reaction mixture was stirred for 20 minutes, then the triethylamine (0.39 g, 3.84 mmol) was added. The reaction mixture was stirred overnight until the reaction was complete. The progress of reaction was checked by tlc. The reaction was quenched with 0.1N HCl (10 ml), the DCM layer was separated and washed with 10% $NaHCO_3$ (10 ml), water (10 ml) and brine (10 ml), dried over anhydrous $Na_2SO_4$, filtered and concentrated in vacuo to obtain crude product (0.9 g, RD-UT-1161-101). The crude product was purified on silica gel using a gradient solvent of 30-60% EtOAc in hexanes to obtain pure product (Amide II) (0.396 g, RD-UT-1161-101B). The compound was characterized by $^1$H NMR.

Step 2: Synthesis of Glycolamide Prodrug (Prodrug VII)

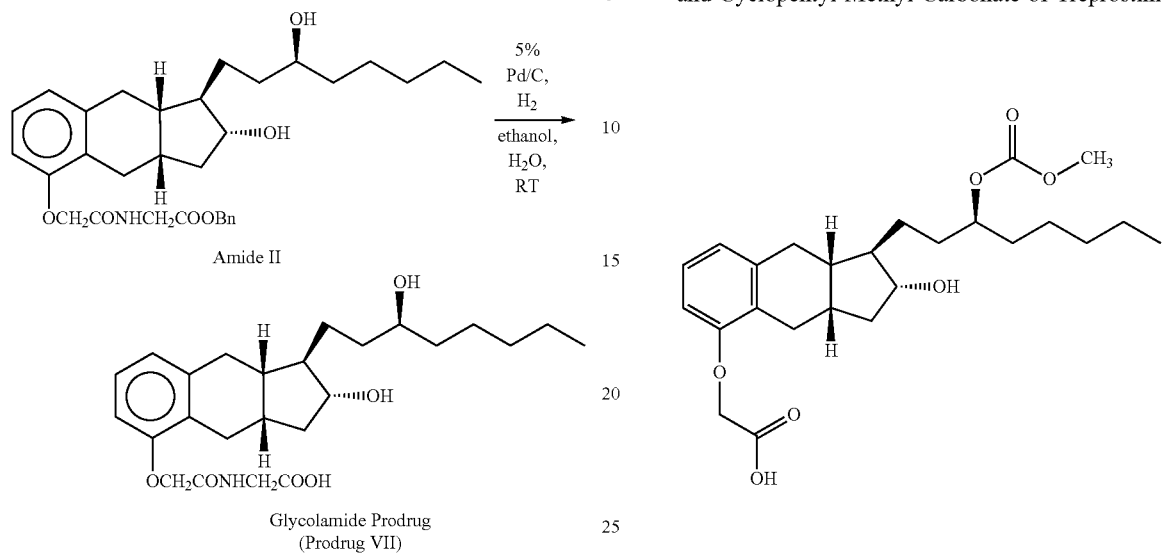

Amide II

Glycolamide Prodrug (Prodrug VII)

A 50 ml round bottom flask equipped with magnetic stir bar was charged with a solution of amide II (250 mg, 0.465 mmol) in ethanol (30.0 ml). The reaction mixture was evacuated air with argon for three times, then 5% Pd—C (75 mg) was added and replaced argon with $H_2$ for three times. The reaction mixture was pressured with $H_2$ using balloon and left at room temperature. The reaction mixture was stirred for 1 hr and the progress of reaction was checked by tlc (EtOAc). The reaction mixture was passed through a Celite pad, and the Celite pad was washed with ethanol (50 ml). The combined ethanol solution was concentrated under vacuo to obtain product Glycolamide (191 mg, RD-UT-1161-121) as white foam. The compound was characterized by $^1$H NMR, $^{13}$C NMR, IR and MS. The HPLC purity was 98.77% and no free UT-15 was observed.

Example 3

Syntheses of Prodrugs of Treprostinil: Side Chain and Cyclopentyl Methyl Carbonate of Treprostinil

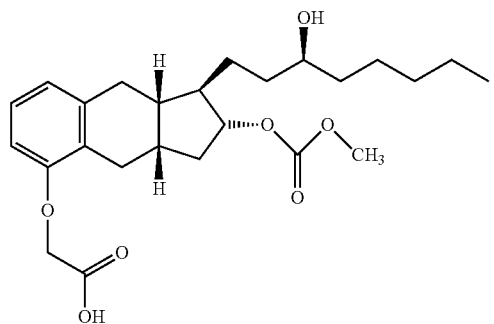

Side chain methyl carbonate prodrug of treprostinil (left) and cyclopentyl methyl carbonate of treprostinil (right) are presented above.

Scheme 3. Synthesis of Side Chain Methyl Carbonate of Treprostinil (6)

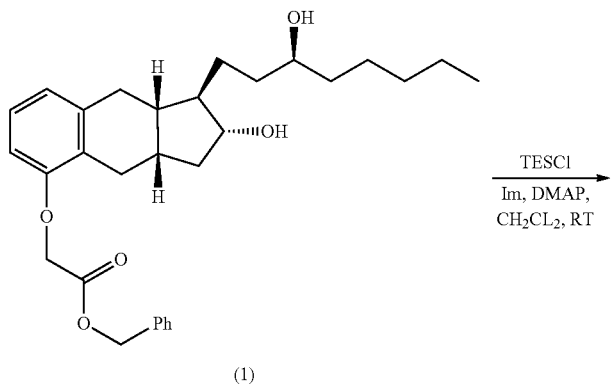

-continued
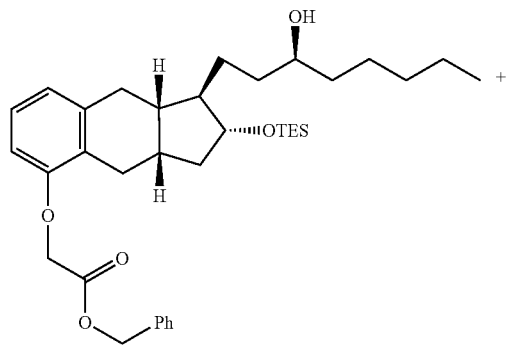 (2)
+
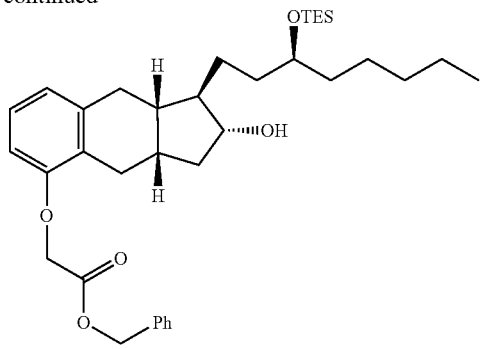 3
(3)
separated by chromatography
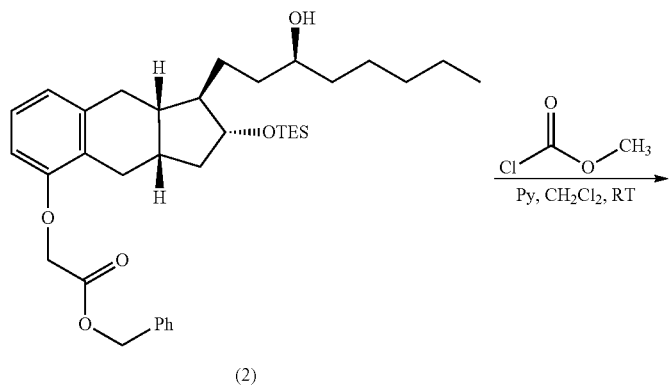
(2)
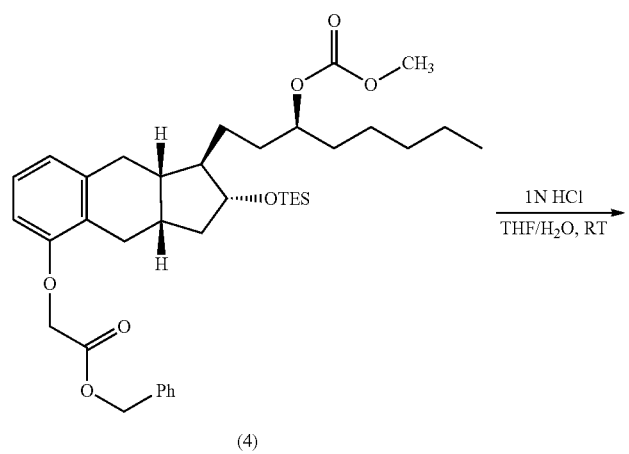
(4)

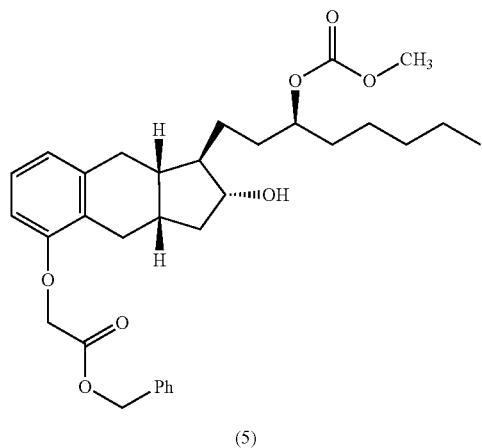
(5)
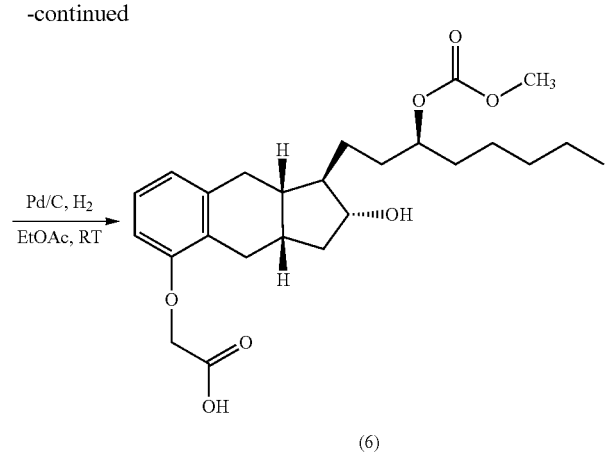
(6)
Scheme 4. Synthesis of Cyclopentyl Methyl Carbonate of Treprostinil (9)
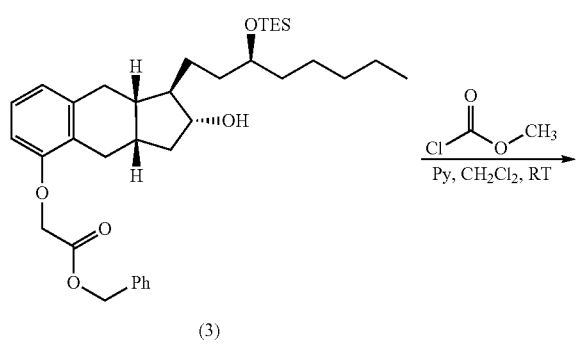
(3)
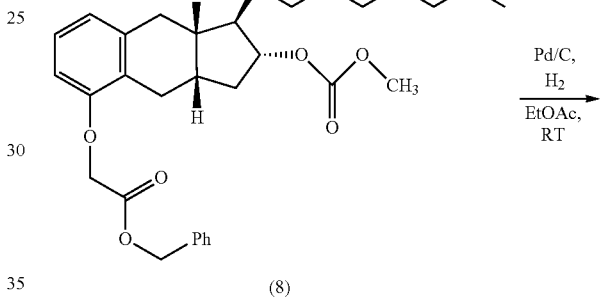
(8)
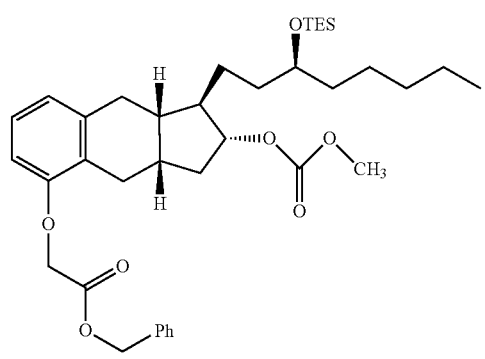
(7)
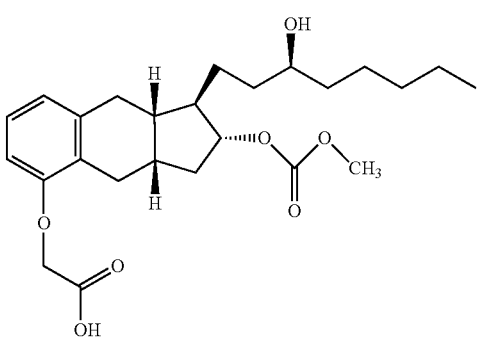
(9)

Experimental

Syntheses of Mono-TES Protected Treprostinil Benzyl Ester (2 and 3)

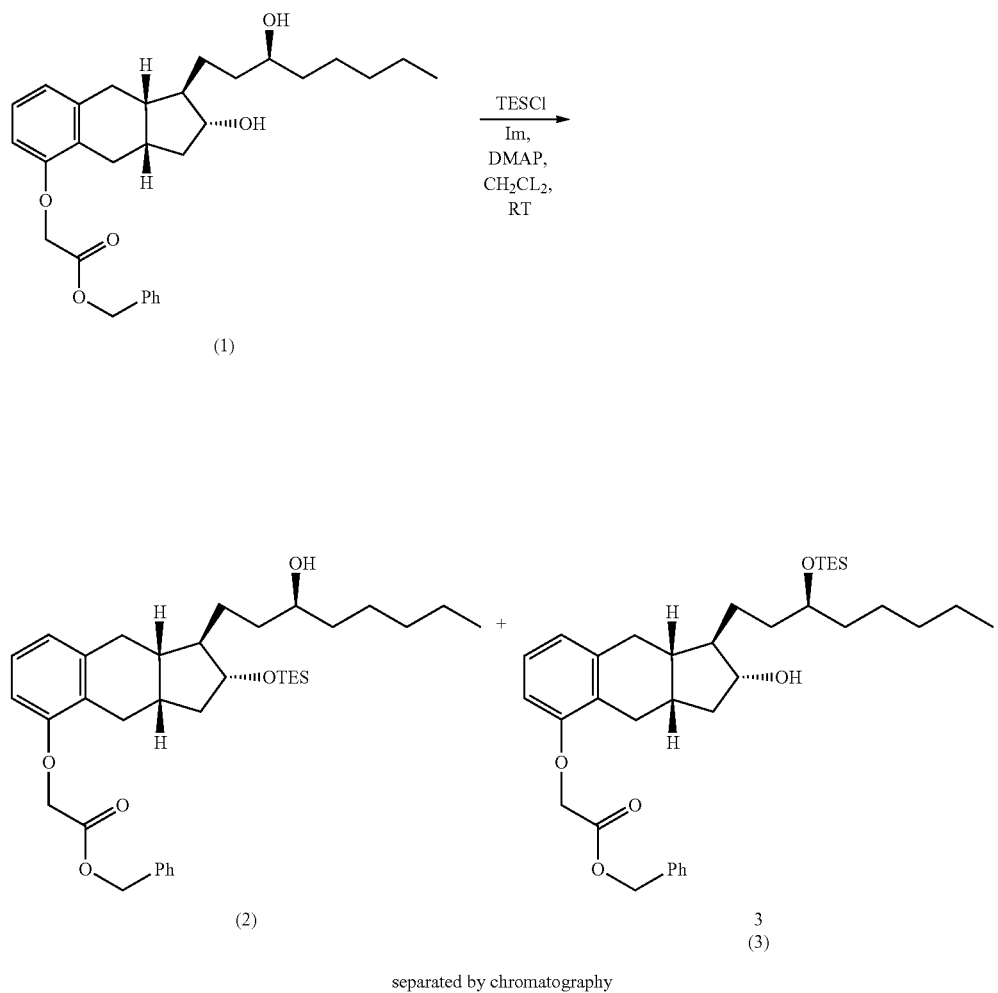

separated by chromatography

To a solution of treprostinil benzyl ester (1) (5.06 g, 10.53 mmol) in anhydrous dichloromethane (100 mL) was added imidazole (0.72 g, 10.57 mmol) and 4-(dimethylamino)pyridine (DMAP) (0.13 g, 1.06 mmol) at room temperature. To this clear solution was added dropwise a solution of chlorotriethylsilane (1.59 g, 1.77 mL, 10.55 mmol) in anhydrous dichloromethane (30 mL) over period of 1 h at room temperature under argon. After complete addition, the reaction mixture was stirred for 4.5 h and checked tlc (EtOAc/Hexane, 1:4). The reaction mixture was quenched with water (50 mL) and separated the dichloromethane layer. The dichloromethane layer was washed with water (1×50 mL), brine (1×20 mL), dried (Na$_2$SO$_4$), filtered and concentrated in vacuo to give a light yellow viscous liquid (6.95 g) (Lot #D-1166-160). The crude product was chromatographed on silica gel (265 g) column using ethyl acetate in hexane (2-20%) to give di-TES protected treprostinil benzyl ester (1.59 g, Lot #D-1166-160-A), cyclopentyl-TES protected treprostinil benzyl ester (2) (2.95 g, Lot #D-1166-160-B) and side chain-TES protected treprostinil benzyl ester (3) (0.55 g, Lot #D-1166-160-D). Both mono-TES protected compounds (2 and 3) were characterized by spectral data (IR, $^1$H NMR and MS).

Synthesis of Cyclopentyl-TES Side Chain Methyl Carbonate Treprostinil Benzyl Ester (4)

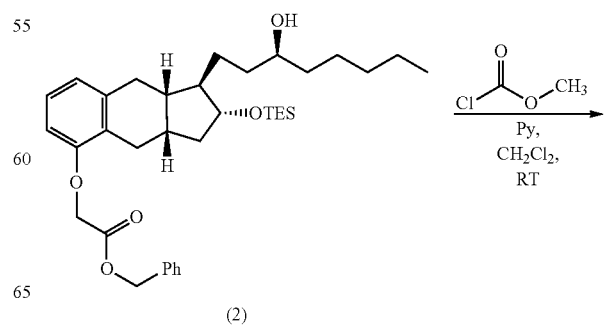

(2)

-continued

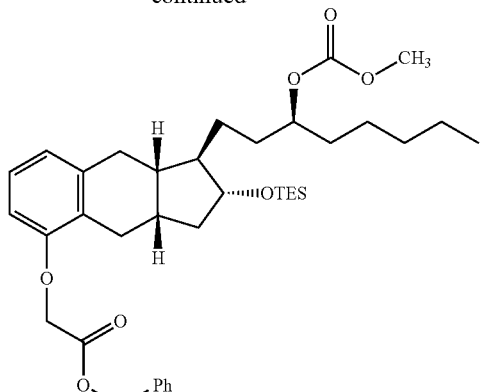

(4)

-continued

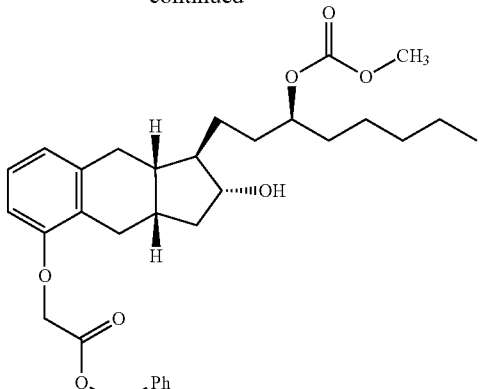

(5)

To a solution of cyclopentyl-TES protected treprostinil benzyl ester (2) (0.84 g, 1.41 mmol) in anhydrous pyridine (4.0 mL) was added dropwise a solution of methyl chloroformate (1.33 g, 1.09 mL, 14.1 mmol) in anhydrous dichloromethane (4.0 mL) at 0° C. to 5° C. over a period of 5 min under argon. After complete addition, the reaction mixture was stirred at 0° C. to room temperature overnight. After 20 h, the reaction mixture was checked by tlc (EtOAc/Hexane, 1:4) and the reaction was complete. The mixture was treated with water (20 mL) and then extracted with dichloromethane (3×25 mL). The combined dichloromethane extracts were washed with water (1×20 mL), brine (1×10 mL), dried (Na$_2$SO$_4$), filtered and concentrated in vacuo to give crude product as a light pink viscous liquid (0.88 g) (Lot #D-1166-189). The crude product was chromatographed on silica gel (35 g) column using ethyl acetate in hexane (2-10%) to give cyclopentyl-TES side chain methyl carbonate treprostinil benzyl ester (4) as a pale yellow viscous liquid (0.69 g) (Lot #D-1166-189-B). The pure compound was characterized by spectral data (IR, $^1$H NMR, $^{13}$C NMR and MS) and purity (94.58%, AUC) by HPLC.

Synthesis of Side Chain Methyl Carbonate Treprostinil Benzyl Ester (5)

To a solution of cyclopentyl-TES side chain methyl carbonate treprostinil benzyl ester (4) (0.307 g, 0.470 mmol) in a mixture of tetrahydrofuran (10 mL) and water (2 mL) (ratio of THF:H$_2$O=5:1) was added 1N hydrochloric acid (0.71 mL, 0.71 mmol) at room temperature. The reaction mixture was stirred at room temperature for 30 min and checked tlc (EtOAc/Hexane, 3:7). The reaction was complete and mixture was neutralized with saturated sodium bicarbonate (1 mL) to pH 7-8 and then diluted with water (10 mL). The mixture was extracted with MTBE (3×15 mL). The combined MTBE extracts were washed with water (2×10 mL), brine (1×10 mL), dried (Na$_2$SO$_4$), filtered and concentrated in vacuo to give a clear viscous liquid (0.37 g) (Lot #D-1166-203). The crude product (0.031 g) from other reaction (Lot #D-1166-201) was combined with this lot for purification. The combined crude product was chromatographed on silica gel (16 g) column using ethyl acetate in hexane (5-30%) to give side chain methyl carbonate treprostinil benzyl ester (5) as a clear viscous liquid (0.252 g) (Lot #D-1166-203-B). The pure compound was characterized by spectral data (IR, $^1$H NMR, $^{13}$C NMR and MS) and purity (99.83%, AUC) by HPLC.

Synthesis of Side Chain Methyl Carbonate of Treprostinil (6)

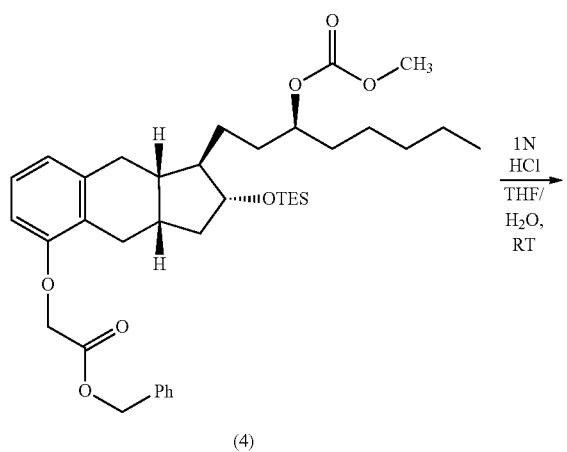

(4)

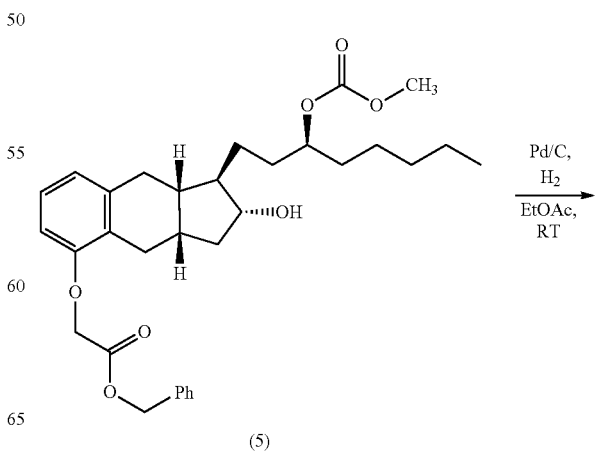

(5)

53
-continued

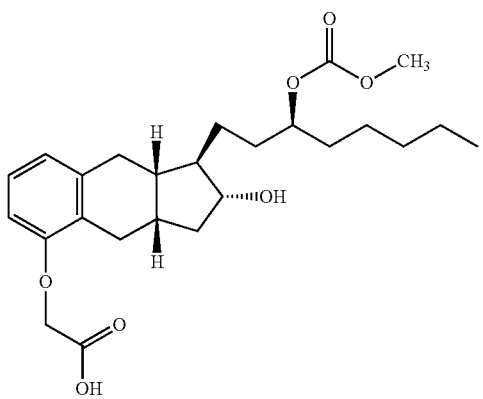

(6)

To a solution of side chain methyl carbonate treprostinil benzyl ester (5) (0.23 g, 0.427 mmol) in ethyl acetate (10 mL) was added palladium on carbon (5 wt %, 50% wet) (0.12 g). The mixture was stirred and evacuated under house vacuum and replaced by hydrogen (filled in balloon). The process was repeated three times. The mixture was stirred at room temperature under the atmosphere of hydrogen for 2 h and checked tlc (EtOAc/Hexane, 3:7 and EtOAc, 100%). The reaction was complete. The reaction mixture was treated with Celite (1.0 g) and the filtered through a pad of Celite (2.0 g) in a disposable polyethylene frit with Whatman filter No. 50, and the solid was washed with ethyl acetate (3×10 mL). The combined ethyl acetate filtrate was evaporated in vacuo to give side chain methyl carbonate of treprostinil (6) as a gray-white foamy solid (0.188 g) (Lot #D-1166-206). The compound was fully characterized by spectral data (IR, $^1$H NMR, $^{13}$C NMR and MS) and purity (99.64%, AUC) by HPLC.

Synthesis of Side Chain-TES Cyclopentyl Methyl Carbonate Treprostinil Benzyl Ester (7)

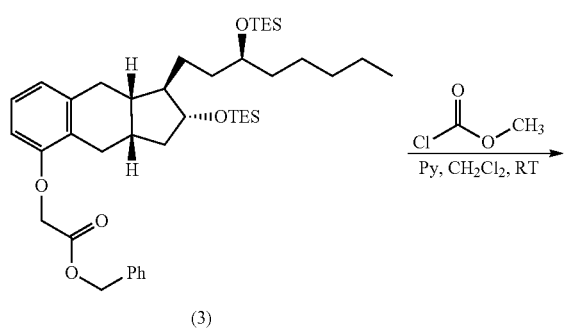

(3)

54
-continued

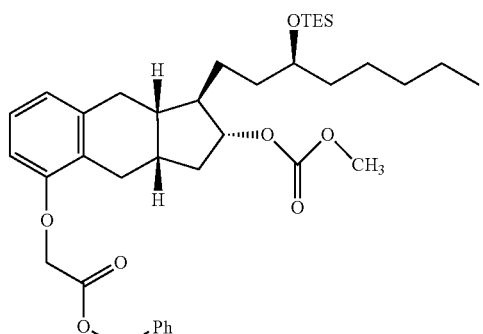

(7)

To a solution of side chain-TES protected treprostinil benzyl ester (3) (0.28 g, 0.47 mmol) in anhydrous pyridine (2.0 mL) was added dropwise a solution of methyl chloroformate (0.44 g, 0.36 mL, 4.66 mmol) in anhydrous dichloromethane (2.0 mL) at 0° C. to 5° C. over a period of 5 min under argon. After complete addition, the reaction mixture was stirred at 0° C. to room temperature overnight. After 17 h, the reaction mixture was checked by tlc (EtOAc/Hexane, 1:4) and the reaction was complete. The mixture was treated with water (10 mL) and MTBE (15 mL). The organic layer was separated and washed with water (2×15 mL), 5% citric acid (2×10 mL), water (1×10 mL), brine (1×5 mL), dried (Na$_2$SO$_4$), filtered and concentrated in vacuo to give give side chain-TES cyclopentyl methyl carbonate treprostinil benzyl ester (7) as a pale yellow viscous liquid (0.285 g) (Lot #D-1166-187). The compound was characterized by spectral data (IR, $^1$H NMR, $^{13}$C NMR and MS) and purity (74.27%, AUC) by HPLC.

Synthesis of Cyclopentyl Methyl Carbonate Treprostinil Benzyl Ester (8)

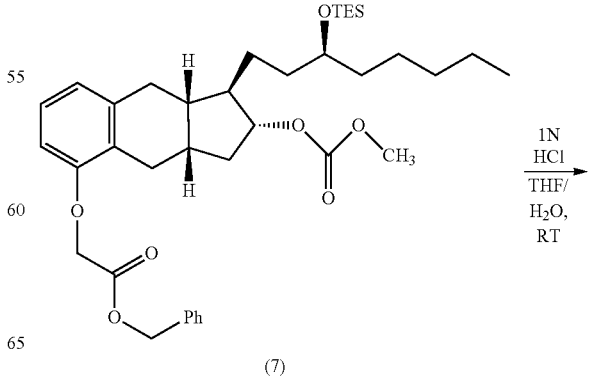

(7)

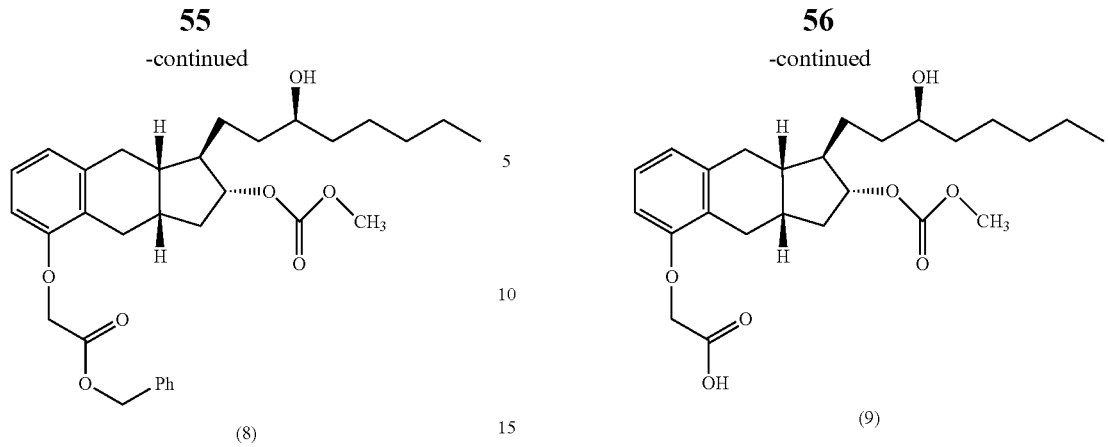

(8)    (9)

To a solution of side chain-TES cyclopentyl methyl carbonate treprostinil benzyl ester (7) (0.27 g, 0.413 mmol) in a mixture of tetrahydrofuran (10 mL) and water (2 mL) (ratio of THF:H$_2$O=5:1) was added 1N hydrochloric acid (0.62 mL, 0.62 mmol) at room temperature. The reaction mixture was stirred at room temperature for 20 min and checked tlc (EtOAc/Hexane, 1:4 and 3:7). The reaction was complete and mixture was neutralized with saturated sodium bicarbonate (1 mL) to pH 7-8 and then diluted with water (10 mL). The mixture was extracted with MTBE (3×15 mL). The combined MTBE extracts were washed with water (2×10 mL), brine (1×10 mL), dried (Na$_2$SO$_4$), filtered and concentrated in vacuo to give a clear viscous liquid (0.24 g) (Lot #D-1174-001). The crude product was chromatographed on silica gel (18 g) column using ethyl acetate in hexane (5-30%) to give cyclopentyl methyl carbonate treprostinil benzyl ester (8) as a clear viscous liquid/white semi-solid (0.19 g) (Lot #D-1174-001-B). The pure compound was characterized by spectral data (IR, $^1$H NMR, $^{13}$C NMR and MS) and purity (98.45%, AUC) by HPLC.

Synthesis of Cyclopentyl Methyl Carbonate of Treprostinil (9)

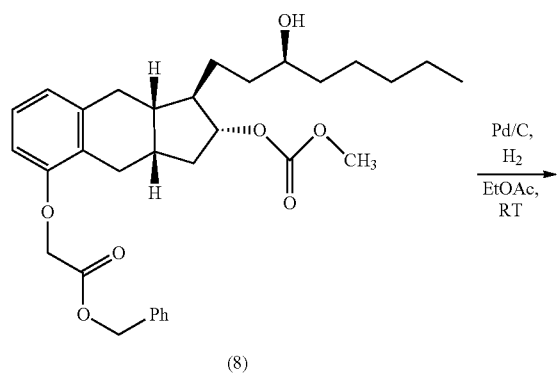

(8)

To a solution of cyclopentyl methyl carbonate treprostinil benzyl ester (8) (0.16 g, 0.297 mmol) in ethyl acetate (10 mL) was added palladium on carbon (5 wt %, 50% wet) (0.08 g). The mixture was stirred and evacuated under house vacuum and replaced by hydrogen (filled in balloon). The process was repeated three times. The mixture was stirred at room temperature under the atmosphere of hydrogen for 2 h and checked tlc (EtOAc/Hexane, 3:7 and EtOAc, 100%). The reaction was complete. The reaction mixture was treated with Celite (1.0 g) and the filtered through a pad of Celite (2.0 g) in a disposable polyethylene frit with Whatman filter No. 50, and the solid was washed with ethyl acetate (3×10 mL). The combined ethyl acetate filtrate was evaporated in vacuo to give cyclopentyl methyl carbonate of treprostinil (9) as a white viscous liquid/semi-solid (0.138 g) (Lot #D-1174-004). The compound was fully characterized by spectral data (IR, $^1$H NMR, $^{13}$C NMR and MS) and purity (98.97%, AUC) by HPLC.

Example 4

In Vitro Receptor Activity of Treprostinil and its Prodrugs

Prodrugs I, II, III, IV, VII, and IX (for structures see FIGS. 7 and 39) as well as treprostinil were tested for 3 G-protein-coupled receptors (GPCRs), namely DP1, EP2, and IP, using cyclin adenosine monophosphate (cAMP) assay.

Materials. Cells and control agonists: Cells and control agonists used in the study are summarized in Table 1.

TABLE 1

Cell Lines and Control Agonists Used in the Study

| Species | Target | Parental | Catalog # | Assays | Control agonist |
|---|---|---|---|---|---|
| Human | DP1 | HEK293T | C1200 | cAMP | PGD2 |
| Human | EP2 | HEK293T | C1202 | cAMP | Iloprost |
| Human | IP1 | CHO-K1 | C1206-1 | cAMP | Iloprost |

Compounds were provided in powder form. The compounds were reconstituted in DMSO at a concentration of 10 mM.

Cyclic AMP assay kit: HTRF cAMP HiRange Kit (CisBio, Cat #62AM6PEC).

Instruments: FlexStation III (Molecular Devices).

Methods

Cyclic AMP (cAMP) Assay: cAMP assays were performed according to the manufacturer's protocol using Cis- Bio's HTRF cAMP HiRange Kit. For Gs pathway assay in agonist mode, cells were incubated with compounds in 384 well plates for 20 minutes at 37° C. The reaction was terminated by sequentially adding D2-labeled cAMP and cryptate-labeled anti-cAMP antibody in lysis buffer. The plate was then incubated at room temperature for 60 minutes before reading fluorescent emissions at 620 nm and 668 nm with excitation at 314 nm on FlexStation III (Molecular Devices).

Data Analysis

Cyclic AMP (cAMP) assays: Cyclic AMP assay results are shown as "Ratio 668/620×10,000" (ratio of fluorescence at 668 nm and 620 nm×10,000). Data in graphs are represented in Mean±SD. Dose-dependent responses were fitted with sigmoidal dose-response curves allowing variable slopes using GraphPad Prism versions 4, 5 or 6 (Graphpad Prism).

Results

All compounds and control agonists displayed dose response activity in DP1, EP2, and IP1 receptor expressing cells. EC50 (a drug concentration that gives half-maximal response) values determined from the dose-dependent responses is presented in Table 2.

TABLE 2

Receptor activity (EC50, M) for treprostinil and its prodrugs.

| Compound | IP receptor | EP receptor | DP receptor |
|---|---|---|---|
| Treprostinil | $2.28 \times 10^{-9}$ | $6.75 \times 10^{-9}$ | $7.07 \times 10^{-10}$ |
| Prodrug I | $8.07 \times 10^{-6}$ | $1.80 \times 10^{-6}$ | $4.85 \times 10^{-7}$ |
| Prodrug II | $3.05 \times 10^{-7}$ | $1.64 \times 10^{-6}$ | $1.18 \times 10^{-7}$ |
| Prodrug III | $4.79 \times 10^{-7}$ | $4.35 \times 10^{-7}$ | $7.34 \times 10^{-8}$ |
| Prodrug IV | $4.0 \times 10^{-7}$ | $4.55 \times 10^{-6}$ | $1.43 \times 10^{-7}$ |
| Prodrug VII | $2.0 \times 10^{-6}$ | $7.4 \times 10^{-4}$ | $4.22 \times 10^{-7}$ |
| Prodrug IX | $1.58 \times 10^{-6}$ | $1.35 \times 10^{-6}$ | $1.62 \times 10^{-7}$ |

The data in Table 2 demonstrates that each of the studied prodrugs was significantly less potent than treprostinil against DP1, EP2 and IP1. Although the present invention is not limited by a theory of its operation, the site pain observed during subcutaneous administering of treprostinil may be due to treprostinil affecting one or more of the IP receptor, the DP receptor and the EP receptor in the subcutaneous tissue. Because the studied prodrugs are less potent against each of the IP receptor, the DP receptor and the EP receptor than treprostinil, these prodrugs may cause less site pain when administered subcutaneously.

Example 5

Evaluation of Prodrug XV Against Human G Protein Coupled Receptors

Prodrug XV (for structure see FIG. 10) as well as treprostinil were tested for 3 G-protein-coupled receptors (GPCRs), namely DP1, EP2, and IP, using cyclic adenosine monophosphate (cAMP) assay.

Materials. Cells and control agonists: Cells and control agonists used in the study are summarized in Table 1.

Compounds were provided 2 compounds in powder form. The compounds were reconstituted in DMSO at a concentration of 10 mM.

Cyclic AMP assay kits: Multiscreen™ TR-FRET cAMP 1.0 No Wash Assay Kit (Multispan, Inc., Cat #MSCM01-25) and HTRF cAMP HiRange Kit (CisBio, Cat #62AM6PEC). Instruments: FlexStation III (Molecular Devices).

Methods

Cyclic AMP (cAMP) Assay: cAMP assays were performed according to the manufacturer's protocol using Multiscreen™ TR-FRET cAMP 1.0 No Wash Assay Kit or HTRF cAMP HiRange Kit. For agonist mode testing, cells were preincubated with customer compounds for 5 minutes at room temperature prior to the addition of forskolin, and the plate was then incubated at 37° C. for 20 minutes. The reaction was terminated by sequentially adding sequentially adding trFluor™ Eu-labeled cAMP and trFluor™ 650-labeled anti-cAMP antibody or D2-labeled cAMP and cryptate-labeled anti-cAMP antibody in lysis buffer. The plate was then incubated at room temperature for 60 minutes before reading fluorescent emissions at 620 nm and 665 or 668 nm with excitation at 314 nm on FlexStation III (Molecular Devices).

Data Analysis

Cyclic AMP (cAMP) assays: Cyclic AMP assay results are shown as "Ratio 665/620×10,000" (ratio of fluorescence at 665 nm and 620 nm×10,000) or "Ratio 668/620×10,000" (ratio of fluorescence at 668 nm and 620 nm×10,000). Data in graphs were represented in Mean±SD. Dose-dependent responses were fitted with sigmoidal dose-response curves allowing variable slopes using GraphPad Prism versions 4, 5 or 6 (Graphpad Prism).

Results and Discussion

Control agonists for all 3 GPCRs showed dose-dependent stimulation in the receptor expressing cells with expected EC50b (a drug concentration that gives half-maximal response) values. All compounds and control agonists displayed dose response activity in DP1, EP2, and IP1 receptor expressing cells. EC50 values determined from the dose-dependent responses is presented in Table 3.

TABLE 3

| Compound | IP receptor | EP receptor | DP receptor |
|---|---|---|---|
| Treprostinil | $7.79 \times 10^{-11}$ | $5.37 \times 10^{-10}$ | $7.80 \times 10^{-11}$ |
| Prodrug XV | $4.28 \times 10^{-9}$ | $4.15 \times 10^{-8}$ | $6.99 \times 10^{-9}$ |

Conclusions

The data in Table 3 demonstrate that Prodrug XV was significantly less potent than treprostinil against DP1, EP2 and IP1. Although the present invention is not limited by a theory of its operation, the site pain observed during subcutaneous administering of treprostinil may be due to treprostinil affecting one or more of the IP receptor, the DP receptor and the EP receptor in the subcutaneous tissue. Because Prodrug XV is less potent against each of the IP receptor, the DP receptor and the EP receptor than treprostinil, it may cause less site pain when administered subcutaneously.

Example 6

Evaluation of Prodrug XIV Against Human G Protein Coupled Receptors

Treprostinil Prodrug XIV (for structure see FIG. 10) as well as treprostinil were tested for 3 G-protein-coupled receptors (GPCRs), namely DP1, EP2, and IP, using cyclin adenosine monophosphate (cAMP) assay.

Materials. Cells and control agonists: Cells and control agonists used in the study are summarized in Table 1.

Compounds were provided 2 compounds in powder form. The compounds were reconstituted in DMSO at a concentration of 10 mM.

Cyclic AMP assay kits: Multiscreen™ TR-FRET cAMP 1.0 No Wash Assay Kit (Multispan, Inc., Cat #MSCM01-25) and HTRF cAMP HiRange Kit (CisBio, Cat #62AM6PEC).

Instruments: FlexStation III (Molecular Devices).

Methods

Cyclic AMP (cAMP) Assay: cAMP assays were performed according to the manufacturer's protocol using Multiscreen™ TR-FRET cAMP 1.0 No Wash Assay Kit or HTRF cAMP HiRange Kit. For agonist mode testing, cells were preincubated with customer compounds for 5 minutes at room temperature prior to the addition of forskolin, and the plate was then incubated at 37° C. for 20 minutes. The reaction was terminated by sequentially adding sequentially adding trFluor™ Eu-labeled cAMP and trFluor™ 650-labeled anti-cAMP antibody or D2-labeled cAMP and cryptate-labeled anti-cAMP antibody in lysis buffer. The plate was then incubated at room temperature for 60 minutes before reading fluorescent emissions at 620 nm and 665 or 668 nm with excitation at 314 nm on FlexStation III (Molecular Devices).

Data Analysis

Cyclic AMP (cAMP) assays: Cyclic AMP assay results are shown as "Ratio 665/620×10,000" (ratio of fluorescence at 665 nm and 620 nm×10,000) or "Ratio 668/620×10,000" (ratio of fluorescence at 668 nm and 620 nm×10,000). Data in graphs were represented in Mean±SD. Dose-dependent responses were fitted with sigmoidal dose-response curves allowing variable slopes using GraphPad Prism versions 4, 5 or 6 (Graphpad Prism).

Results and Discussion

Control agonists for all 3 GPCRs showed dose-dependent stimulation in the receptor expressing cells with expected EC50 (a drug concentration that gives half-maximal response) values. All compounds and control agonists displayed dose response activity in DP1, EP2, and IP1 receptor expressing cells. EC50 values determined from the dose-dependent responses is presented in Table 4.

TABLE 4

| Compound | IP receptor | EP receptor | DP receptor |
| --- | --- | --- | --- |
| Treprostinil | $1.69 \times 10^{-11}$ | $2.35 \times 10^{-10}$ | $2.77 \times 10^{-10}$ |
| Prodrug XIV | $3.33 \times 10^{-9}$ | $6.70 \times 10^{-8}$ | $3.88 \times 10^{-8}$ |

Conclusions

The data in Table 4 demonstrate that Prodrug XIV was significantly less potent than treprostinil against DP1, EP2 and IP1. Although the present invention is not limited by a theory of its operation, the site pain observed during subcutaneous administering of treprostinil may be due to treprostinil affecting one or more of the IP receptor, the DP receptor and the EP receptor in the subcutaneous tissue. Because Prodrug XIV is less potent against each of the IP receptor, the DP receptor and the EP receptor than treprostinil, it may cause less site pain when administered subcutaneously.

Example 7

Development of HPLC Analytical Methods and Determination of Equilibrium Solubility and Solution Stability for Eight Prodrugs of Treprostinil in a Chosen Vehicle

1. Objective and Summary

The objective of this study was to develop analytical method suitable for the analysis multiple prodrugs of treprostinil and to determine the equilibrium solubility and solution stability of eight prodrugs in a chosen vehicle (20 mM dibasic sodium phosphate with 125 mM sodium chloride).

Eight prodrugs of treprostinil including Prodrug III, IV, VIII, X, XI, XII, XIII, and XIV were used for this study. The analytical method previously developed for prodrug VII was utilized for other prodrugs after minor modification of the method parameters to improve specificity. Once adequate specificity was achieved, an equilibrium solubility study was conducted for each prodrug. The solubility study was evaluated across multiple time points to assess solution stability of the prodrugs in the selected vehicle.

2. Experimental

2.1 Equipment

All studies were conducted on Waters UPLC H-Class system equipped with a photodiode array detector (PDA). All columns evaluated were 2.1×100 mm, 1.7 μm.

2.2 Development of Method Conditions

2.2.1 Evaluation of Prodrug VII Method Conditions

A previously developed analytical method for treprostinil Prodrug VII was the starting place for developing conditions for chromatographic specificity of Prodrugs III, IV, VIII, X, XI, XII, XIII, and XIV. The Prodrug VII method conditions are provided in Table 5.

TABLE 5

Nominal Starting conditions for method optimization

| Parameter | Final Method Condition |
|---|---|
| Detection | UV @ 217 nm (4.8 nm resolution) Sampling Rate: 5 pts/s |
| Flow Rate | 0.4 mL/min |
| Column | ACE Excel2 C18, 2.1 × 100 mm 1.7 μm |
| Column Temperature | 40° C. |
| Sample Concentration | 1 mg/mL |
| Diluent | 50:50 Acetonitrile: 20 mM Sodium Phosphate Buffer pH 6.2 |
| Injection Volume | 1.0 μL |
| Column Temp: | 40° C. |
| Run Time | 20 min |

| Time, min | MPA % (0.1% phosphoric acid in $H_2O$) | MPB % (Acetonitrile) |
|---|---|---|
| 0.0 | 70 | 30 |
| 0.50 | 70 | 30 |
| 14.0 | 25 | 75 |
| 16.0 | 5 | 95 |
| 17.0 | 5 | 95 |
| 17.1 | 70 | 30 |
| 20.0 | 70 | 30 |

The goal of the specificity study was to achieve a single chromatographic condition that resolves each prodrug from treprostinil. Each prodrug was individually prepared and then separately spiked with 10% nominal treprostinil to evaluate specificity. A chromatographic overlay the prodrugs and treprostinil analyzed by the Prodrug VII analytical method is provided in FIG. 11.

The results of the specificity study using the Prodrug VII method indicate that treprostinil is well separated from all prodrugs except Prodrug XIV which co-elutes.

Three additional columns were screened to evaluate specificity of prodrugs using the Prodrug VII method conditions. A chromatographic overlay of treprostinil and the eight prodrugs on a Waters BEH C18 column is provided in FIG. 12. A chromatographic overlay of treprostinil and the eight prodrugs on a ACE C18-AR column is provided in FIG. 13. A chromatographic overlay of treprostinil and the eight prodrugs on a Waters CSH Phenyl Hexyl column is provided in FIG. 14.

The results of the column screening indicated that all prodrugs including Prodrug XIV can be adequately resolved from treprostinil on either the ACE Excel 2 C18-AR column (Rs=2.8, Result ID 2949) or the Waters CSH Phenyl Hexyl column (Rs=2.9, Result ID 3028). While the resolution was essentially equivalent between columns the CSH Phenyl Hexyl column was selected for equilibrium solubility and solution stability studies.

3 Equilibrium Solubility and Solution Stability 3.1. Study Design

Each prodrug was dissolved in a vehicle containing 20 mM sodium phosphate dibasic with 125 mM sodium chloride. Prodrugs were prepared at saturation concentrations by weighing 15-30 mg of prodrug in to a 4 mL clear glass vial and dissolving in an appropriate volume of vehicle (0.5-1.0 mL) to achieve a nominal saturation concentration of 30 mg/mL. The solutions were mixed for 23 hours on a rotating mixer. All solutions except Prodrug XIV exhibited solids after mixing. The resultant supernatant solutions were isolated from undissolved prodrug by centrifugation at 15000 RPM for 15 min. Supernatants were transferred to clear glass vials and stored at ambient temperature. To evaluate solubility and solution stability, supernatants were diluted 21.7-fold by transferring 15 μL supernatant to a micro vial and adding 210 uL of diluent (25:75 Acetonitrile: 20 mM sodium phosphate pH 6.2) and 100 μL acetonitrile. The resultant samples were assayed against treprostinil to determine prodrug concentration. At each testing interval (0, 24, 72 hours) the supernatant was assayed for prodrug concentration and purity by area %.

3.2. Study Results

The results of the equilibrium solubility study across the three stability testing intervals is summarized in Table 6. The results of the solution stability for prodrugs is summarized in Table 7 and Table 8.

TABLE 6

Equilibrium Solubility of Treprostinil Prodrugs evaluated over 72 hours in vehicle containing 20 mM sodium phosphate dibasic with 125 mM sodium chloride

| Compound | T0 hours Concentration (mg/mL) | T24 hours Concentration (mg/mL) | T72 hours Concentration (mg/mL) |
|---|---|---|---|
| Prodrug III | 6.1 | 6.0 | 6.2 |
| Prodrug IV | 12.5 | 12.2 | 12.9 |
| Prodrug VIII | 11.0 | 10.5 | 10.9 |
| Prodrug X | 10.0 | 10.6 | 11.3 |
| Prodrug XI | 11.5 | 11.3 | 11.5 |
| Prodrug XII | 7.4 | 7.5 | 7.4 |
| Prodrug XIII | 3.2 | 3.7 | 3.8 |
| Prodrug XIV | 29.5 | 27.5 | 26.6 |

TABLE 7

Solution stability of Prodrug (area % purity) in vehicle containing 20 mM sodium phosphate dibasic with 125 mM sodium chloride

| Compound | T0 Purity (% Area) | T24 hours Purity (% Area) | T72 hours Purity (% Area) |
|---|---|---|---|
| Prodrug III | 94.48 | 94.31 | 94.61 |
| Prodrug IV | 99.19 | 99.02 | 99.15 |
| Prodrug VIII | 96.41 | 96.40 | 96.34 |
| Prodrug X | 96.59 | 96.32 | 96.54 |
| Prodrug XI | 99.49 | 99.39 | 98.92 |
| Prodrug XII | 98.70 | 98.68 | 98.58 |
| Prodrug XIII | 97.66 | 97.81 | 97.58 |
| Prodrug XIV | 94.20 | 94.25 | 94.56 |

TABLE 7

Solution stability of Prodrug (area % residual treprostinil) in vehicle containing 20 mM sodium phosphate dibasic with 125 mM sodium chloride

| Compound | T0 Residual Treprostinil (% Area) | T24 Residual Treprostinil (% Area) | T72 Residual Treprostinil (% Area) |
|---|---|---|---|
| Prodrug III | 0.15 | 0.14 | 0.15 |
| Prodrug IV | ND | ND | ND |
| Prodrug VIII | 0.11 | 0.11 | 0.15 |
| Prodrug X | 0.08 | 0.08 | 0.08 |
| Prodrug XI | ND | ND | ND |
| Prodrug XII | ND | ND | ND |
| Prodrug XIII | ND | ND | ND |
| Prodrug XIV | 0.08 | 0.13 | 0.23 |

3.3. Discussion

The equilibrium solubility study for eight prodrugs of treprostinil indicates a wide range of solubility across the compounds in the selected vehicle. Prodrug XIII was the least soluble (approx. 3.5 mg/mL) and prodrug-N was the most soluble (approx. 30 mg/mL). The prodrugs were demonstrated to be stable in the vehicle up to 72 hours with little to no change in both prodrug purity and residual treprostinil. Prodrug XIV showed the largest treprostinil formation in the vehicle across all prodrugs evaluated however only 0.15% was formed for this prodrug over 72 hours.

4. Conclusion

An analytical method was developed for evaluation of eight prodrugs of treprostinil by UPLC-UV. The PRODRUG VII method conditions were used as a starting place for method optimization minor modification to change column chemistry (Waters CSH Phenyl Hexyl instead of ACE Excel 2 C18). The change was required to resolve each prodrug adequately from treprostinil. Equilibrium solubility studies indicated a wide range of solubility for prodrugs in the selected vehicle across the eight compounds. Six of the eight prodrugs had solubility in vehicle between 6-13 mg/mL while one low solubility prodrug was observed (Prodrug-M, approx. 3.5 mg/mL) and one high solubility prodrug was observed (Prodrug-N, approx. 30 mg/mL). All prodrugs showed were stable up to 72 hours in the vehicle based on minimal formation of treprostinil and minor changes in area % purity.

Example 8

Objective and Summary

The objective of this study was to determine the in vitro metabolic stability of nine prodrugs (III, IV, VII, VIII, X, XI, XII, XIII, and XIV) in human, Beagle dog and Sprague Dawley rat liver microsomes, as well as four prodrugs (III, IV, VII and XIV) in Cynomolgus monkey liver microsomes. Another goal was to study the release of parent compound (treprostinil) over the time course.

Test articles were incubated with liver microsomes in the presence and absence of NADPH. At selected time points, aliquots of the incubation reaction were removed, quenched, and analyzed using liquid chromatography tandem mass spectrometry (LC-MS/MS). Both the prodrug and treprostinil concentrations were determined, and half-lives of prodrugs were calculated.

The half-lives of prodrugs are tabulated in FIG. 15. Half-lives longer than three times testing duration (120 min) are reported as ">360".

Materials

SigmaFAST™ protease inhibitor cocktail tablets (Sigma-Aldrich P/N: S8830); HPLC water (Fisher); Acetonitrile, HPLC grade, (Fisher); Formic Acid, Optima LCMS grade, (Fisher P/N: A117); Dimethyl Sulfoxide (Fisher P/N D159-4); Human Liver Microsomes, mixed gender, pool of 50 (XenoTech P/N: H0610); Dog Liver Microsomes, Beagle, male, pool of 8 (XenoTech P/N: D1000); Rat Liver Microsomes, Sprague Dawley, male, pool of 500 (XenoTech P/N: R1000); Monkey Liver Microsomes, Cynomolgus, male, pool of 12 (XenoTech P/N: P2000; Lot #1110090); Matrix tubes, 1.4 ml (Fisher P/N 50823825); Matrix tube racks (Fisher P/N 50823921); Sepraseal Caps for matrix tubes (Fisher P/N NC9995413)

Equipment

AB SCIEX API 4000™ LC-MS/MS system; Agilent 1100 Binary HPLC Pump, Model G1312A; Leap HTS PAL Autosampler Equipped with a Cold Stack; Ascentis Express® Phenyl Hexyl 2.7 µm Column, 100 mm×3 mm (Sigma-Aldrich P/N: 53345-U); Ascentis Express® Phenyl-Hexyl 2.7 µm Guard Cartridge, 5 mm×3 mm (Sigma-Aldrich P/N: 53526-U); Ascentis Express® Guard Cartridge Holder, (Sigma-Aldrich P/N: 53500-U); Aquasil C18 Dash HTS column, 5 µm, 20×2.1 mm (Thermo P/N: 77505-022150); Beckman Allegra 25R Centrifuge (P/N 36934); Rainin Pipettes: 0.2-2 µL, 2-20 µL, 10-100 µL, 20-200 µL, and 100-1000 µL; Repeater (Eppendorf); Rainin Multi-channel Pipettes: 1-20 µL, 20-200 µL, and 100-1000 µL

Incubation

Dosing solutions of Prodrugs III, IV, VII, VIII, X, XI, XII, XIII, and XIV were made in 20 mM Dibasic Potassium Phosphate. Concentration of prodrugs were 5 mM.

Liver microsomes (Xenotech) were diluted to a final protein (enzyme) concentration of 0.5 mg/mL in a buffer with the following constituents: 100 mM potassium phosphate (pH 7.4), 5 mM Magnesium Chloride ($MgCl_2$), and 1 mM β-Nicotinamide adenine dinucleotide 2'-phosphate (NADPH). The microsomal solution was aliquoted into glass tubes and incubated at 37° C. for about three minutes. An aliquot of each compound was diluted 50-fold into the pre-warmed microsome solutions and mixed to initiate the reaction. Final concentration of prodrugs in incubation solution was 100 μM.

In the first assay, all nine prodrugs (III, IV, VII, IX, X, XI, XII, XIII and XIV) were tested in human, Beagle dog and Sprague Dawley rat liver microsomes. In the second assay, four prodrugs (III, IV, VII and XIV) were tested in Cyno monkey liver microsomes.

In addition to the test compounds, three quality control compounds (7-ethoxycoumarin, propranolol, and verapamil) were included to ensure the microsomes were active. Quality control compound stock solution were made at 25 μM in 25% methanol, while the concentration in final incubation solution was 500 nM.

Negative controls were also included; these reactions contained all of the components listed above except NADPH.

All tests were performed in duplicate. All replicates were tested in separate reaction vials.

Time points of 0, 15, 30, 60 and 120 minutes were evaluated with the +NADPH conditions described above, while time points of 0 and 120 min were evaluated with the −NADPH conditions. At specified time points, a 100 μL aliquot of each reaction was removed from the reaction and added to 200 μL of ice cold acetonitrile in a deep 96-well plate. This step both quenched the reaction and precipitated proteins in preparation for LC/MS/MS analysis. When the time course was complete, the plates were sealed, mixed, and centrifuged at 4500 g and 4° C. for 15 minutes. 200 μl of the resulting supernatant was frozen in matrix tubes at −80° C. until analysis.

Bioanalytical Preparation Procedure

Test Articles

Solution preparation. Primary stock solutions of the Prodrugs III, IV, VII, IX, X, XI, XII, XIII and XIV, and treprostinil were made in 90% DMSO. The 9 prodrug stock solutions were combined and serially diluted to 9-in-1 standard spike-in solutions and 9-in-1 QC spike-in solutions. On the other hand, treprostinil stock solution was serially diluted to treprostinil standard spike-in solutions and QC spike-in solutions. After preparation, all solutions were stored at 4° C. Dilution QCs (QC-dilu) were tested for individual compounds to ensure the compounds do not crosstalk. Individual primary stock solutions of prodrugs and treprostinil were used as spike-in solution for QC-dilu.

Blank matrix. Blank matrix was prepared by preparing liver microsomal solution (100 mM potassium phosphate buffer pH7.4, 5 mM $MgCl_2$, 0.5 mg/ml enzyme, 1 mM NADPH), followed by heat-inactivation in boiling water bath for 5 min. Unknown samples were analyzed separately for different species. The species of liver microsomes used in preparation of blank matrix was the same as the unknown samples, e.g., human liver microsomes were used to prepare the blank matrix for analysis of human samples only.

Blank extract. Blank extract was prepared by combining two volumes of acetonitrile and one volume of blank matrix. The mixture was then centrifuged at 4000 g and the supernatant was taken.

Standard, QC and undiluted unknown samples. Samples were extracted using a protein precipitation procedure. 5 μl of standard or QC (including QC-dilu) spike-in solution were spiked into 95 μl of blank matrix in a deep-well plate, followed by addition of 200 μl acetonitrile. Undiluted unknown samples (thawed at room temperature and mixed well) were added to a deep-well plate, followed by addition of 200 μl acetonitrile. The standard/QC and undiluted sample plates were then sealed, mixed and centrifuged at 5500 g and 4° C. for 15 min. 100 μl of supernatant (excluding QC-dilu) was combined with 100 μl of internal standard working solution (ISWS, 20 ng/ml $d_4$-treprostinil in water) on final microtiter plates.

Dilution QC additional steps. After protein precipitation and centrifugation, 10 μl supernatant was added to an intermediate row loaded with 90 μl blank extract (10× dilution), mixed with pipette, and then 10 μl of diluted samples were added to a row on the final microtiter plate loaded with 90 μl blank extract (another 10× dilution). 100 μl ISWS was added.

Diluted unknown samples. 10 μl unknown sample was added to an intermediate plate loaded with 90 μl blank extract (10× dilution), mixed with pipette, and then 10 μl of diluted samples were added to the final microtiter plates loaded with 90 μl blank extract (another 10× dilution). 100 μl ISWS was added.

Double blanks. 100 μl blank extract was combined with 100 μl water.

All plates were sealed, mixed, centrifuged at 5500 g and 4° C. for 5 min, and ready for LC-MS/MS.

Quality Control Compounds

Unknown samples. All quality control compound samples were thawed at room temperature and mixed well. 60 μl of sample was added to microtiter plates loaded with 120 μl water and 40 μl ISWS (50 ng/ml labetalol in methanol).

Double blanks. 60 μl blank extract (blank extracts from the test article runs were used) was combine with 120 μl water and 40 μl methanol. Separate double blanks were made for each species.

The plates are sealed, mixed, centrifuged at 5000 g and 10° C. for 10 min, and ready for LC-MS/MS.

LC-MS/MS

The LC-MS/MS system consisted of a Leap HTS PAL autosampler, an Agilent 1100 series liquid chromatography pump, and a Sciex API4000 mass spectrometer operated in triple quadrupole mode. An Ascentis Express® Phenyl Hexyl column (2.7 μm, 100 mm×3 mm) or an Aquasil C18 Dash HTS column (5 μm, 20×2.1 mm) was used at 40° C. with 0.1% formic acid as mobile phase A and neat acetonitrile as mobile phase B.

The mass spectrometer (MS) was operated in negative or positive Turbo IonSpray™ mode with Multiple Reaction Monitoring (MRM). The MS parameters are also shown in Appendix 2.

Quantitation

Test Articles

To quantify the prodrugs and treprostinil in the unknown samples, all the unknown samples ran with calibration curves of the 9-in-1 prodrugs and treprostinil in separate batches.

Automatic integration algorithm was used to integrate the chromatographic peaks. Integrations were adjusted only as needed to ensure integrations are consistent for all standards, quality controls, and samples within a run.

Peak area ratios were calculated (analyte peak area divided by internal standard peak area). Standard curves were created by generating least squares fitting plots of peak area ratio versus nominal concentration. Sample concentrations were calculated from the results of the least squares fits. When calculated sample concentration is lower than the LLOQ (Lower Limit of Quantitation), a "BQL" (Below Quantitation Limit) is reported.

Acceptance criteria: The back-calculated accuracy should be within ±20% of the nominal concentration for at least 75% of all standards. The accuracy of at least two-thirds of all the quality control samples should be within ±20% of the nominal concentration, and at least 50% at each level must meet the above criteria. Correlation coefficient of final curve must be ≥0.99.

A $1/(x^2)$ weighted, quadratic or linear regression was used. Calibration standards that do not meet acceptance criteria for back-calculated accuracy were removed.

Test injections were made to estimate the concentrations of representative samples, and this was used to decide whether diluted or undiluted samples would be included in the formal batches. The calculated concentration of either the undiluted sample or diluted sample must be within the test range; otherwise, samples with lower concentration than LLOQ (Lower Limit of Quantitation) were reported as BQL (Below Quantitation Limit), while samples with higher concentration than ULOQ (Upper Limit of Quantitation) were re-tested with a higher dilution factor.

Quality Control Compounds

The peak area ratio at time zero was set to 100% and percent remaining at the remainder of time points was calculated. Plots of percent remaining versus time were ultimately used to calculate t½ values for each compound.

Kinetic Analysis

Rate constant (k): k=−β

Where β is the slope obtained from fitting semi-log plots of concentration versus time. For quality control compounds, when concentration is not available, % remaining is used instead.

Half-life (t½):

$$t_{1/2} = \frac{-0.692}{\beta}$$

Results

Test Articles

Half-lives of the prodrugs are tabulated in Table 9.

Quality Control Compounds

Half-lives of quality control compounds are tabulated in Table 9.

TABLE 9

Half-lives of quality control compounds.

| | Half-life (min) | | | | | |
|---|---|---|---|---|---|---|
| | 7-EC | | Propranolol | | Verapamil | |
| | +NADPH | −NADPH | +NADPH | −NADPH | +NADPH | −NADPH |
| Human | 5.40 | >360 | 86 | >360 | 7.46 | >360 |
| Dog | 2.05 | >360 | 12.7 | >360 | 10.1 | >360 |
| Rat | 5.89 | >360 | 2.16 | >360 | 6.09 | >360 |
| Monkey | 2.00 | >360 | 10.9 | >360 | 1.26 | >360 |

Quality control compounds had t½ values that were comparable to historical data, indicating that the microsomes used in these tests were active.

Discussions

According to the earlier aqueous solution stability study, all prodrugs are stable in 20 mM Sodium Phosphate dibasic with 125 mM NaCl at saturation concentrations (3-30 mg/ml). Also, in the method development work, it was also observed that the most unstable prodrugs III, IV and XIV were stable in 200 mM potassium phosphate buffer (pH 7.4) at a low concentration of 1 μM. These suggest that the metabolism of prodrugs in this study are not due to chemical or aqueous solution instability.

It was observed that in some cases the half-life was similar with or without NADPH. This indicates that some NADPH-independent enzymes, such as esterase and amidase, may be mainly responsible for metabolism of the prodrugs. In other cases, when the half-life with NADPH was much shorter than the half-life without NADPH, the reaction was likely mediated by (or partly mediated by) Cytochrome P450 enzymes.

Conclusions

The stability of the prodrugs are species-dependent, with IV, III, and XIV being the least stable across all species.

Example 9

Evaluation of Treprostinil Prodrugs in the Rat Intraplantar Injection Model

1. Summary

Treprostinil, a synthetic prostacyclin analog, is the active pharmaceutical ingredient in Remodulin. Subcutaneous administration of treprostinil is associated with pain at the site of injection, and the objective of this study was to evaluate alternative prodrugs of treprostinil to assess a pain response in the rat paw pain model.

Male Sprague Dawley rats (n=112) were allocated into 14 groups of 8/group. The study was run in 2 cycles, on consecutive days, 7 groups per cycle. Each cycle was composed of a Saline group, PBS group, which served as the control, and also treprostinil at a dose of 100 µg/mL or 1 µg/mL. In addition, the test items treprostinil ring carbamate (Prodrug I), treprostinil side-chain carbamate (Prodrug II), treprostinil amide (Prodrug VII) and treprostinil methyl ether (Prodrug VIII) all formulated in PBS, were tested at 2 doses (100 µg/mL or 1 µg/mL, one dose per cycle).

Animals were administered 0.1 mL of test material by subcutaneous injection into the paw pad (Intraplantar injection) at time zero. Animals were subsequently evaluated for their response to mechanical (von Frey filaments) and thermal stimuli, 15 and 90 minutes post-injection. The von Frey test was conducted prior to the thermal test, which followed immediately within minutes for each animal. In addition, clinical observation scoring of the animal's reaction to injection was conducted. FIG. 16 schematically illustrates the study design.

1.1 Measurement of Mechanical Pain Sensitivity Using the Von Frey Test (FIGS. 17 and 18)

Mechanical pain sensitivity was tested using the von Frey test, which measures the withdrawal force threshold of the animals. The lower the force applied represents a greater sensitivity to the stimulus. The von Frey test was performed 15 and 90 minutes post-Test Item injection.

Animals treated with treprostinil at a dose of 1 µg/mL or 100 µg/mL had a reduced withdrawal force threshold (higher sensitivity) at 15 and 90 minutes post-injection. This increased sensitivity was statistically significantly greater than the PBS-treated group ($p<0.05$).

Animals treated with treprostinil side-chain carbamate (Prodrug II) or treprostinil methyl ether (Prodrug VIII), at both doses, showed no statistically significant difference when compared to the PBS-treated group at both time points post-injection.

Animals treated with treprostinil ring carbamate (Prodrug I) at a dose of 1 µg/mL showed no statistically significant difference when compared to the PBS-treated group at both time points post-injection. Animals treated with 100 µg/mL treprostinil ring carbamate (Prodrug I) showed no statistically significant difference when compared to the PBS-treated group at 15 minutes post-injection; however, a statistically significant increased sensitivity was observed when compared to the PBS-treated group at 90 minutes post-injection.

Animals treated with treprostinil amide (Prodrug VII) at a dose of 1 µg/mL showed no statistically significant difference when compared to the PBS group at both time points post-injection. Animals treated with treprostinil amide (Prodrug VII) at a dose of 100 µg/mL had a statistically significant increased sensitivity when compared to the PBS treated group at both time points post-injection.

1.2 Measurement of Thermal Pain Sensitivity (FIGS. 19 and 20)

The sensitivity of animals to a thermal pain stimulus was assessed immediately following the von Frey test. The time until withdrawal of the right-injected leg from a heat source was measured, and the lower (faster) the time of response represents a greater sensitivity to the stimulus. The test was performed 15 and 90 minutes post-Test Item injection.

Animals treated with treprostinil at a dose of 1 µg/mL or 100 µg/mL had a statistically significantly faster paw withdrawal time (increased sensitivity) when compared to the PBS treated group at 15 minutes post-administration ($p<0.05$).

Animals treated with all prodrugs at both doses showed no statistically significant difference in response to the thermal stimuli when compared to the PBS group. However, animals treated with the prodrug treprostinil amide (Prodrug VII) at a dose of 100 µg/mL or with the prodrug treprostinil methyl ether (Prodrug VIII) at both doses showed a trend toward reduction in the time of response, compared to the PBS group at both time points, although with no statistical significance.

1.3 Clinical Observation Score (FIGS. 21 and 22)

A Clinical observation score was assigned by assessing for redness, swelling and paw placement.

Treatment with treprostinil at a dose of 1 µg/mL or 100 µg/mL resulted in a statistically significant increase in the clinical score at 15 and 90 minutes post-injection when compared to the PBS treated group ($p<0.05$).

Treatment with all prodrugs at a dose of 1 µg/mL showed no clinical score, similar to the PBS group, at both time points. Animals treated with the prodrugs treprostinil side-chain carbamate (Prodrug II) or treprostinil methyl ether (Prodrug VIII), at a dose of 100 µg/mL were not statistically significantly different from the PBS group at both time-points. Animals treated with the prodrug treprostinil ring carbamate (Prodrug I) at a dose of 100 µg/mL showed a statistically significant increase in the clinical score when compared to PBS group at 90 minutes post-injection. Animals treated with the prodrug treprostinil amide (Prodrug VII) at a dose of 100 µg/mL showed a statistically significant increase in the clinical score when compared to the PBS group at both time points post-injection.

2. Conclusions

In view of the findings obtained under the conditions of this study, and confined to the in-life data, administration of the alternative prodrugs of treprostinil showed a reduced pain response when compared with similar doses of treprostinil, although some differences were noted between the individual prodrugs and the different tests.

For example, treprostinil side-chain carbamate (Prodrug II) or treprostinil methyl ether (Prodrug VIII), at both doses and at both time points, were generally associated with a statistically significant reduced sensitivity of the animals to mechanical stimulation and reduced clinical score when compared to a similar doses of treprostinil.

Whereas, the prodrugs treprostinil ring carbamate (Prodrug I) and treprostinil amide (Prodrug VII) were generally associated with a reduced sensitivity of the animals to mechanical stimulation and reduced clinical score at both time points post-injection for only the 1 µg/mL dose when compared to a similar dose of treprostinil.

In addition, all prodrugs showed a reduced sensitivity to a thermal stimulation at both doses and at both time points post-injection when compared to similar doses of treprostinil.

Example 10

Evaluation of Treprostinil Prodrugs in the Rat Intraplantar Injection Model

1. Summary

Treprostinil, a synthetic prostacyclin analog, is the active pharmaceutical ingredient in Remodulin. Subcutaneous administration of treprostinil is associated with pain at the site of injection, and the objective of this study was to evaluate alternative prodrugs of treprostinil to assess a pain response in the rat paw pain model.

Male Sprague Dawley rats (n=56) were allocated into 7 groups of 8 animals per group. Animals were treated with treprostinil at a dose of 100 µg/mL or 1 µg/mL, or with the test items Prodrug VII and Prodrug XV, at both doses. Each group was compared to the phosphate buffer (50-mM phosphate buffer with 50-mM sodium chloride at pH=7.4) treated group, which served as the control (Group 1).

Animals were administered 0.1 mL of test material by subcutaneous injection into the paw pad (Intraplantar injection) at time zero. Then, the animals were subsequently evaluated for their response to mechanical (von Frey filaments) and thermal stimuli, 15 and 90 minutes post-injection. The von Frey test was conducted prior to the thermal test, which followed immediately within minutes for each animal. In addition, clinical observation scoring of the animal's reaction to injection was conducted. The study design is schematically illustrated in FIG. 23

1.1 Measurement of Mechanical Pain Sensitivity Using the Von Frey Test (FIG. 24)

Mechanical pain sensitivity was tested using the von Frey test, which measures the withdrawal force threshold of the animals. The lower the force applied represents a greater sensitivity to the stimulus. The von Frey test was performed 15 and 90 minutes post-test item injection.

Animals treated with treprostinil at a dose of 1 µg/mL or 100 µg/mL had a reduced withdrawal force threshold (higher sensitivity) at 15 and 90 minutes post-injection. This increased sensitivity was statistically significantly greater than the phosphate buffer group ($p<0.001$ and $p<0.0001$, respectively).

Animals treated with Prodrug VII or Prodrug XV at a dose of 1 µg/mL or 100 µg/mL also showed a reduced withdrawal force threshold (higher sensitivity) at 15 and 90 minutes post-injection. This increased sensitivity was statistically significantly greater than the phosphate buffer group ($p<0.001$ or $p<0.0001$). No difference in the withdrawal force threshold was found in the test items treated groups when compared to the treprostinil treated groups.

1.2 Measurement of Thermal Pain Sensitivity (FIG. 25)

The sensitivity of animals to a thermal pain stimulus was assessed immediately following the von Frey test. The time until withdrawal of the right-injected leg from a heat source was measured, and the lower (faster) the time of response represents a greater sensitivity to the stimulus. The test was performed 15 and 90 minutes post-test item injection.

Animals treated with treprostinil at a dose of 1 µg/mL or 100 µg/mL had a statistically significantly faster paw withdrawal time (increased sensitivity) when compared to the phosphate buffer treated group, 15 minutes post-administration ($p<0.0001$). 90 minutes post-test item injection, only animals treated with the higher dose of treprostinil (100 µg/mL; group 2) showed a statistically significantly increased sensitivity to the heat stimulation, compared to the vehicle (phosphate buffer) group; $p<0.05$.

Animals treated with Prodrug VII at a dose of 100 µg/mL or Prodrug XV at a both doses (1 µg/mL or 100 µg/mL) had a statistically significantly faster paw withdrawal time (increased sensitivity) when compared to the phosphate buffer treated group, 15 minutes post-administration ($p<0.01$ or $p<0.001$ or $p<0.0001$).

Interestingly, animals treated with Prodrug VII at a dose of 1 µg/mL (Group 5) had similar response time to the baseline, 15 minutes post-administration.

1.3 Clinical Observation Score (FIG. 26)

A clinical observation score was assigned by assessing for redness, swelling and paw placement.

All treated animals, except animals in group 5 that were treated with Prodrug VII at a dose of 1 µg/mL, showed statistically significant increase in the clinical score, 15 minutes post-injection when compared to the phosphate buffer treated group ($p<0.0001$). At 90 minutes time point, only animals treated with treprostinil at both doses, and animals treated with both test items at the higher dose (100 µg/mL) showed the same effect ($p<0.0001$).

2. Conclusions

In view of the findings obtained under the conditions of this study, and confined to the in-life data, administration of the alternative prodrugs of treprostinil did not show a significant effect in reducing the pain response when compared with similar doses of treprostinil. However, it is worth mentioning that treatment with the test item Prodrug VII, at a dose of 1 µg/mL, resulted in reduced sensitivity to thermal stimulation and lower values of clinical score, at both time-points post administration.

Example 11

Evaluation of Treprostinil Prodrugs in the Rat Intraplantar Injection Model

The study design is schematically illustrated in FIG. 16. FIGS. 27 and 28 present results for Von Frey Response test of Cycles 1 and 2 respectively. FIGS. 29 and 30 present results for Thermal Response test of Cycles 1 and 2 respectively. FIGS. 31 and 32 present mean clinical score for Cycles 1 and 2 respectively.

Example 12

Prodrug VII and Treprostinil: Cardiovascular Assessment Following Subcutaneous Injection to Sprague Dawley Rats

1. Objective

The objective of this study was to assess the potential acute effects of Prodrug VII or treprostinil (a prostacyclin analog) on heart rate, blood pressure (systolic, diastolic, and mean), and body temperature following subcutaneous injection in conscious Crl:CD(SD) rats instrumented with a radiotelemetry transmitter.

2. Methodology

Treprostinil in the vehicle (phosphate buffered saline [PBS] 1×) or Prodrug VII in the vehicle (20 mM phosphate buffer with 125 mM sodium chloride) was administered as a single dose via subcutaneous injection to 9 groups (Groups 1 through 9) of 4 male Sprague Dawley rats/group according to a dose escalation design (up/down procedure). The study design is shown in Table 10.

TABLE 10

| Group Number | Test Article | Dose Level (mg/kg)[a] | Dose Concentration (mg/mL) | Dose Volume (mL/kg)[a] | Number of Males |
|---|---|---|---|---|---|
| 1 | Treprostinil | 0.000125 | 0.000125 | 1 | 4[b] |
| 2 | Treprostinil | 0.00125 | 0.00125 | 1 | 4[b] |
| 3 | Treprostinil | 0.030 | 0.030 | 1 | 4[b] |
| 4 | Treprostinil | 0.3 | 0.3 | 1 | 4[b,d] |
| 5 | Prodrug VII | 1 | 0.1 | 10 | 4[c] |
| 6 | Prodrug VII | 10 | 1 | 10 | 4[c] |
| 7 | Prodrug VII | 30 | 3 | 10 | 4[c] |
| 8 | Prodrug VII | 3 | 0.3 | 10 | 4[c] |
| 9 | Treprostinil | 0.1 | 0.1 | 1 | 4[b,e] |

[a] Dose calculated from body weight.
[b] The same 4 animals received each treatment with approximately 3 days between doses.
[c] The same 4 animals received each treatment with approximately 3 days between doses.
[d] Due to the probe failure of Male No. 1172 during the Group 4 dosing session, an additional animal from the stock colony was selected and evaluated at this dose level.
[e] The 3 animals successfully evaluated in Group 4 and an additional animal from the stock colony were evaluated at this dose level.

Heart rate, arterial blood pressure (systolic, diastolic, and mean arterial pressure), pulse pressure, and body temperature were collected continuously for at least 2 hours prior to administration of treprostinil or Prodrug VII, and continuously for at least 24 hours postdosing. Clinical observations were performed at approximately 6 hours prior to dosing, at the completion of dosing and at approximately 4 hours postdosing.

3.1. Clinical Observations

Following administration of 0.1 and 0.3 mg/kg treprostinil, clinical observations of flushed extremities were noted in some animals at approximately 4 hours postdosing. Clinical observations of flushed body and/or extremities, piloerection, hypoactivity, reddened forelimb(s) and/or hindlimb(s), wet yellow material on the urogenital area and ventral trunk, and dried red material around nose were noted in some animals approximately 4 hours following administration of 3, 10, or 30 mg/kg Prodrug VII.

3.2. Hemodynamic Data

3.2.1. Heart Rate (FIG. 33)

Higher heart rates were observed following administration of treprostinil and Prodrug VII.

While the magnitude of change was generally similar for treprostinil groups (≥0.030 mg/kg), the duration of change increased with increasing dose. Heart rate changes were considered resolved by approximately 5 hours postdosing.

Similar magnitude of higher heart rate was observed following administration of 1 and 3 mg/kg; and 10 and 30 mg/kg Prodrug VII, respectively, with slightly higher heart rates noted at 10 and 30 mg/kg. Changes in heart rate persisted longer in comparison to treprostinil groups, with recovery (compared to predose baseline) for all groups observed at approximately 19 to 20 hours postdosing.

Increased heart rate following administration of treprostinil or Prodrug VII was considered to be a compensatory increase in response to reduced systemic blood pressure.

3.2.2. Systolic Blood Pressure (FIG. 34)

No meaningful changes in systolic blood pressure were observed following administration of ≤0.030 mg/kg treprostinil, although marginally lower systolic blood pressure was observed following administration of 0.03 mg/kg treprostinil. Significantly lower systolic blood pressure was observed as early as the 10 minute time point following administration of 0.1 and 0.3 mg/kg treprostinil, with the nadir at 30 and 20 minutes, and persisted through 90 and 120 minutes postdosing, respectively.

No meaningful change in systolic blood pressure was observed following administration of 0.1 mg/kg Prodrug VII. Marginally lower systolic blood pressure was observed following administration of 3 mg/kg Prodrug VII, with the nadir at 50 minutes. Significantly lower systolic blood pressure was noted following administration of 10 and 30 mg/kg as early as the 20 minute time point, with the nadir at 40 minutes and hypotension persisting through approximately 4 and 6 hours, respectively.

3.2.3. Diastolic Blood Pressure (FIG. 35)

Changes in diastolic blood pressure largely mirrored the observed changes in systolic blood pressure.

No meaningful changes in diastolic blood pressure were observed following administration of ≤0.030 mg/kg treprostinil, although marginally lower diastolic blood pressure was observed following administration of 0.03 mg/kg treprostinil. Significantly lower diastolic blood pressure was observed as early as the 10 minute time point following administration of 0.1 and 0.3 mg/kg treprostinil, with the nadir at 30 and 20 minutes, and persisted through 90 and 180 minutes postdosing, respectively.

No meaningful change in diastolic blood pressure was observed following administration of 0.1 mg/kg Prodrug VII. Marginally lower diastolic blood pressure was observed following administration of 3 mg/kg Prodrug VII, with the nadir at 50 minutes and persisted through 80 minutes. Significantly lower diastolic blood pressure was noted as early as the 20 minute time point following administration of 10 and 30 mg/kg, with the nadir at 40 minutes and hypotension persisting through approximately 4 and 7 to 8 hours, respectively.

3.2.4. Mean Arterial Pressure (FIG. 36)

Observed trends in mean arterial pressure mirrored magnitude and duration of observed changes in systolic and diastolic blood pressure. FIG. 36 illustrates the approximately 100-fold decrease in potency for Prodrug VII and the 10-20 minute delay in time to initial and maximal vasodilator effect, which may suggest that Prodrug VII conversion to treprostinil governs its vasodilatory properties. In addition, the sustained vasopressor response of Prodrug VII over approximately 2-6 hours (compared to 1-2 hours for treprostinil) suggests maintained conversion to pharmacodynamic concentrations of treprostinil.

No meaningful changes in mean blood pressure were observed following administration of ≤0.030 mg/kg treprostinil, although marginally lower mean blood pressure was observed following administration of 0.03 mg/kg treprostinil, with the nadir at 30 minutes. Significantly lower mean blood pressure was observed as early as the 10 minute time point following administration of 0.1 and 0.3 mg/kg treprostinil, with the nadir at 30 and 20 minutes, and persisted through 90 and 180 minutes postdosing, respectively.

No meaningful change in mean blood pressure was observed following administration of 0.1 mg/kg Prodrug VII. Marginally lower mean blood pressure was observed following administration of 3 mg/kg Prodrug VII, with the nadir at 50 minutes. Significantly lower mean blood pressure was noted following administration of 10 and 30 mg/kg, with the nadir at 40 minutes and hypotension persisting through approximately 4 and 7 to 8 hours, respectively.

3.2.5. Pulse Pressure (FIG. 37)

Changes in pulse pressure were variable and lacked consistent direction and magnitude of response, and further lacked dose response relationship.

Marginally lower pulse pressure was observed from 20 to 40 minutes postdosing following administration of 0.3 mg/kg treprostinil. There were no other consistent trends observed following administration of treprostinil at any other dose levels investigated.

Marginally higher pulse pressure was noted following administration of 10 mg/kg Prodrug VII. No other consistent trends were observed following any other doses of Prodrug VII.

The pulse pressure is a function of the systolic and diastolic blood pressure. As the magnitude and direction of change for systolic and diastolic were similar, the overall net change (difference between systolic and diastolic) was largely unaltered.

3.2.6. Body Temperature (FIG. 38)

No significant changes in body temperature were observed following administration of 0.000125 mg/kg or 0.00125 mg/kg treprostinil. Marginally lower body temperature was observed following 0.1 mg/kg treprostinil. This change persisted through approximately 3 hours postdosing. Significantly lowered body temperature was observed following administration of 0.1 and 0.3 mg/kg treprostinil. These changes were considered resolved by approximately 3 and 4 hours postdosing, respectively.

No significant changes in body temperature were observed following administration of 1 mg/kg Prodrug VII. Significantly lower body temperature was observed following administration of 3, 10, and 30 mg/kg. Hypothermic response persisted through 4 hours and 11 to 12 hours following administration of 3 and 10 mg/kg, respectively. Body temperature did not recover within 24 hours following administration of 30 mg/kg Prodrug VII.

Changes in body temperature were secondary to changes in blood pressure. Body temperature decreases were directly related to vasodilation.

4. Conclusions

Administration of treprostinil resulted in higher heart rate (all doses), and significantly lower systolic, diastolic, mean arterial blood pressure ($\geq 0.1$ mg/kg), and body temperature ($\geq 0.030$ mg/kg). Administration of Prodrug VII resulted in higher heart rate (all doses), and significantly lower systolic, diastolic, mean arterial), and body temperature ($\geq 3$ mg/kg).

Example 13

Synthesis of Dimethyl Ether of Treprostinil (Prodrug IX)

Discussion

The synthesis of dimethyl ether of treprostinil (1) was achieved by O-methylation using NaH and methyl iodide in THF at room temperature. This method involved short reaction time and simple work-up as compared to other reaction conditions studied to obtain the Prodrug IX.

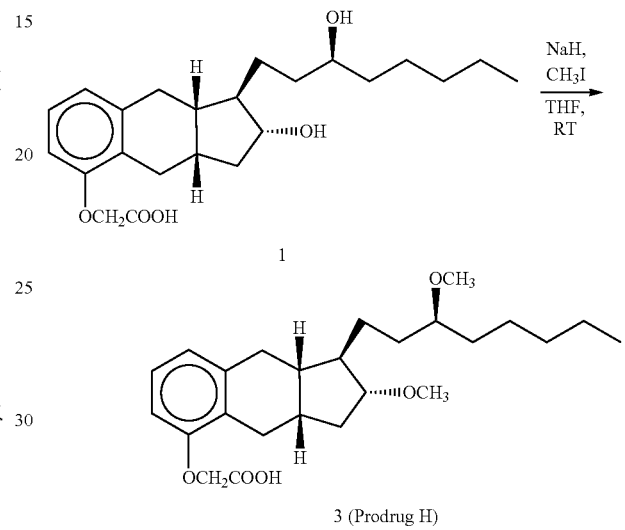

Experimental Procedure

A 50-ml round bottom flask was charged with sodium hydride (0.61 g, 15.36 mmol, 60% in mineral oil) and this was washed with hexane (2×20 ml) to remove the mineral oil. To this solid NaH, anhydrous THF (10 ml) was added and stirred at ambient temperature under argon. To this suspension, treprostinil (1) (0.5 g, 1.26 mmol) in THF (5.0 ml) was added dropwise, followed by methyl iodide (3.0 ml). The reaction mixture was stirred for 5 h and the progress of the reaction was monitored by TLC (DCM/methanol, 9:1). The reaction was quenched with aq. saturated $NH_4Cl$ solution (1.0 ml), diluted with water (10.0 ml). The pH was adjusted to 1-2 with 2N HCl. The organic layer was separated and aqueous layer was extracted with EtOAc (3×20 ml). The extracts were combined and dried over $Na_2SO_4$. The solvent was removed in vacuo to obtain crude product. The crude product was purified by silica gel chromatography using a gradient solvent (0-10% methanol in DCM) to give product dimethyl ether of treprostinil (Prodrug IX) (230 mg).

Example 14

Synthesis of Treprostinil Monomethyl Carbamate (Prodrug VIII)

The treprostinil monomethyl carbamate (Prodrug VIII) (5) was synthesized from mono-TES treprostinil benzyl ester (1). The mono-TES treprostinil benzyl ester (1) was treated with p-nitrophenyl chloroformate to generate the carbonate of p-nitrophenyl (2). The carbonate (2), without isolation, was treated with methylamine in tetrahydrofuran to give TES treprostinil benzyl monomethyl carbamate (3) in good yield. The desilylation of compound (3) with hydrochloric acid in aqueous tetrahydrofuran afforded treprostinil benzyl ester monomethyl carbamate (4). The debenzylation of pure carbamate (4) with palladium on carbon under the atmosphere of hydrogen gave treprostinil monomethyl carbamate (Prodrug VIII) (5).

Synthesis of Treprostinil Monomethyl Carbamate (Prodrug VIII) (5)

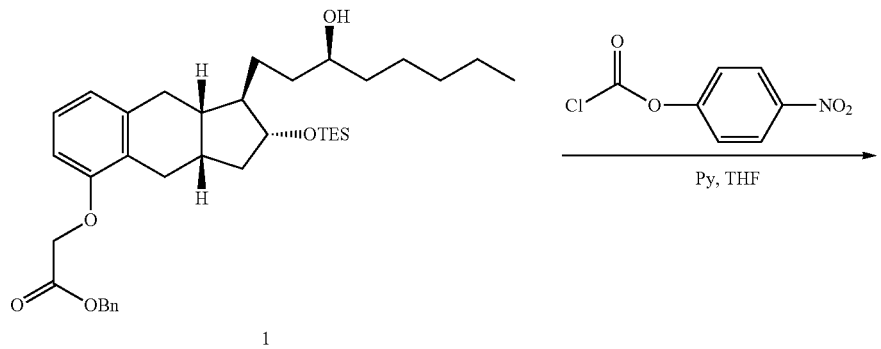

1

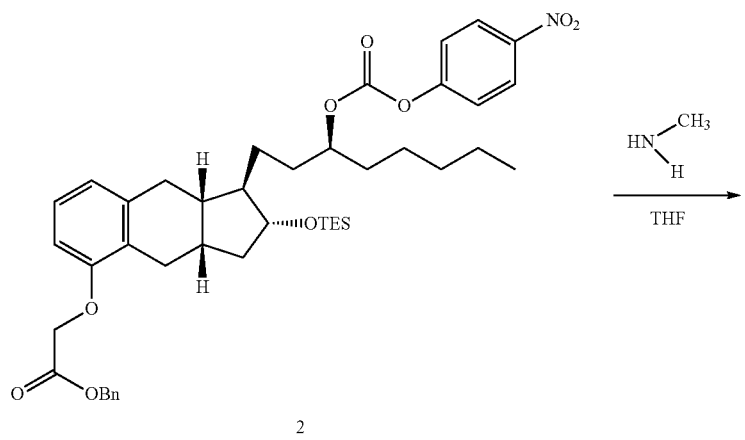

2

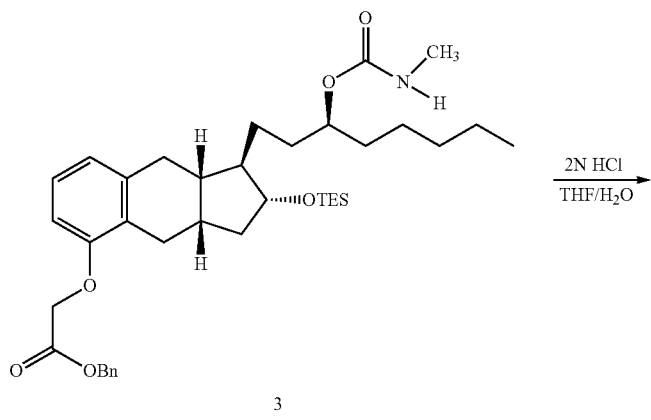

3

-continued
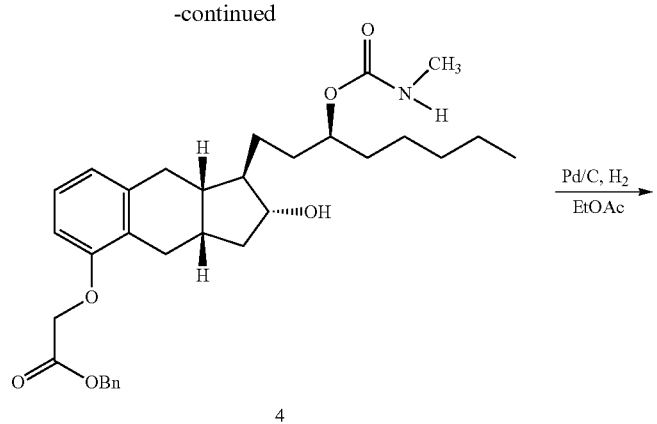
4
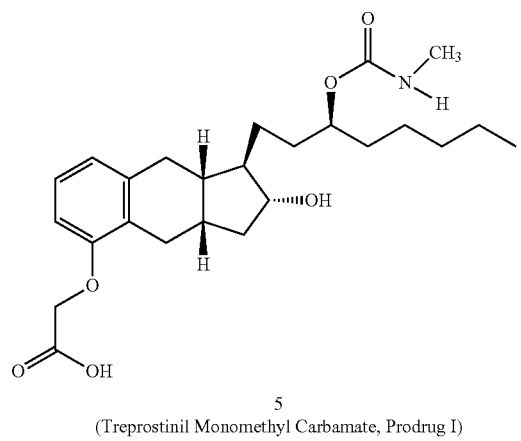 [SMILES: CCCCC[C@@H](CC[C@@H]1[C@H]2Cc3cccc(OCC(=O)O)c3C[C@H]2C[C@H]1O)OC(=O)NC]
5
(Treprostinil Monomethyl Carbamate, Prodrug I)
Experimental
Synthesis of TES-Treprostinil Benzyl Ester Monomethyl Carbamate (3)
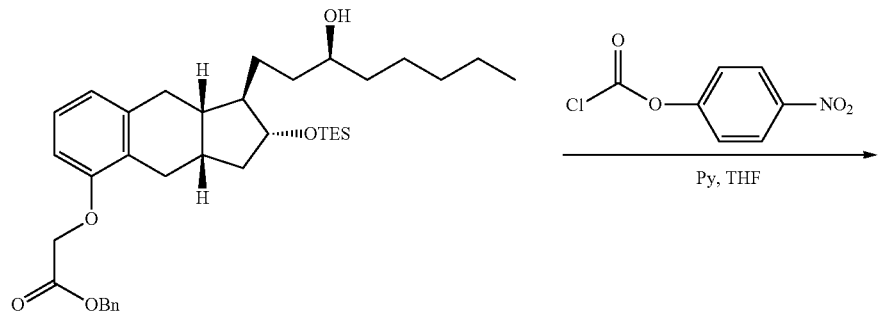
1

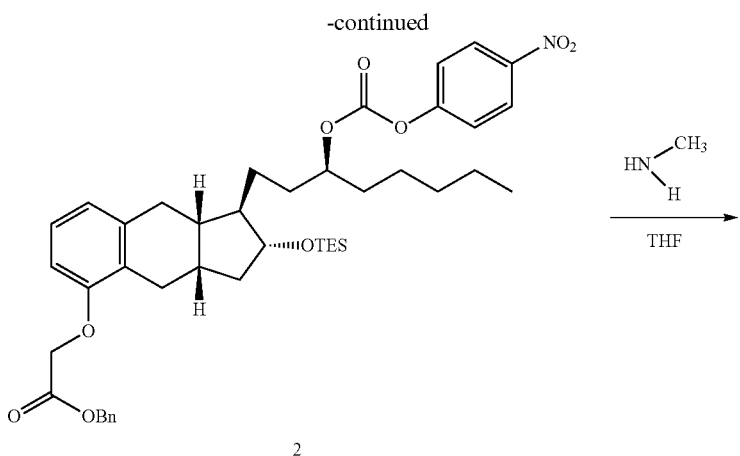

2

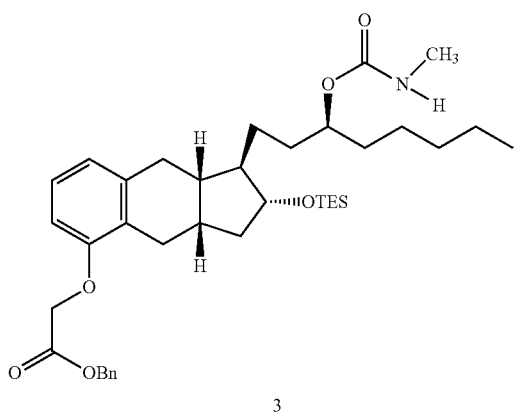

3

To a solution of mono-TES-treprostinil benzyl ester (1) (1.11 g, 1.87 mmol) in anhydrous tetrahydrofuran (12 mL) was added pyridine (0.44 g, 0.45 mL, 5.56 mmol) at room temperature under argon. The clear solution was cooled to 0° C. (ice/water bath) and then added dropwise a solution of 4-nitrophenyl chloroformate (0.56 g, 2.78 mmol) in anhydrous tetrahydrofuran (4 mL) over a period of 5 min keeping the temperature below 5° C. under argon. After complete addition, the reaction mixture (white turbid) was stirred at 0° C. to room temperature for 2 h. After 2 h, the reaction mixture was checked by tlc (EtOAc/Hexane, 1:4) and the reaction was complete. The reaction mixture was cooled to 0° C. and then added a solution of methylamine in tetrahydrofuran (2.0 M) (3.8 mL, 7.60 mmol) over a period of 3 min. The reaction mixture was stirred at 0° C. for 1 h and checked tlc (EtOAc/Hexane, 1:4). The reaction was complete. The mixture was filtered and the yellow solid was washed with MTBE (2×20 mL). The filtrate was concentrated in vacuo to give light yellow viscous liquid (1.70 g). The chromatography of the crude product on silica gel (31 g) column using 5-15% EtOAc/Hexane afforded pure TES-treprostinil benzyl ester monomethyl carbamate (3) (1.17 g).

Synthesis of Treprostinil Benzyl Ester Monomethyl Carbamate (4)

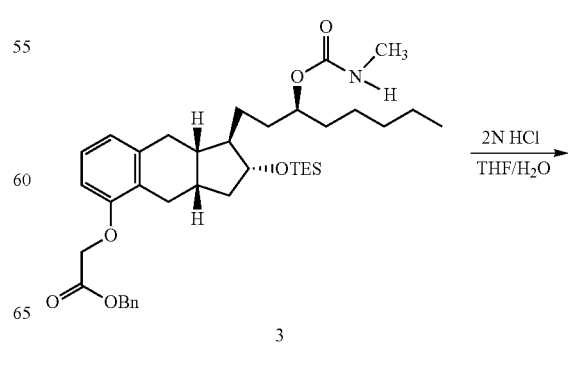

3

-continued

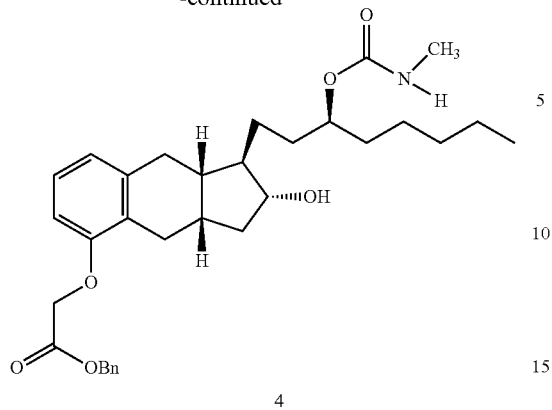

4

Synthesis of Treprostinil Monomethyl Carbamate (5)

To a solution of TES-treprostinil benzyl ester monomethyl carbamate (3) (1.10 g, 1.69 mmol) in a mixture of tetrahydrofuran (20 mL) and water (4 mL) was added hydrochloric acid solution (2 N) (0.85 mL, 1.70 mmol) at room temperature under argon. The reaction mixture was stirred at room temperature for 2 h and checked tlc (EtOAc/Hexane, 1:1). The reaction was complete. The reaction mixture was neutralized with triethylamine (0.25 mL) and then evaporated off all organic volatiles and the residue was dissolved in EtOAc (25 mL) and washed with water (2×20 mL), brine (1×10 mL), dried (Na$_2$SO$_4$), filtered and concentrated in vacuo to give clear viscous liquid (1.07 g). The crude product was chromatographed on silica gel (30 g) column using 5-70% EtOAc/Hexane) to give pure treprostinil benzyl ester monomethyl carbamate (4) as a colorless viscous liquid (0.90 g).

-continued

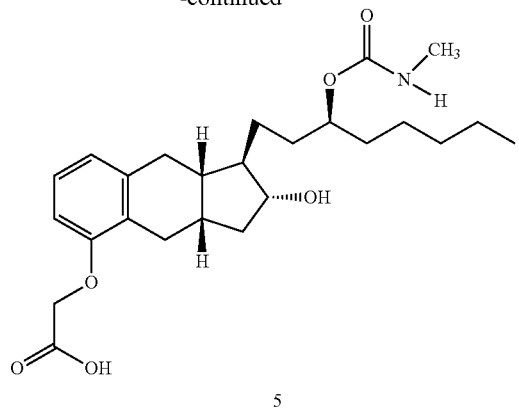

5
(Treprostinil Monomethyl Carbamate, Prodrug I)

To a solution of treprostinil benzyl ester monomethyl carbamate (4) (0.84 g, 1.56 mmol) in ethyl acetate (13 mL) was added palladium on carbon (5 wt %, 50% water) (0.15 g). The mixture was stirred and evacuated under house vacuum and replaced by hydrogen (filled in a balloon). The process was repeated three times. The mixture was stirred at room temperature under the atmosphere of hydrogen for 16 h and checked tlc (EtOAc/Hexane, 1:1). The reaction was complete. The reaction mixture was filtered through a pad of Celite (1.0 g) in a disposable polyethylene filter funnel, and the solid was washed with ethyl acetate (3×10 mL). The filtrate was concentrated in vacuo at 30° C. (water bath temperature) to give treprostinil monomethyl carbamate (Prodrug VIII) (5) as an off-white foamy solid (0.71 g)

Example 15

Synthesis of Treprostinil Amino Acid Amide Prodrugs

Discussion

Treprostinil was subjected to amidation with various amino acids using coupling agents to form the treprostinil amides as prodrugs, as shown in schemes below.

Synthesis of Treprostinil Alanine Amide (Prodrug X)

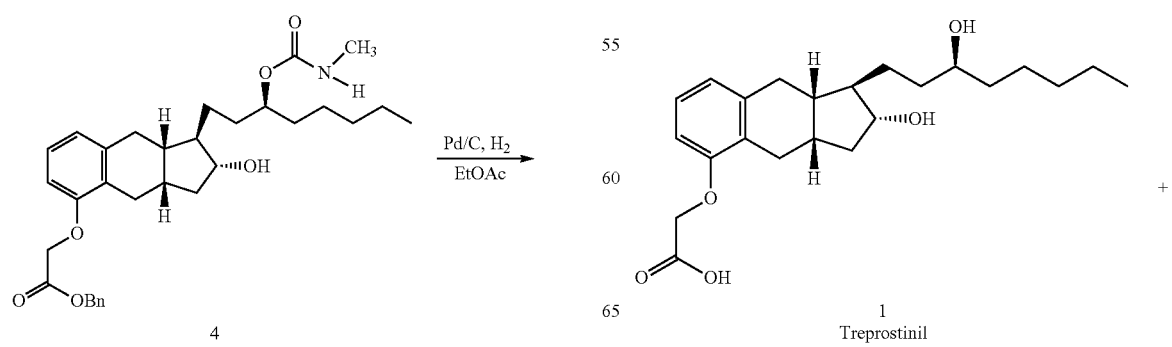

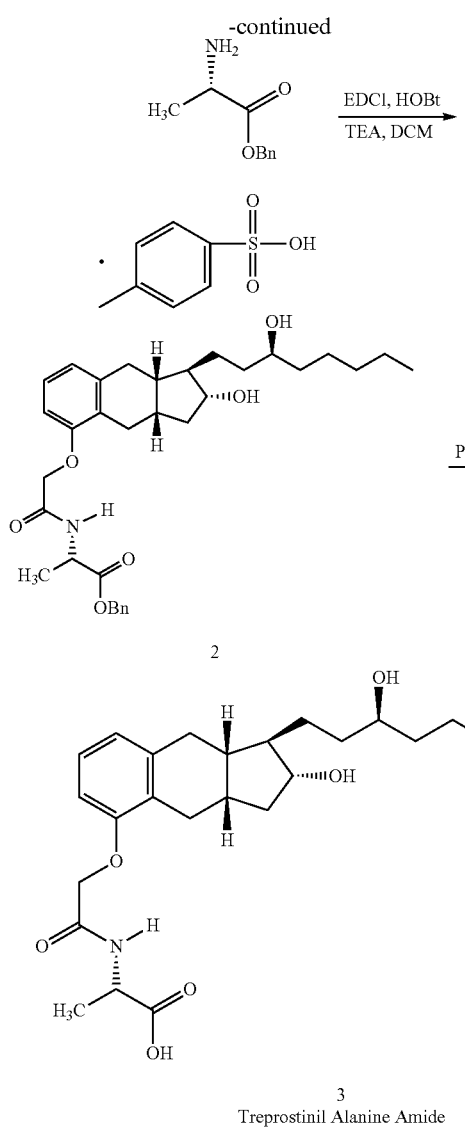

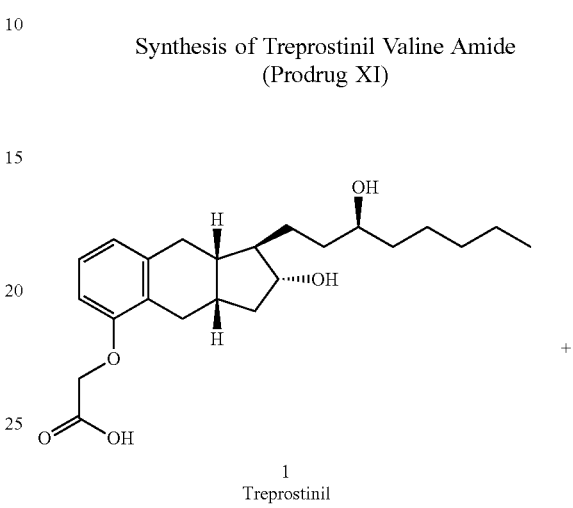

Step 1

To a suspension of treprostinil (1) (1.0 g, 2.561 mmol) and L-alanine benzyl ester p-toluenesulfonate salt (0.9 g, 2.561 mmol) in dichloromethane (30 mL) was added triethylamine (0.89 mL, 6.401 mmol). To this mixture 1-ethyl-3-(3'-dimethylaminopropyl)carbodiimide hydrochloride (EDCI) (0.59 g, 3.073 mmol) and 1-hydroxybenzotriazole hydrate (0.42 g, 3.073 mmol) were added. The reaction mixture was stirred at ambient temperature under argon for 2.5 h. Based on TLC (eluent: ethyl acetate) the reaction was found to be complete. The reaction mixture was quenched with water (30 mL) and the organic layer was separated, dried over sodium sulfate and evaporated in vacuo to obtain crude product. The crude product was purified using silica gel column chromatography using 0-70% ethyl acetate in hexane to obtain pure treprostinil alanine amide benzyl ester (2) (1.34 g, 97.8% yield).

Step 2

To a solution of treprostinil alanine amide benzyl ester (2) (1.3 g) in ethyl acetate was added a 5% palladium on carbon (50% w/w water) (130 mg). This was evacuated three times using vacuum, replaced with hydrogen gas and stirred under hydrogen atmosphere for 1.5 h. Based on TLC (eluent: ethyl acetate) the reaction was found to be complete. The reaction mixture was filtered through Celite to remove palladium on carbon. The filtrate was evaporated in vacuo to obtain treprostinil alanine amide prodrug (Prodrug X) (1.03 g, 91.7% yield).

Synthesis of Treprostinil Valine Amide (Prodrug XI)

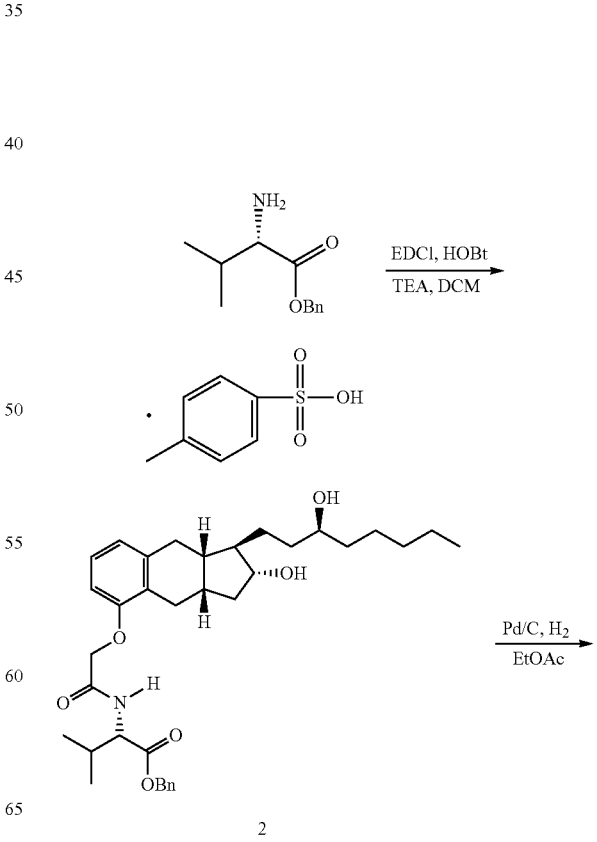

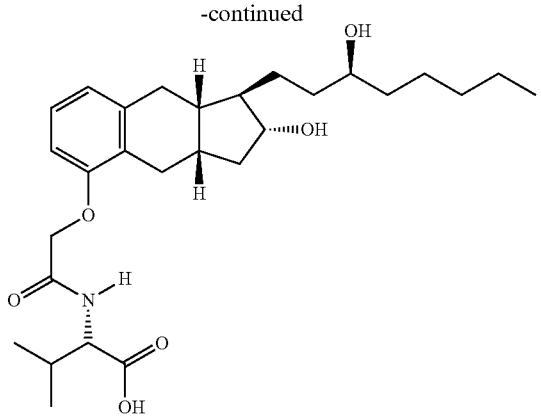

3
Treprostinil Valine Amide
(Prodrug K)

Step 1

To a suspension of treprostinil (1) (1.0 g, 2.561 mmol) and L-valine benzyl ester p-toluenesulfonate salt (0.97 g, 2.561 mmol) in dichloromethane (30 mL) was added triethylamine (0.89 mL, 6.401 mmol). To this mixture 1-ethyl-3-(3'-dimethylaminopropyl)carbodiimide hydrochloride (EDCI) (0.59 g, 3.073 mmol) and 1-hydroxybenzotriazole hydrate (0.42 g, 3.073 mmol) were added. The reaction mixture was stirred at ambient temperature under argon for 2 h. Based on TLC (eluent: ethyl acetate) the reaction was found to be complete. The reaction mixture was quenched with water (30 mL) and stirred for 15 min. The organic layer was separated, dried over sodium sulfate and evaporated in vacuo to obtain crude product. The crude product was purified using silica gel column chromatography using 0-50% ethyl acetate in hexane to obtain pure treprostinil valine amide benzyl ester (2) (1.3 g, 90.3% yield).

Step 2

To a solution of treprostinil valine amide benzyl ester (2) (1.3 g) in ethyl acetate (15 mL) was added a 5% palladium on carbon (50% w/w water) (130 mg). This was evacuated three times using vacuum, replaced with hydrogen gas and stirred under hydrogen atmosphere for 2 h. Based on TLC (eluent: ethyl acetate) the reaction was found to be complete. The reaction mixture was filtered through Celite to remove palladium on carbon. The filtrate was evaporated in vacuo to obtain treprostinil valine amide prodrug (Prodrug XI) (1.1 g, 97.1% yield with residual solvent).

Synthesis of Treprostinil Aspartic Acid Amide (Prodrug XII)

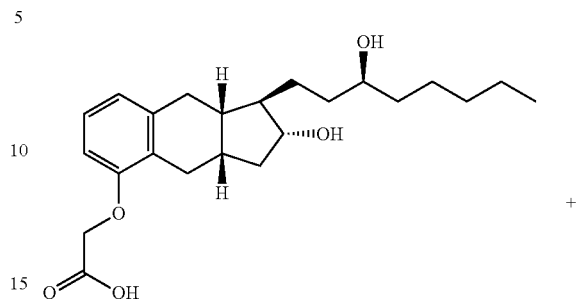

1
Treprostinil

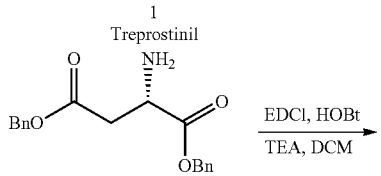

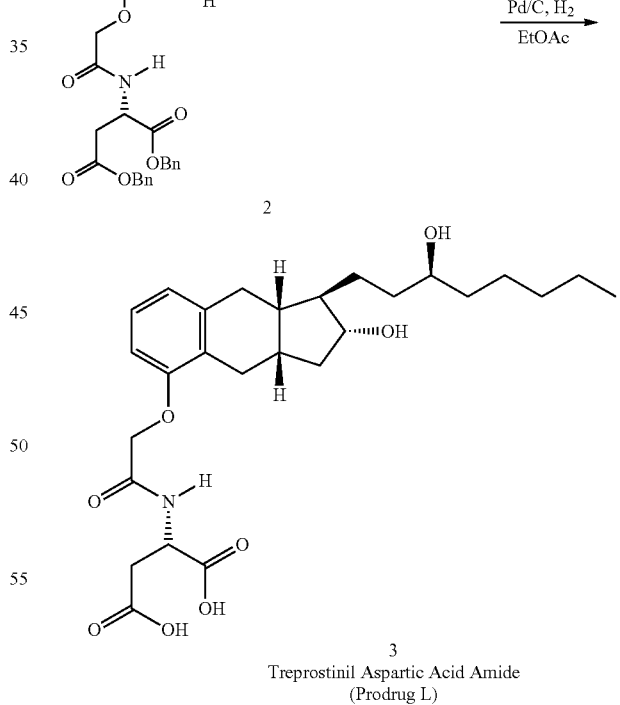

3
Treprostinil Aspartic Acid Amide
(Prodrug L)

Step 1

To a suspension of treprostinil (1) (1.0 g, 2.561 mmol) and L-aspartic acid dibenzyl ester p-toluenesulfonate salt (1.24 g, 2.561 mmol) in dichloromethane (30 mL) was added triethylamine (0.89 mL, 6.401 mmol). To this mixture 1-ethyl-3-(3'-dimethylaminopropyl)carbodiimide hydrochloride (EDCI) (0.59 g, 3.073 mmol) and 1-hydroxybenzotriazole hydrate (0.42 g, 3.073 mmol) were added. The reaction mixture was stirred at ambient temperature under argon for 2 h. Based on TLC (eluent: ethyl acetate) the reaction was found to be complete. The reaction mixture was quenched with water (30 mL) and stirred for 15 min. The organic layer was separated, dried over sodium sulfate and evaporated in vacuo to obtain crude product. The crude product was purified using silica gel column chromatography using 0-50% ethyl acetate and hexane as a mobile to obtain pure treprostinil aspartic acid amide benzyl ester (2) (1.63 g, 97.6% yield).

Step 2

To a solution of treprostinil aspartic acid amide benzyl ester (2) (0.57 g) in ethyl acetate (20 mL) was added a 5% palladium on carbon (50% w/w water) (57 mg). This was evacuated three times using vacuum, replaced with hydrogen gas and stirred under hydrogen atmosphere for 5 h. Based on TLC (eluent: ethyl acetate) the reaction was found to be complete. The reaction mixture was filtered through Celite to remove palladium on carbon. The filtrate was evaporated in vacuo to obtain treprostinil aspartic acid amide prodrug (Prodrug XII) (0.4 g, 90.9% yield).

Synthesis of Treprostinil Serine Amide (Prodrug XIII)

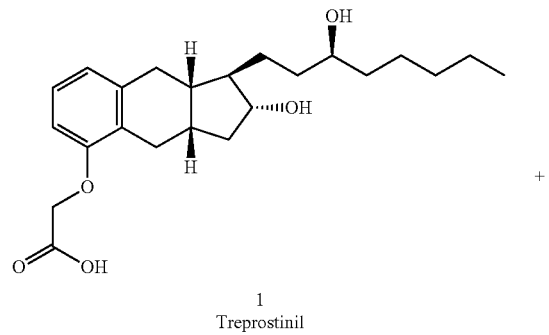
1
Treprostinil

+

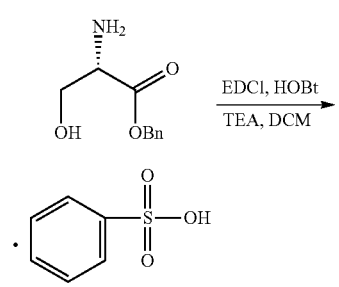

EDCl, HOBt
TEA, DCM
→

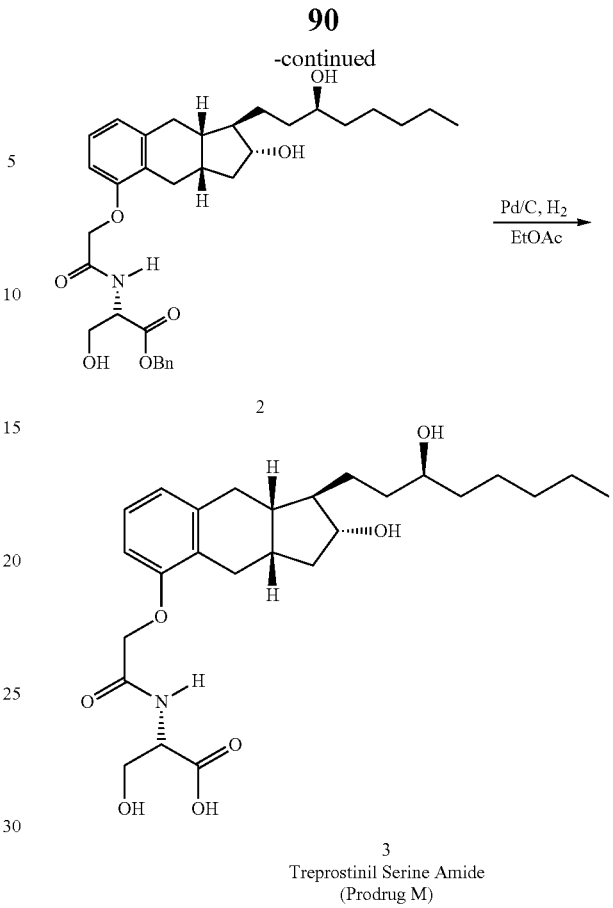

2

3
Treprostinil Serine Amide
(Prodrug M)

Step 1

To a suspension of treprostinil (1) (1.0 g, 2.561 mmol) and L-serine benzyl ester benzenesulfonate salt (0.9 g, 2.561 mmol) in dichloromethane (30 mL) was added triethylamine (0.89 mL, 6.401 mmol). To this mixture 1-ethyl-3-(3'-dimethylaminopropyl)carbodiimide hydrochloride (EDCI) (0.59 g, 3.073 mmol) and 1-hydroxybenzotriazole hydrate (0.42 g, 3.073 mmol) were added. The reaction mixture was stirred at ambient temperature under argon for 2 h. Based on TLC (eluent: ethyl acetate) the reaction was found to be complete. The reaction mixture was quenched with water (30 mL) and stirred for 15 min. The organic layer was separated, dried over sodium sulfate and evaporated in vacuo to obtain crude product. This was purified using silica gel column chromatography using 0-100% ethyl acetate and hexane as a mobile to obtain pure treprostinil serine amide benzyl ester (2) (0.62 g, 49.3% yield).

Step 2

To a solution of treprostinil serine amide benzyl ester (2) (0.57 g) in ethyl acetate (120 mL) was added a 5% palladium on carbon (50% w/w water) (57 mg). This was evacuated three times using vacuum, replaced with hydrogen gas and stirred under hydrogen atmosphere for 2 h. Based on TLC (eluent: ethyl acetate) the reaction was found to be complete. The compound crashed out of the solution after the reaction. To solubilize and isolate the product from palladium on carbon, isopropyl alcohol (30 mL) was added. The reaction mixture was then filtered through Celite to remove palladium on carbon. The filtrate was evaporated in vacuo to obtain treprostinil serine amide prodrug (Prodrug XIII) (0.54 g, 100% yield).

Example 16

Synthesis of Treprostinil Methanesulfonamide (Prodrug XIV)

The treprostinil methanesulfonamide (Prodrug XIV) (7) was synthesized from benzindene triol (1). The treprostinil benzyl ester (2) was prepared from triol (1). The ester (2) was silylated with tert-butyldimethyl trifluoromethanesulfonamide (TBDMSOTf) to give di-TBDMS treprostinil benzyl ester (3). The debenzylation of compound (3) in ethyl acetate with 5% palladium on carbon in the atmosphere of hydrogen provided di-TBDMS treprostinil (4). The activation of acid (4) with CDI followed by reaction with methanesulfonamide in the presence of DBU gave di-TBDMS treprostinil methanesulfonamide (6) and purified by silica gel column. The deprotection of TBDMS from sulfonamide (6) using hydrogen chloride in methanol afforded the desired treprostinil methanesulfonamide (Prodrug XIV) (7).

Synthesis of Treprostinil Methanesulfonamide (Prodrug XIV)

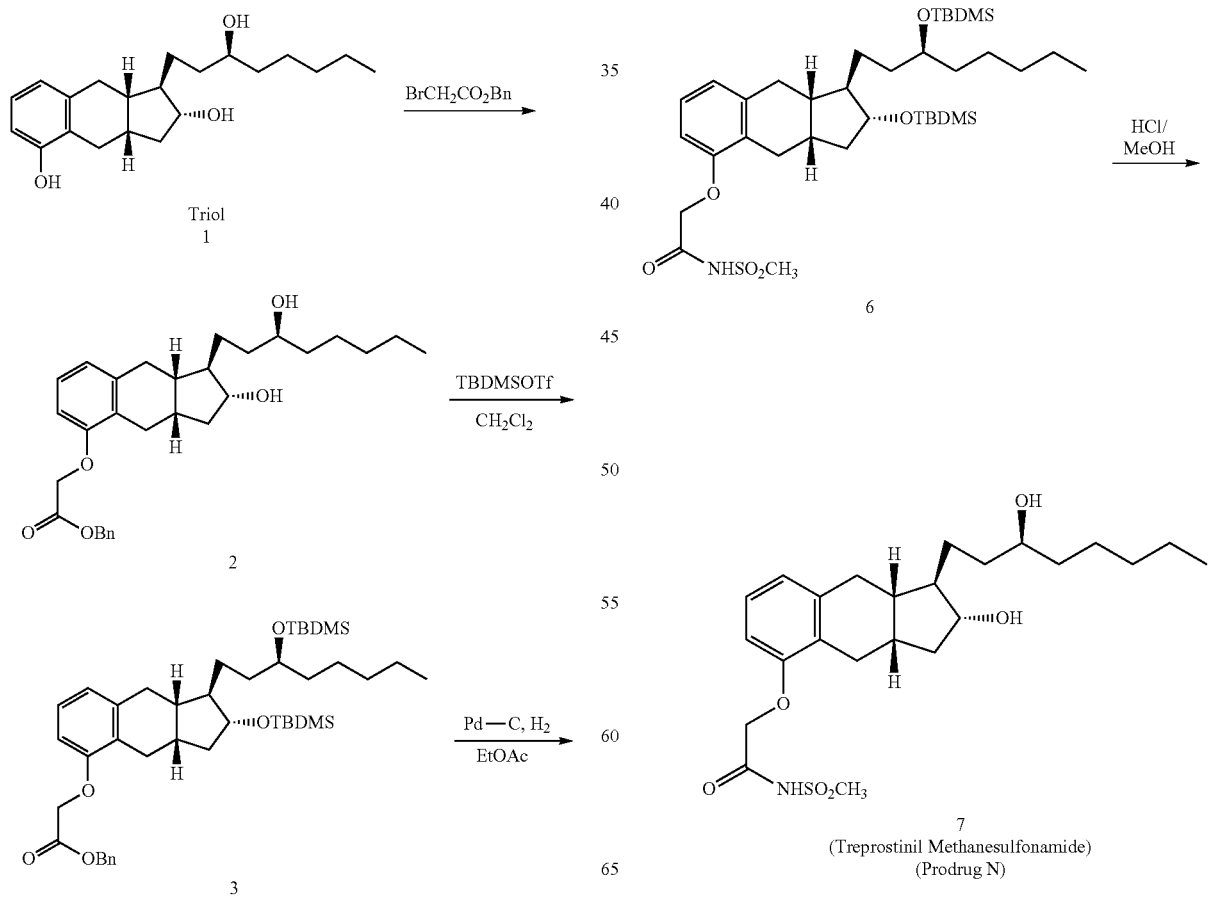

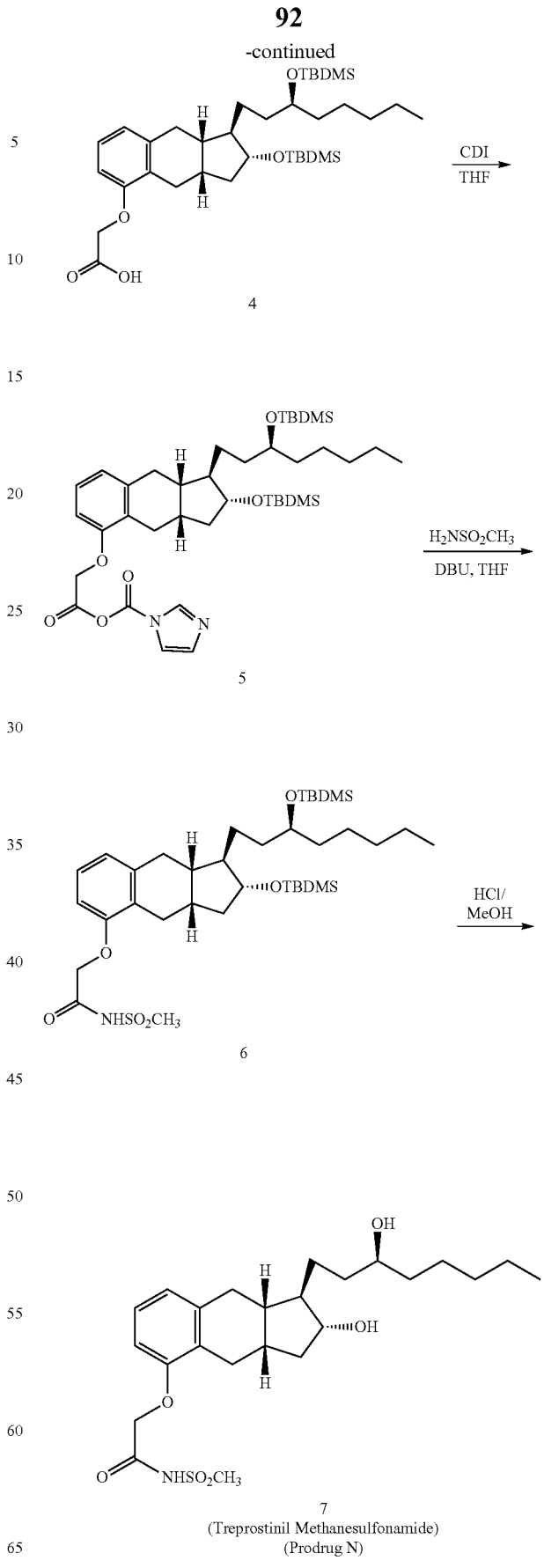

Experimental

Synthesis of Treprostinil Benzyl Ester (2)

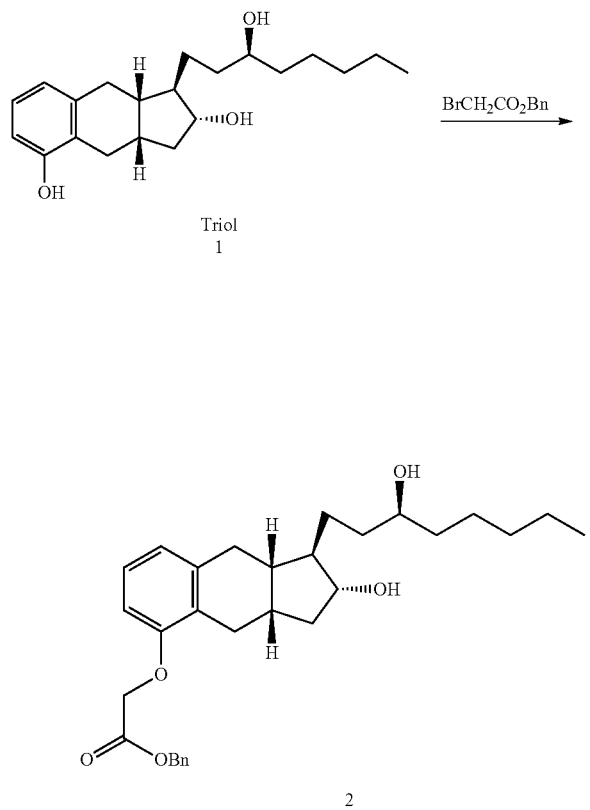

To a solution of benzindene triol (1) (240.0 g, 0.72 mol) in acetone (3.0 L) was added powdered potassium carbonate (199.5 g, 1.44 mol) and bromo benzylacetate (190.2 g, 0.83 mol) at room temperature under argon. The reaction mixture was stirred at room temperature and the progress of the reaction was monitored by tlc. After 72 h, the reaction was complete. The reaction mixture was filtered and the filtrate was evaporated in vacuo to give the treprostinil benzyl ester (2) (346.0 g, 99%) as an off white solid.

Synthesis of Di-TBDMS Treprostinil Benzyl Ester (3)

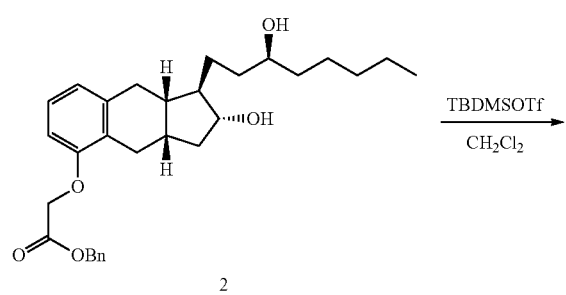

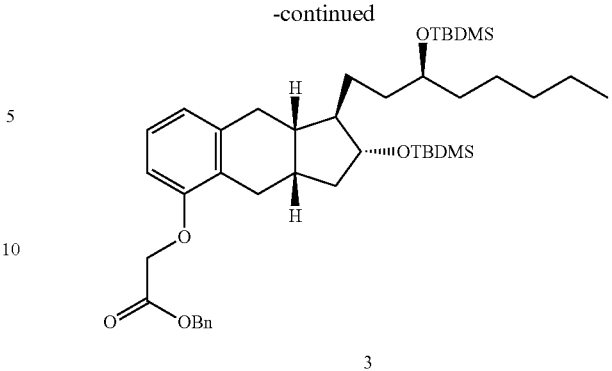

To a solution of treprostinil benzyl ester (2) (15.26 g, 31.75 mmol) in anhydrous dichloromethane (150 mL) was added 2,6-lutidine (13.61 g, 14.75 mL, 127.01 mmol) at room temperature. The clear solution was cooled to 0° C. (ice/water bath) and then added dropwise a solution of tert-butyldimethyl trifluoromethanesulfonate (TBDMSOTf) (20.98 g, 18.23 mL, 79.37 mmol) in anhydrous dichloromethane (30 mL) over a period of 20 min keeping the temperature below 5° C. under argon. After complete addition, the reaction mixture was stirred at 0-5° C. for 2 h. After 2 h, the reaction mixture was checked by tlc (EtOAc/Hexane, 1:4) and the reaction was complete. The mixture was treated with hexane (360 mL, twice the volume of dichloromethane used) and stirred for 10 min at room temperature. The mixture was passed through silica gel (230-400 mesh) (293 g) column and the compound was eluted with ethyl acetate in hexane (2-6%) to give pure di-TBDMS treprostinil benzyl ester (3) (21.7 g, 96.4%).

Synthesis of Di-TBDMS Treprostinil (4)

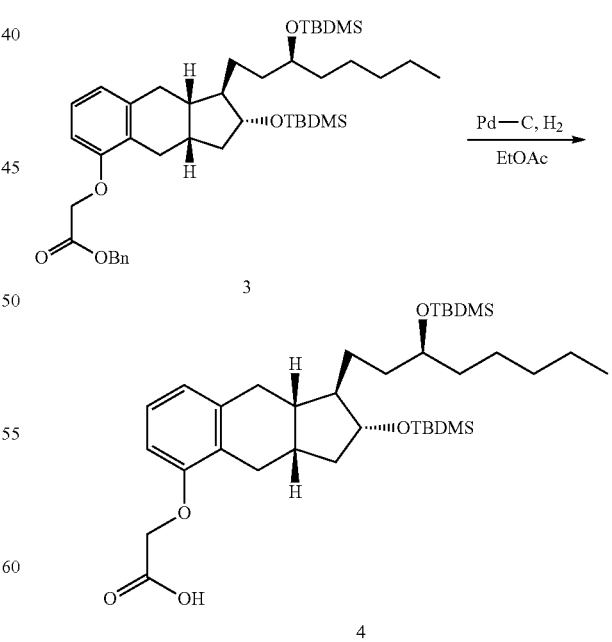

To a solution of di-TBDMS treprostinil benzyl ester (3) (21.6 g, 30.46 mmol) in ethyl acetate (320 mL) was added palladium on carbon (5 wt %, 50% water) (2.16 g). The mixture was stirred and evacuated under house vacuum and replaced by hydrogen (filled in a balloon). The process was repeated three times. The mixture was stirred at room temperature under the atmosphere of hydrogen for 2 h and checked tlc (EtOAc/Hexane, 1:4 and EtOAc, 100%). The reaction was complete. The reaction mixture was treated with Celite (7.0 g) and the filtered through a pad of silica gel (22 g) in a disposable polyethylene filter funnel, and the solid was washed with ethyl acetate (3×50 mL). The filtrate contained some carbon particles and therefore the filtrate was filtered again through a pad of Celite (10.0 g) to get clear filtrate. The clear filtrate was passed through silica gel (30 g) column and washed the silica gel with ethyl acetate (2×70 mL). The filtrate was clear and the filtrate was concentrated in vacuo at 30° C. (water bath temperature) to give di-TBDMS treprostinil (4) as a colorless viscous liquid (18.6 g, 98.7%).

To a solution of di-TBDMS treprostinil (4) (18.5 g, 29.88 mmol) in anhydrous tetrahydrofuran (190 mL) was added 1,1'-carbonyldiimidazole (CDI) (7.27 g, 44.83 mmol) in one portion at room temperature under argon. The clear reaction mixture was stirred at room temperature for 30 min and then at 75° C. (oil bath temperature) for 30 min. The reaction mixture was cooled to room temperature. To this in situ generated CDI intermediate of di-TBDMS treprostinil (5) was added methansulfonamide (8.53 g, 89.68 mmol) in one portion and stirred at room temperature for 10 min until clear solution was obtained. To this clear solution was added a solution of 1,8-diazabicyclo[5.4.0]undec-7-ene (DBU) (22.74 g, 149.37 mmol) in anhydrous tetrahydrofuran (40 mL) under argon. After complete addition, the reaction mixture was stirred at room temperature and monitored by tlc (EtOAc, 100% and MeOH/CH$_2$Cl$_2$, 1:9). After 2 h, the reaction was complete. The mixture was quenched with water (200 mL) and then extracted with EtOAc (1×200 mL), (2×100 mL). The combined EtOAc extracts were washed with water (3×100 mL), brine (1×30 mL), dried (Na$_2$SO$_4$), filtered and concentrated in vacuo to give off-white foamy solid (21.44 g). The crude product was chromatographed on silica gel (230-400 mesh) (296 g) using CH$_2$Cl$_2$ and 1-30% MeOH/CH$_2$Cl$_2$ to give di-TBDMS treprostinil methanesulfonamide (6) as a white foamy solid (15.4 g, 74.0%).

Synthesis of Di-TBDMS Treprostinil Methanesulfonamide (6)

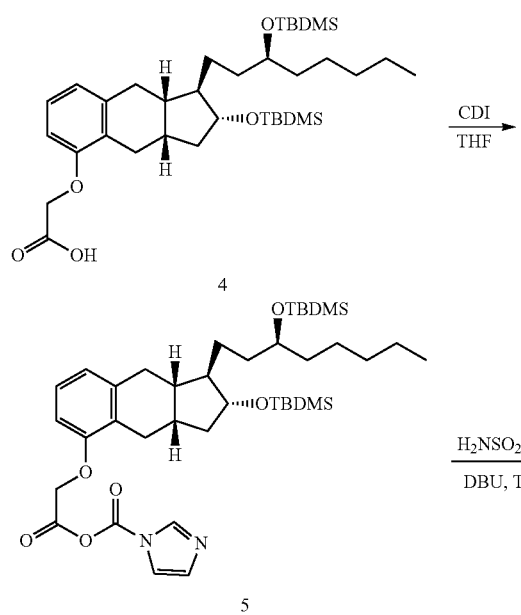

Synthesis of Treprostinil Methanesulfonamide (7)

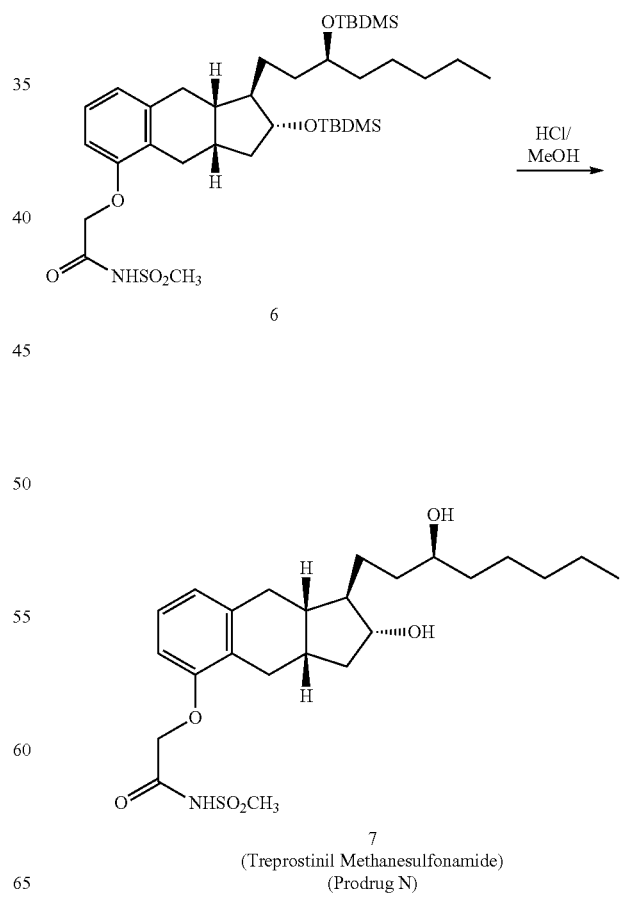

A solution of di-TBDMS treprostinil methanesulfonamide (6) (13.4 g, 19.25 mmol) in anhydrous methanol (135 mL) was cooled to 0 to 5° C. (ice/water bath). To this cold solution was added a solution of hydrogen chloride in methanol (1.25 M) (38.5 mL, 48.13 mmol) in anhydrous methanol (135 mL) over a period of 3 min under argon. The reaction mixture was stirred at 0 to 5° C. (ice/water bath) for 30 min and checked tlc (MeOH/CH$_2$Cl$_2$, 1:9). The argon was bubbled slowly through the reaction mixture for 5 min at 0 to 5° C. to remove excess hydrogen chloride. Then, the reaction mixture was evaporated in vacuo at 25° C. (water bath temperature) to remove the organic volatiles to give crude sulfonamide product (7) as a pale yellow foamy solid (11.03 g). This compound was combined with other crude product (0.80 g) to give a total weight of 11.83 g. The combined crude product was chromatographed on silica gel (175 g) column using 25-100% EtOAc/Hexane and 1-20% MeOH/EtOAc to give pure treprostinil methanesulfonamide (7) as an off-white foamy solid (6.28 g).

Example 17

Synthesis of Starting Material: Treprostinil Mono-TES Benzyl Ester (2a) Required for Various Prodrugs

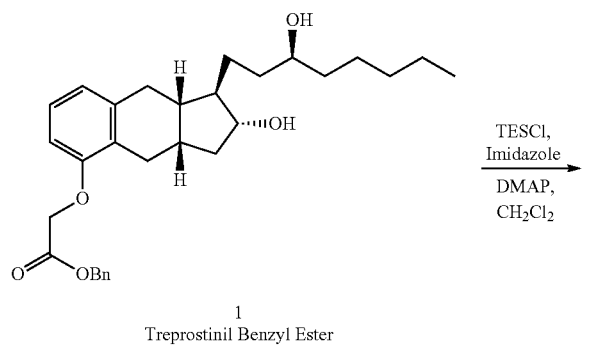

1
Treprostinil Benzyl Ester

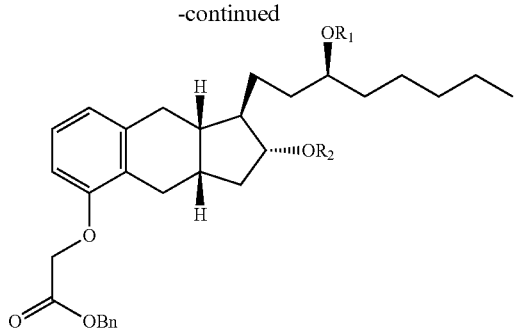

2a: R$_1$ = H, R$_2$ = TES
2b: R$_1$ = TES, R$_2$ = H

To a solution of treprostinil benzyl ester (1) (100 g, 20.80 mmol) in acetone (200 mL) was added imidazole (1.41 g, 20.80 mmol) and 4-dimethylaminopyridine (0.25 g, 2.08 mmol). To this mixture, while stirring, chlorotriethylsilane (3.5 mL, 20.80 mmol) was added using a syringe under argon atmosphere. After 1 h the reaction was found to be complete based on TLC (eluent: 20% ethyl acetate/hexane). The reaction was quenched with water (150 mL) and the organic layer was separated, washed with brine (100 mL), dried over sodium sulfate and evaporated in vacuo to obtain crude product. The crude material was purified by column chromatography using ethyl acetate:hexanes (0-11%) as mobile phase to obtain both mono-protected compound 2a (6.68 g) in 54.04% yield and 2b (0.48 g) in 3.88% yield.

Example 18

Mean Metabolite-to-Parent Ratios in Male Sprague Dawley Rats Following Single Administration of Prodrugs I, II, III and XV are presented in Table 11.

TABLE 11

| Prodrug | SC Injection | | | 6-Hour SC Infusion | | | IV Injection |
|---|---|---|---|---|---|---|---|
| | 1 mg/kg | 50 mg/kg | 100[a]/200[b] mg/kg | 1 mg/kg | 50 mg/kg | 100[a]/200[b] mg/kg | 1 mg/kg |
| I | 0.0000826 | 0.00035 | 0.000546[b] | NC | 0.000277 | 0.000493[b] | NC |
| II | 0.00058 | 0.000711 | 0.000805[b] | 0.00039 | 0.000866 | 0.000651[b] | 0.000363 |
| III | 0.0371 | 0.2134 | NC[a] | 0.0342 | 0.124 | NC[b] | 0.158 |
| XV | 0.329 | 0.251 | 0.352[a] | 0.262 | 0.39 | 0.308[a] | 0.211 |

NC = Not calculated.
[a]Animals were administered 100 mg/kg.
[b]Animals were administered 200 mg/kg.

ADDITIONAL EMBODIMENTS

1. A compound having the following formula:

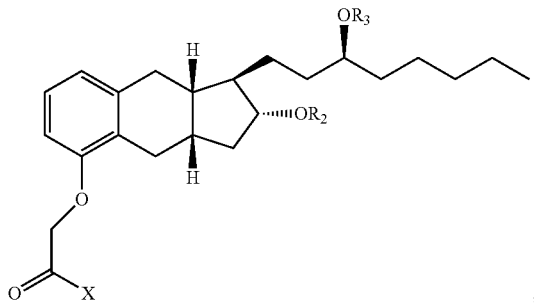

wherein:
X is OH or

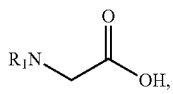

where $R_1$ is H or $C_1$-$C_4$ alkyl; and
each of $R_2$ and $R_3$ is independently selected from H, $C_{1-4}$ alkyl, or

wherein Y is $OR_4$ or $NR_4R_5$, wherein each of $R_4$ and $R_5$ is independently selected from H and $C_{1-4}$ alkyl; with a proviso that when X is OH, both of $R_2$ and $R_3$ are not H; or a pharmaceutically acceptable salt of the compound.

2. The compound of embodiment 1, wherein X is OH.
3. The embodiment of claim 2, wherein each of $R_2$ and $R_3$ is independently selected from $C_{1-4}$ alkyl.
4. The compound of embodiment 2, wherein each of $R_2$ and $R_3$ is methyl.
5. The compound of embodiment 2, wherein each of $R_2$ and $R_3$ is independently selected from H, and

6. The compound of embodiment 5, wherein one of $R_2$ and $R_3$ is

and the other of $R_2$ and $R_3$ is H.
7. The compound of embodiment 6, wherein Y is $OR_4$.
8. The compound of embodiment 7, wherein $R_4$ is methyl or H.
9. The compound of embodiment 6, wherein Y is $NR_4R_5$.
10. The compound of embodiment 9, wherein each of $R_4$ and $R_5$ is independently selected from H or methyl.
11. The compound of embodiment 9, wherein both of $R_4$ and $R_5$ are H or methyl.
12. A pharmaceutical composition, comprising (A) the compound of any one of embodiments 1-11 and (B) a pharmaceutically acceptable carrier.
13. The pharmaceutical composition of embodiment 12, which is an oral pharmaceutical composition.
14. The pharmaceutical composition of embodiment 12, which is a subcutaneous pharmaceutical composition.
15. A method of treating pulmonary hypertension comprising administering to a subject in need thereof an effective amount of the compound of any one of embodiments 1-11.
16. The method of embodiment 15, wherein the administering is performed orally.
17. The method of embodiment 15, wherein the subject is a human being.
18. The method of embodiment 15, wherein the administering is performed by an injection.
19. The method of embodiment 18, wherein the administering is performed subcutaneously.
20. The method of embodiment 19, wherein said administering is continuous subcutaneous administering.
21. The method of embodiment 18, wherein said administering results in no or less pain at a site of the injection compared to administering treprostinil.
22. A method of treating pulmonary hypertension comprising administering subcutaneously to a patient suffering from pulmonary hypertension an effective amount of a prodrug of treprostinil.
23. A method of treating pulmonary hypertension comprising selecting a patient who has experienced site pain upon subcutaneous administration of treprostinil or a pharmaceutically salt thereof and administering subcutaneously to a patient suffering from pulmonary hypertension an effective amount of a prodrug of treprostinil.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

All of the publications, patent applications and patents cited in this specification are incorporated herein by reference in their entirety.

What is claimed is:
1. A compound having the formula:

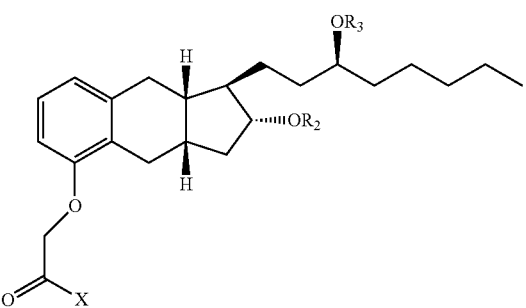

wherein X is OH, $R_2$ and $R_3$ are the same and are

101

wherein Y is NR₄R₅, wherein each of R₄ and R₅ is independently selected from H and C₁₋₄ alkyl.

2. The compound of claim 1, wherein each of R₄ and R₅ is H.

3. A pharmaceutical composition comprising the compound of claim 1 and a pharmaceutically acceptable carrier.

4. The pharmaceutical composition of claim 3, which is a composition formulated for subcutaneous administration.

5. A method of treating pulmonary hypertension comprising administering subcutaneously to a patient suffering from pulmonary hypertension an effective amount of a prodrug of treprostinil, wherein the prodrug converts in whole or in part to treprostinil in vivo following administration and has reduced affinity for one or more of the IP, DP or EP receptors locally at the site of the subcutaneous injection as compared to treprostinil, wherein the prodrug is a compound having the following formula

102

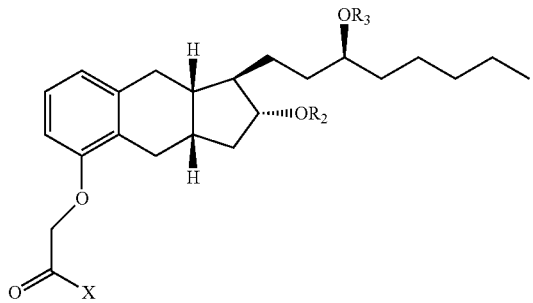

wherein X is OH, R₂ and R₃ are

Y is NR₄R₅, wherein each of R₄ and R₅ is independently selected from H and C₁₋₄ alkyl.

6. The method of claim 5, wherein each of R₄ and R₅ is H.

* * * * *